United States Patent
Springer et al.

(10) Patent No.: US 10,167,282 B2
(45) Date of Patent: *Jan. 1, 2019

(54) 1-(5-TERT-BUTYL-2-ARYL-PYRAZOL-3-YL)-3-[2-FLUORO-4-[(3-OXO-4H-PYRIDO [2,3-B]PYRAZIN- 8-YL)OXY]PHENYL]UREA DERIVATIVES AS RAF INHIBITORS FOR THE TREATMENT OF CANCER

(71) Applicants: CANCER RESEARCH TECHNOLOGY LIMITED, London (GB); INSTITUTE OF CANCER RESEARCH: ROYAL CANCER HOSPITAL (THE), London (GB)

(72) Inventors: Caroline Joy Springer, Sutton (GB); Richard Marais, Manchester (GB); Romina Girotti, Manchester (GB); Dan Niculescu-Duvaz, Sutton (GB); Ion Niculescu-Duvaz, Sutton (GB); Alfonso Zambon, Sutton (GB)

(73) Assignees: CANCER RESEARCH TECHNOLOGY LIMITED, London (GB); INSTITUTE OF CANCER RESEARCH: ROYAL CANCER HOSPITAL (THE), London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/637,365

(22) Filed: Jun. 29, 2017

(65) Prior Publication Data

US 2017/0298066 A1    Oct. 19, 2017

Related U.S. Application Data

(63) Continuation of application No. 15/038,872, filed as application No. PCT/GB2014/053490 on Nov. 25, 2014, now Pat. No. 9,725,447.

(30) Foreign Application Priority Data

Nov. 25, 2013    (GB) .................................. 1320729.5

(51) Int. Cl.
C07D 471/04    (2006.01)
(52) U.S. Cl.
CPC ................... *C07D 471/04* (2013.01)
(58) Field of Classification Search
CPC .................................................. C07D 471/04
USPC .......................................... 544/350; 514/249
See application file for complete search history.

(56) References Cited

U.S. PATENT DOCUMENTS

| | | |
|---|---|---|
| 4,082,845 A | 4/1978 | Saari et al. |
| 4,666,828 A | 5/1987 | Gusella |
| 4,683,202 A | 7/1987 | Mullis |
| 4,801,531 A | 1/1989 | Frossard |
| 5,192,659 A | 3/1993 | Simons |
| 5,272,057 A | 12/1993 | Smulson et al. |

(Continued)

FOREIGN PATENT DOCUMENTS

| | | |
|---|---|---|
| CN | 101084217 A | 12/2007 |
| EP | 1724268 A1 | 11/2006 |

(Continued)

OTHER PUBLICATIONS

U.S. Appl. No. 15/807,999, Springer et al.

(Continued)

*Primary Examiner* — Kahsay Habte
(74) *Attorney, Agent, or Firm* — Clark & Elbing LLP

(57) ABSTRACT

The present invention pertains generally to the field of therapeutic compounds. More specifically the present invention pertains to certain 1-(5-tert-butyl-2-aryl-pyrazol-3-yl)-3-[2-fluoro-4-[(3-oxo-4H-pyrido[2,3-b]pyrazin-8-yl)oxy]phenyl]urea compounds (referred herein as "TBAP compounds") that, inter alia, inhibit RAF (e.g., BRAF, CRAF, etc.). The present invention also pertains to pharmaceutical compositions comprising such compounds, and the use of such compounds and compositions, both in vitro and in vivo, to inhibit RAF (e.g., BRAF, CRAF, etc.); and to treat disorders including: proliferative disorders; cancer (including, e.g., malignant melanoma, colorectal carcinoma, pancreatic adenocarcinoma); inflammation; immunological disorders; viral infections; fibrotic disorders; disorders associated with a mutated form of RAF (e.g., BRAF, CRAF, etc.); disorders ameliorated by the inhibition of RAF (e.g., BRAF, CRAF, etc.); disorders ameliorated by the inhibition of mutant BRAF; disorders ameliorated by the inhibition of BRAF and CRAF; disorders associated with RAS mutations and/or MAPK pathway activation; disorders ameliorated by the inhibition of SRC, p38, FGFRA, VEGFR-2 (KDR), and/or LCK; etc.

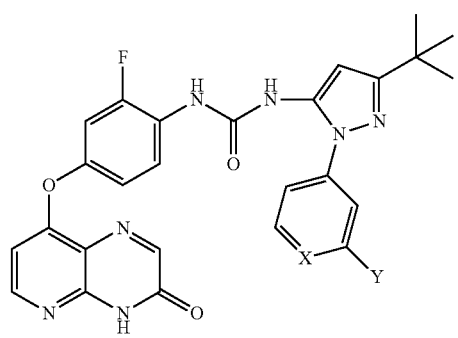

26 Claims, No Drawings

(56) References Cited

U.S. PATENT DOCUMENTS

| | | |
|---|---|---|
| 5,521,073 A | 5/1996 | Davis et al. |
| 5,877,020 A | 3/1999 | Alitalo et al. |
| 5,879,672 A | 3/1999 | Davis et al. |
| 5,882,864 A | 3/1999 | An et al. |
| 6,030,831 A | 2/2000 | Godowski et al. |
| 6,218,529 B1 | 4/2001 | An et al. |
| 6,258,809 B1 | 7/2001 | Rajagopalan et al. |
| 6,492,529 B1 | 12/2002 | Kapadia et al. |
| 7,625,922 B2 | 12/2009 | Niculescu-Duvaz et al. |
| 7,951,819 B2 | 5/2011 | Niculescu-Duvaz et al. |
| 8,198,279 B2 | 6/2012 | Springer et al. |
| 8,383,816 B2 | 2/2013 | Niculescu-Duvaz et al. |
| 8,546,387 B2 | 10/2013 | Springer et al. |
| 8,815,896 B2 | 8/2014 | Springer et al. |
| 8,912,191 B2 | 12/2014 | Springer et al. |
| 9,120,789 B2 | 9/2015 | Springer et al. |
| 9,155,737 B2 | 10/2015 | Springer et al. |
| 9,439,893 B2 | 9/2016 | Springer et al. |
| 9,540,372 B2 | 1/2017 | Springer et al. |
| 9,725,447 B2 * | 8/2017 | Springer .............. C07D 471/04 |
| 9,820,976 B2 | 11/2017 | Springer et al. |
| 2004/0082583 A1 | 4/2004 | Cheung et al. |
| 2007/0287838 A1 | 12/2007 | Niculescu-Duvaz et al. |
| 2008/0113967 A1 | 5/2008 | Flynn et al. |
| 2009/0325945 A1 | 12/2009 | Niculescu-Duvaz et al. |
| 2011/0053946 A1 | 3/2011 | Niculescu-Duvaz et al. |
| 2012/0238568 A1 | 9/2012 | Springer et al. |
| 2014/0121212 A1 | 5/2014 | Springer et al. |
| 2014/0357663 A1 | 12/2014 | Springer et al. |
| 2015/0182526 A1 | 7/2015 | Springer et al. |
| 2016/0002230 A1 | 1/2016 | Springer et al. |
| 2016/0030405 A1 | 2/2016 | Springer et al. |

FOREIGN PATENT DOCUMENTS

| | | |
|---|---|---|
| JP | S5665863 A | 6/1981 |
| JP | S5738777 A | 3/1982 |
| NZ | 555005 A | 10/2010 |
| WO | WO-98/13350 A1 | 4/1998 |
| WO | WO-99/16438 A1 | 4/1999 |
| WO | WO-99/21859 A1 | 5/1999 |
| WO | WO-00/35436 A2 | 6/2000 |
| WO | WO-00/40235 A2 | 7/2000 |
| WO | WO-00/45435 A1 | 8/2000 |
| WO | WO-01/05392 A2 | 1/2001 |
| WO | WO-01/36383 A1 | 5/2001 |
| WO | WO-01/046196 A1 | 6/2001 |
| WO | WO-02/102367 A1 | 12/2002 |
| WO | WO-03/056036 A2 | 7/2003 |
| WO | WO-2004/014300 A2 | 2/2004 |
| WO | WO-2004/083458 A1 | 9/2004 |
| WO | WO-2004/110452 A1 | 12/2004 |
| WO | WO-2006/003378 A1 | 1/2006 |
| WO | WO-2006/024834 A1 | 3/2006 |
| WO | WO-2006/040568 A1 | 4/2006 |
| WO | WO-2006/043090 A1 | 4/2006 |
| WO | WO-2006/067466 A2 | 6/2006 |
| WO | WO-2007/059202 A2 | 5/2007 |
| WO | WO-2007/064872 A2 | 6/2007 |
| WO | WO-2007/067444 A1 | 6/2007 |
| WO | WO-2007/076092 A2 | 7/2007 |
| WO | WO-2007/125330 A1 | 11/2007 |
| WO | WO-2008/009700 A1 | 1/2008 |
| WO | WO-2008/044688 A1 | 4/2008 |
| WO | WO-2009/007934 A2 | 1/2009 |
| WO | WO-2009/077766 A1 | 6/2009 |
| WO | WO-2009/130487 A1 | 10/2009 |
| WO | WO-2010/038085 A2 | 4/2010 |
| WO | WO-2010/038086 A2 | 4/2010 |
| WO | WO-2010/067130 A1 | 6/2010 |
| WO | WO-2010/067131 A1 | 6/2010 |
| WO | WO-2010/112936 A1 | 10/2010 |
| WO | WO-2011/004276 A1 | 1/2011 |
| WO | WO-2011/028540 A1 | 3/2011 |
| WO | WO-2011/048111 A1 | 4/2011 |
| WO | WO-2011/070368 A1 | 6/2011 |
| WO | WO-2011/070369 A1 | 6/2011 |
| WO | WO-2011/092469 A1 | 8/2011 |
| WO | WO-2011/121366 A1 | 10/2011 |
| WO | WO-2011/124923 A2 | 10/2011 |
| WO | WO-2011/124930 A1 | 10/2011 |
| WO | WO-2011/158039 A1 | 12/2011 |
| WO | WO-2011/158042 A2 | 12/2011 |
| WO | WO-2011/158044 A2 | 12/2011 |
| WO | WO-2012/008564 A1 | 1/2012 |
| WO | WO-2012/052753 A1 | 4/2012 |
| WO | WO-2012/149547 A1 | 11/2012 |
| WO | WO-2012/177725 A1 | 12/2012 |
| WO | WO-2013/001372 A2 | 1/2013 |
| WO | WO-2013/033133 A1 | 3/2013 |
| WO | WO-2013/050756 A1 | 4/2013 |
| WO | WO-2013/050757 A1 | 4/2013 |
| WO | WO-2014/027209 A1 | 2/2014 |
| WO | WO-2014/033446 A1 | 3/2014 |
| WO | WO-2014/033447 A2 | 3/2014 |
| WO | WO-2014/033448 A1 | 3/2014 |
| WO | WO-2014/033449 A1 | 3/2014 |
| WO | WO-2014/076484 A1 | 5/2014 |
| WO | WO-2014/140582 A1 | 9/2014 |
| WO | WO-2014/140597 A1 | 9/2014 |
| WO | WO-2014/162121 A1 | 10/2014 |
| WO | WO-2014/162122 A1 | 10/2014 |
| WO | WO-2014/162126 A1 | 10/2014 |
| WO | WO-2015/075483 A1 | 5/2015 |
| WO | WO-2015/092423 A1 | 6/2015 |
| WO | WO-2015/121444 A1 | 8/2015 |
| WO | WO-2015/121660 A1 | 8/2015 |
| WO | WO-2016/051186 A1 | 4/2016 |
| WO | WO-2016/051187 A1 | 4/2016 |
| WO | WO-2016/051188 A1 | 4/2016 |

OTHER PUBLICATIONS

Abasolo et al.,"Kinetic study on the anelation of heterocycles. 2. pyrido[2,3-b]pyrazine and pyrido[3,4 b]pyrazine derivatives synthesized by the Hinsberg reaction," J Heterocyclic Chem. 27(2):157-162 (1990).

Adams et al., "Roles of ephrinB ligands and EphB receptors in cardiovascular development: demarcation of arterial/venous domains, vascular morphogenesis, and sprouting angiogenesis," Genes Dev. 13(3):295-306 (1999).

Akula et al.,"Raf promotes human herpesvirus-8 (HHV-8/KSHV) infection," Oncogene. 23(30):5227-5241 (2004).

Alon et al., "Vascular endothelial growth factor acts as a survival factor for newly formed retinal vessels and has implications for retinopathy of prematurity," Nat Med. 1(10):1024-1028 (1995).

Ananthanarayanan et al., "Reaction of azides in presence of aluminium chloride," Indian J Chem. 27B:156-7 (1988).

Anastasaki et al.,"Continual low-level MEK inhibition ameliorates cardio-facio-cutaneous phenotypes in zebrafish," Dis Model Mech. 5(4):546-552 (2012).

Angerer et al., "Demonstration of tissue-specific gene expression by in situ hybridization," Methods Enzymol. 152:649-61 (1987).

Antony et al.,"C-RAF Mutations confer resistance to RAF inhibitors," Cancer Res. 73(15):4840-4851 (2013).

Arcaini et al., "The BRAF V600E mutation in hairy cell leukemia and other mature B-cell neoplasms," Blood. 119(1):188-191 (2012) (5 pages).

Asrih et al., "Role of mitogen-activated protein kinase pathways in multifactorial adverse cardiac remodeling associated with metabolic syndrome," Mediators Inflamm. 2013:367245 (2013) (12 pages).

Auvray et al., "Preparation and nucleophilic substitution of (E)-1-bromo-2-phenylsulfonyl-2-alkenes and 3-acetoxy-2-phenylsulfonyl-1-alkenes," Tetrahedron. 44(19):6095-106 (1988).

Avenoza et al., "New efficient synthesis of 4-amino-3-arylphenols," Synthesis. 671-674 (1995).

Badalian-Very et al., "Recent advances in the understanding of Langerhans cell histiocytosis," Br J Haematol. 156(2): 163-172 (2012).

(56) References Cited

OTHER PUBLICATIONS

Ballesteros et al., "Study of the catalytic properties of tris (3,6-dioxaheptyl) amine (tda-1) in heteroaromatic nucleophilic substitution of chloropyridines and their n-oxides," Tetrahedron. 43(11):2557-64 (1987).
Bart et al., "Development of novel, highly potent inhibitors of V-RAF murine sarcoma viral oncogene homologue B1 (BRAF): increasing cellular potency through optimization of a distal heteroaromatic group," J Med Chem. 53:2741-56 (2010).
Bates et al., "A new synthesis of pyrazinol[2,3-c]isoquinolines," Aust J Chem. 43(1): 179-184 (1990).
Bekerman et al., "Comparative kinetic studies on the synthesis of quinoxalinone derivatives and pyrido[2,3-b]pyrazinone derivatives by the hinsberg reaction," J Heterocyclic Chem. 29:129-33 (1992).
Belgore et al., "Localisation of members of the vascular endothelial growth factor (VEGF) family and their receptors in human atherosclerotic arteries," J Clin Pathol. 57(3): 266-272 (2004).
Benn et al., "Hepatitis B virus HBx protein activates Ras-GTP complex formation and establishes a Ras, Raf, MAP kinase signaling cascade," Proc Natl Acad Sci USA. 91(22): 10350-10354 (1994).
Berge et al., "Pharmaceutical salts," J Pharm Sci. 66(1):1-19 (1977).
Bergman et al., "Synthesis of pyridopyrazino[2,3-b]indoles and 10H-indolo[3,2-g]pteridins," Recl Trav Chim Pays-Bas. 115(1): 31-36 (1996).
Berry et al., "TNF-alpha in asthma," Curr Opin Pharmacol. 7(3): 279-282 (2007).
Bhatt et al., "Preparation of $N^1$-2-phenyl-4-quinolinoyl-$N^3$-aryl thioureas," J Instit Chem (India). 52:113-4 (1980).
Bianchi et al., "Compounds with antiulcer and antisecretory activity," Eur J Med Chem. 16(4):321-6 (1981).
Borthakur et al., "New direct synthesis of thioamides from carboxylic acids," Tetrahedron Letters. 36(37):6745-6 (1995).
Bos, "Ras oncogenes in human cancer: a review," Cancer Res. 49(17):4682-9 (1989).
Broekhof et al., "Novel applications of alpha-aminosubstituted diphenylphosphine oxides. The conversion of aldehydes into alpha-aminomethylketones," Tetrahedron Lett. 22(29):2799-802 (1981).
Brooks et al., "Integrin alpha v beta 3 antagonists promote tumor regression by inducing apoptosis of angiogenic blood vessels," Cell. 79(7): 1157-64 (1994).
Brose et al., "BRAF and RAS mutations in human lung cancer and melanoma," Cancer Res. 62(23):6997-7000 (2002).
Bruckner et al.,"Tyrosine phosphorylation of transmembrane ligands for Eph receptors," Science. 275(5306):1640-3 (1997).
Bruder et al., "Serum-, TPA-, and Ras-induced expression from Ap-1/Ets-driven promoters requires Raf-1 kinase," Genes Dev. 6(4):545-56 (1992).
Byeon et al., "The role of Src kinase in macrophage-mediated inflammatory responses," Mediators Inflamm. 2012:512926 (2012) (19 pages).
Calhoun et al., "BRAF and FBXW7 (CDC4, FBW7, AGO, SEL 10) mutations in distinct subsets of pancreatic cancer: potential therapeutic targets," Am J Pathol. 163(4): 1255-1260 (2003).
Cantrell, "GTPases and T cell activation," Immunol Rev.192:122-30 (2003).
Chan et al., "Regulation of antigen receptor signal transduction by protein tyrosine kinases," Curr Opin Immunol. 8(3):394-401 (1995).
Chapman et al., "Improved survival with vemurafenib in melanoma with BRAF V600E mutation," N Engl J Med. 364(26): 2507-2516 (2011).
Chapman et al., "Initial genome sequencing and analysis of multiple myeloma," Nature. 471(7339):467-72 (2011).
Ciampi et al., "Oncogenic AKAP9-BRAF fusion is a novel mechanism of MAPK pathway activation in thyroid cancer," J Clin Invest. 115(1): 94-101 (2005).
Clare et al., "Protease inhibitors: synthesis of a series of bacterial collagenase inhibitors of the sulfonyl amino acyl hydroxamate type," J Med Chem. 44(13):2253-8 (2001).

Clark-Lewis et al., "Quinoxaline derivatives. Part IV. Dihydro-oxo-1 : 4 : 5-triazanaphthalenecarboxyureides and related spiroHydantoins," J Chem Soc. 430-439 (1957).
Cohen et al., "Lack of BRAF mutation in primary uveal melanoma," Invest Ophthalmol Vis Sci. 44(7):2876-8 (2003).
Colville-Nash et al., "Angiogenesis and rheumatoid arthritis: pathogenic and therapeutic implications," Ann Rheum Dis. 51(7):919-25 (1992).
Comins et al., "Grignard addition to 1-acyl salts of chiral 4-alkoxypyridines. A new enantioselective preparation of 2-alkyl-4-alkoxypyridines. A new enantioselective preparation of 2-alkyl-2,3-dihydro-4-pyridones," Tetrahedron Lett. 35(40):7343-6 (1994).
Cooper, "Membrane-associated tyrosine kinases as molecular switches," Semin Cell Biol. 5(6):377-87 (1994).
Corcoran et al., "BRAF gene amplification can promote acquired resistance to MEK inhibitors in cancer cells harboring the BRAF V600E mutation," Sci Signal. 3(149):ra84 (2010) (10 pages).
Correia, "Reaction of phenylglyoxal with aniline under acidic conditions," J Org Chem 43(17):3394-6 (1978).
Coulthard et al., "p38(MAPK): stress responses from molecular mechanisms to therapeutics," Trends Mol Med. 15(8): 369-379 (2009).
Courtneidge et al., "The Src family of protein tyrosine kinases: regulation and functions," Dev Suppl. 57-64 (1993).
Cowely et al., "Activation of MAP kinase kinase is necessary and sufficient for PC12 differentiation and for transformation of NIH 3T3 cells," Cell. 77(6):841-52 (1994).
Cuadrado et al., "Mechanisms and functions of p38 MAPK signalling," Biochem J. 429(3): 403-417 (2010).
Cushman et al., "19F NMR studies on the mechanism of riboflavin synthase. Synthesis of 6-(Trifluoromethyl)-7-oxo-8-(D-ribityl)lumazine and 6-(Trifluoromethyl)-7-methyl-8-(D-ribityl)lumazine," J Org Chem. 57(21): 5630-5643 (1992).
Damodar Reddy et al., "Role of MAP kinase pathways in primitive neuroectodermal tumors," Anticancer Res. 21(4A): 2733-8 (2001).
Davies et al., "Mutations of the BRAF gene in human cancer," Nature. 417(6892):949-54 (2002).
Davis et al., "Isolation of angiopoietin-1, a ligand for the TIE2 receptor, by secretion-trap expression cloning," Cell. 87(7):1161-9 (1996).
Davis et al., "Raf and mitogen-activated protein kinase regulate stellate cell collagen gene expression," J Biol Chem. 271(19): 11039-11042 (1996) (5 pages).
Denekamp, "Review article: angiogenesis, neovascular proliferation and vascular pathophysiology as targets for cancer therapy," Br J Radiol. 66(783):181-96 (1993).
Dettner et al., "Chemical defense of giant springtail Tetrodontophora bielanensis (Waga) (Insecta: Collembola)," J Chem Ecol. 22(5): 1051-1074 (1996).
Dhomen et al., "Oncogenic Braf induces melanocyte senescence and melanoma in mice," Cancer Cell. 15(4): 294-303 (2009).
Dickson et al., "Raf functions downstream of Ras1 in the Sevenless signal transduction pathway," Nature. 360(6404):600-3 (1992).
Downward, "Targeting RAS signalling pathways in cancer therapy," Nat Rev Cancer. 3(1):11-22 (2003).
Dubey et al., "Structure and reactions of monoanils obtained from 2,3-pyridinediamines," Indian J Chem. 40B(5): 361-367 (2001).
DuBois, "Amination of aryl sulfamate esters. A convenient general synthesis of aliphatic sulfamides," J Org Chem. 45:5373-5 (1980).
Ellis et al., "VEGF-targeted therapy: mechanisms of anti-tumour activity," Nat Rev Cancer. 8(8): 579-591 (2008).
Falchook et al., "RAF inhibitor dabrafenib (GSK2118436) is active in melanoma brain metastases, multiple BRAF genotypes and diverse cancers" NIH Public Access Author Manuscript 20 pages Jul. 24, 2014, published in final edited form as "Dabrafenib in patients with melanoma, untreated brain metastases, and other solid tumours: a phase 1 dose-escalation trial," Lancet. 379(9829): 1893-1901 (2012).
Fernandez-Medarde et al., "Ras in cancer and developmental diseases," Genes Cancer. 2(3): 344-358 (2011).
Fidler et al., "The implications of angiogenesis for the biology and therapy of cancer metastasis," Cell. 79(2):185-8 (1994).
Flaherty et al., "Inhibition of mutated, activated BRAF in metastatic melanoma," N Engl J Med. 363(9): 809-819 (2010).

(56) References Cited

OTHER PUBLICATIONS

Folkman et al., "Angiogenesis," J Biol Chem. 267(16):10931-4 (1992).
Folkman, "Angiogenesis and angiogenesis inhibition: An overview," EXS. 79:1-8 (1997).
Folkman, "Angiogenesis in cancer, vascular, rheumatoid and other disease," Nat Med. 1(1):27-31 (1995).
Folkman, "The role of angiogenesis in tumor growth," Semin Cancer Biol. 3(2):65-71 (1992).
Fourrey et al., "Preparation of stable 1,4-dihydropyrazines," J Chem Soc., Perkins Transactions 1: Org. and Bio. Chem. 8:1841-3 (1987).
Friedlander et al., "Definition of two angiogenic pathways by distinct alpha v integrins," Science. 270(5241):1500-2 (1995).
Fujita et al., "ERK and p38 mediate high-glucose-induced hypertrophy and TGF-beta expression in renal tubular cells," Am J Physiol Renal Physiol. 286(1): F120-6 (2004).
Fukuda et al., "Epstein-Barr virus latent membrane protein 2A mediates transformation through constitutive activation of the Ras/P13-K/Akt Pathway," J Virol. 81(17): 9299-9306 (2007).
Gale et al., "Growth factors acting via endothelial cell-specific receptor tyrosine kinases: VEGFs, angiopoietins, and ephrins in vascular development," Genes Dev. 13(9)1055-66 (1999).
Galons, "Cyclisation indolique selon Bischler en presence d'acides de Lewis," J Heterocyclic Chemistry. 18:561-63 (1981).
Garnett et al., "Guilty as charged: B-RAF is a human oncogene," Cancer Cell. 6(4):313-9 (2004).
Gaudi et al., "Molecular bases of cutaneous and uveal melanomas," Patholog Res Int. 2011:159421 (2011) (8 pages).
Genot et al.,"Ras regulation and function in lymphocytes," Curr Opin Immunol. 12(3):289-94 (2000) (6 pages).
Geppert et al., "Lipopolysaccharide signals activation of tumor necrosis factor biosynthesis through the ras/raf-1/MEK/MAPK pathway," Mol Med. 1(1): 93-103 (1994).
Giannotti et al., "New dibenzothiadiazepine derivatives with antidepressant activities," J Med Chem 34(4):1356-62 (1991).
Giardina et al., "Replacement of the quinoline system in 2-phenyl-4-quinolinecarboxamide NK-3 receptor antagonists," Farmaco. 54(6):364-74 (1999).
Girotti et al., "Inhibiting EGF receptor or SRC family kinase signaling overcomes BRAF inhibitor resistance in melanoma," Cancer Discov. 3(2): 158-167 (2013).
Glinka, "Synthesis and structure of new hetercyclic systems containing the sulfamide group," Pol J Chem. 65:2053-5 (1991).
Golub et al., "Molecular classification of cancer: class discovery and class prediction by gene expression monitoring," Science. 286(5439):531-7 (1999).
Gorden et al., "Analysis of BRAF and N-RAS mutations in metastatic melanoma tissues," Cancer Res. 63(14):3955-7 (2003).
Graf et al., "Mitogen-activated protein kinase activation is involved in platelet-derived growth factor-directed migration by vascular smooth muscle cells," Hypertension. 29(1 Pt. 2): 334-339 (1997).
Gray-Schopfer et al., "Melanoma biology and new targeted therapy," Nature. 445(7130):851-7 (2007).
Greger et al., "Combinations of BRAF, MEK, and P13K/mTOR inhibitors overcome acquired resistance to the BRAF inhibitor GSK2118436 dabrafenib, mediated by NRAS or MEK mutations," Mol Cancer Ther. 11(4): 909-920 (2012).
Grosios et al., "Angiogenesis inhibition by the novel VEGF receptor tyrosine kinase inhibitor, PTK787/ZK222584, causes significant anti-arthritic effects in models of rheumatoid arthritis," Inflamm Res. 53(4): 133-142 (2004).
Guarna et al., "Synthesis of a new enantiopure bicyclic gamma/delta-amino acid (BTKa) derived from tartaric acid and alpha-amino acetophenone," Tetrahedron. 58(49):9865-70 (2002).
Haase et al., "A role for mitogen-activated protein kinase activation by integrins in the pathogenesis of psoriasis," J Clin Invest. 108(4): 527-536 (2001).
Haesslein et al., "Recent advances in cyclin-dependent kinase inhibition. Purine-based derivatives as anti-cancer agents. Roles and perspectives for the future," Curr Top Med Chem. 2(9):1037-50 (2002).
Hammond et al., "Structure-activity relationships in a series of NPY Y5 antagonists: 3-amido-9-ethylcarbazoles, core-modified analogues and amide isosteres," Bioorg Med Chem Lett. 13(12):1989-92 (2003).
Haroche et al., "High prevalence of BRAF V600E mutations in Erdheim-Chester disease but not in other non-Langerhans cell histiocytoses," Blood. 120(3): 2700-2703 (2012) (5 pages).
Heidorn et al., "Kinase-dead BRAF and oncogenic RAS cooperate to drive tumor progression through CRAF," Cell. 140(2): 209-221 (2010).
Helbling et al., "The receptor tyrosine kinase EphB4 and ephrin-B ligands restrict angiogenic growth of embryonic veins in Xenopus laevis," Development. 127(2):269-78 (2000).
Hirayama et al., "Design, synthesis and biological activity of YM-60828 derivatives: potent and orally-bioavailable factor Xa inhibitors based on naphthoanilide and naphthalensulfonanilide templates," Bioorg Med Chem. 10(8):2597-610 (2002).
Holland et al., "Bidirectional signalling through the EPH-family receptor Nuk and its transmembrane ligands," Nature. 383(6602):722-5 (1996).
Hu et al., "Mutation that blocks ATP binding creates a pseudokinase stabilizing the scaffolding function of kinase suppressor of Ras, CRAF and BRAF," Proc Natl Acad Sci USA. 108(15): 6067-6072 (2011) (9 pages).
Hwang et al., "Over-expression of c-raf-1 proto-oncogene in liver cirrhosis and hepatocellular carcinoma," Hepatol Res. 29(2): 113-121 (2004).
Ingber et al., "Synthetic analogues of fumagillin that inhibit angiogenesis and suppress tumour growth," Nature. 348(6301):555-7 (1990).
Inoue et al., "Vascular endothelial growth factor (VEGF) expression in human coronary atherosclerotic lesions: possible pathophysiological significance of VEGF in progression of atherosclerosis," Circulation. 98(20): 2108-2116 (1998).
International Preliminary Report on Patentability for International Application No. PCT/GB2005/004081, dated Apr. 24, 2007 (8 pages).
International Preliminary Report on Patentability for International Application No. PCT/GB2007/001534, dated Oct. 28, 2008 (10 pages).
International Preliminary Report on Patentability for International Application No. PCT/GB2008/004208, dated Jun. 22, 2010 (6 pages).
International Preliminary Report on Patentability for International Application No. PCT/GB2009/001077, dated Oct. 26, 2010 (6 pages).
International Preliminary Report on Patentability for International Application No. PCT/GB2011/000106, dated Aug. 7, 2012 (7 pages).
International Preliminary Report on Patentability for International Application No. PCT/GB2014/053489, dated May 31, 2016 (6 pages).
International Preliminary Report on Patentability for International Application No. PCT/GB2014/053490, dated May 31, 2016 (7 pages).
International Search Report and Written Opinion for International Application No. PCT/GB2005/004081, dated Feb. 2, 2006 (12 pages).
International Search Report and Written Opinion for International Application No. PCT/GB2008/004208, dated Mar. 5, 2009 (7 pages).
International Search Report and Written Opinion for International Application No. PCT/GB2009/001077, dated Sep. 21, 2009 (8 pages).
International Search Report and Written Opinion for International Application No. PCT/GB2011/000106, dated Mar. 18, 2011 (10 pages).
International Search Report and Written Opinion for International Application No. PCT/GB2014/053489, dated Jan. 15, 2015 (11 pages).

(56) References Cited

OTHER PUBLICATIONS

International Search Report and Written Opinion for International Application No. PCT/GB2014/053490, dated Jan. 26, 2015 (10 pages).
International Search Report for International Application No. PCT/GB2007/001534, dated Sep. 6, 2007 (4 pages).
Ishii et al., "First synthesis and reactivities of isolable dithiiranes and their 1-oxides," Bulletin of the Chemical Society of Japan. 70:509-23 (1997).
Itaya et al., "Syntheses of the marine ascidian purine aplidiamine and its 9-beta-d-ribofuranoside," Tetrahedron Lett. 39:4695-6 (1998).
Jaffee et al., "Inhibition of Map kinase kinase (MEK) results in an anti-inflammatory response in vivo," Biochem Biophys Res Commun. 268(2): 647-651 (2000).
Janvier et al., "Ammonium chloride-promoted four-component synthesis of pyrrolo[3,4-lo]pyridin-5-one," J Am Chem Soc. 124(11):2560-7 (2002).
Jessen et al., "MEK inhibition exhibits efficacy in human and mouse neurofibromatosis tumors," J Clin Invest 123(1): 340-347 (2013).
Ji et al., "ERK MAP kinase activation in superficial spinal cord neurons induces prodynorphin and NK-1 upregulation and contributes to persistent inflammatory pain hypersensitivity," J Neurosci. 22(2): 478-85 (2002).
Jo et al., "MEK inhibitor, U0126, attenuates cisplatin-induced renal injury by decreasing inflammation and apoptosis," Kidney Int. 67(2): 458-466 (2005).
Johnson et al., "Preparation and reactions of sulfonimidoyl chlorides," J Org Chem. 44(13):2055-61 (1979).
Johnson et al., "The role of MKK1/2 kinase activity in human cytomegalovirus infection," J Gen Virol. 82(Pt 3): 493-497 (2001).
Jursic, "Synthetic application of micellar catalysis. williamson's synthesis of ethers," Tetrahedron. 44(21):6677-80 (1988).
Kahlon et al., "Angiogenesis in atherosclerosis," Can J Cardiol. 8(1):60-4 (1992).
Kam et al.,"TNF-alpha antagonists for the treatment of Crohn's disease," Expert Opin Pharmacother. 1(4): 615-622 (2000).
Karim et al.,"Impaired inflammatory pain and thermal hyperalgesia in mice expressing neuron-specific dominant negative mitogen activated protein kinase kinase (MEK)," Mol Pain. 2: 2 (2006) (10 pages).
Keffer et al., "Transgenic mice expressing human tumour necrosis factor: a predictive genetic model of arthritis," EMBO J. 10(13): 4025-4031 (1991).
Kolch et al., "Raf-1 protein kinase is required for growth of induced NIH/3T3 cells," Nature. 349(6308):426-8 (1991).
Kotoula et al., "Mutational analysis of the BRAF, RAS and EGFR genes in human adrenocortical carcinomas," Endocr Relat Cancer. 16(2): 565-572 (2009).
Lala et al., "Role of nitric oxide in tumor progression: lessons from experimental tumors," Cancer Metastasis Rev. 17(1):91-106 (1998).
Leese et al., "Polyazanaphthalenes. Part I. Some derivatives of 1:4:5-triazanaphthalene and quinoxaline," J Chem Soc. 303-309 (1955).
Lemonnier et al., "Role of N-cadherin and protein kinase C in osteoblast gene activation induced by the S252W fibroblast growth factor receptor 2 mutation in Apert craniosynostosis," J Bone Miner Res. 16(5):832-45 (2001).
Li et al., "Activation of NF-kappaB via a Src-dependent Ras-MAPK-pp90rsk pathway is required for Pseudomonas aeruginosa-induced mucin overproduction in epithelial cells," Proc Natl Acad Sci USA. 95(10): 5718-5723 (1998).
Lin et al., "VEGF and its receptor-2 involved in neuropathic pain transmission mediated by P2X2(/)3 receptor of primary sensory neurons," Brain Res Bull. 83(5):284-291 (2010).
Lindauer et al., "Dasatinib," Recent Results Cancer Res. 184: 83-102 (2010).
Link et al., "Phosphodiesterase 4 inhibition but not beta-adrenergic stimulation suppresses tumor necrosis factor-alpha release in peripheral blood mononuclear cells in septic shock," Crit Care. 12(6):R159 (2008) (9 pages).
Liu et al., "Effects of overexpression of ephrin-B2 on tumour growth in human colorectal cancer," Br J Cancer. 90(8):1620-6 (2004).
Long et al., "Prognostic and clinicopathologic associations of oncogenic BRAF in metastatic melanoma," J Clin Oncol. 29(10): 1239-1246 (2011).
Lorenz et al., "Cardiac hypertrophy: targeting Raf/MEK/ERK1/2-signaling," Int J Biochem Cell Biol. 41(12): 2351-2355 (2009).
Lowenberg et al., "Specific inhibition of c-Raf activity by semapimod induces clinical remission in severe Crohn's disease," J Immunol. 175(4): 2293-2300 (2005).
Lozinskii et al., "Alkylthio derivatives of the aminoketene S,N-Acetals of heterocyclic beta-dicarbonyl compounds: one stage synthesis and properties," Chemistry of Heterocyclic Compounds. 38(9):1077-80 (2002).
Luo et al., "Coxsackievirus B3 replication is reduced by inhibition of the extracellular signal-regulated kinase (ERK) signaling pathway," J Virol. 76(7): 3365-3373 (2002).
Ma et al., "The ERK/MAPK pathway, as a target for the treatment of neuropathic pain," Expert Opin Ther Targets. 9(4):699-713 (2005).
Maddahi et al.,"Cerebral ischemia induces microvascular pro-inflammatory cytokine expression via the MEK/ERK pathway," J Neuroinflammation. 7:14 (2010) (13 pages).
Mammas et al., "Involvement of the ras genes in female genital tract cancer," Int J Oncol. 26(5):1241-1255 (2005).
Mansour et al., "Transformation of mammalian cells by constitutively active MAP kinase kinase," Science. 265(5174):966-70 (1994).
Marais et al., "Differential regulation of Raf-1, A-Raf, and B-Raf by oncogenic ras and tyrosine kinases," J Biol Chem. 272(7):4378-83 (1997).
Martich et al., "Detection of interleukin 8 and tumor necrosis factor in normal humans after intravenous endotoxin: the effect of antiinflammatory agents," J Exp Med. 173(4):1021-1024 (1991).
Martin et al., "Update on lymphocyte specific kinase inhibitors: a patent survey," Expert Opin Ther Pat. 20(11): 1573-1593 (2010).
Mashelkar et al., "Synthesis of some novel 4-substituted coumarins having potential biological activity (Part II)," Indian J Chem. 45B(4): 967-971 (2006).
Mataloni et al., "Synthesis of secondary amines by reduction of alpha-amidoalkylphenyl sulfones with sodium acetoxyborohydride," Synlett. 8:1129-32 (2003).
McCann et al.,"Apremilast, a novel PDE4 inhibitor, inhibits spontaneous production of tumour necrosis factor-alpha from human rheumatoid synovial cells and ameliorates experimental arthritis," Arthritis Res Ther. 12(3): R107 (2010) (11 pages).
McKay et al., "Complexity in KSR function revealed by Raf inhibitor and KSR structure studies," Small GTPases. 2(5):276-281 (2011) (7 pages).
McKillop et al., "Applications of ethyl carboethoxyformimidate to heterocyclic synthesis: preparation of condensed pyrazinones and 1,4-oxazinones," Synthesis. 3:301-304 (1997).
McMahon, "VEGF receptor signalling in tumor angiogenesis," Oncologist. 5(suppl I):3-10 (2000).
Mei et al., "Distribution, levels and phosphorylation of Raf-1 in Alzheimer's disease," J Neurochem. 99(5): 1377-1388 (2006).
Menard et al., "Novel potent BRAF inhibitors: toward 1 nM compounds through optimization of the central phenyl ring," J Med Chem. 52(13): 3881-3891 (2009).
Mercer et al., "Emerging role of MAP kinase pathways as therapeutic targets in COPD," Int J Chron Obstruct Pulmon Dis. 1(2):137-150 (2006).
Messinger et al., "Synthesis of alpha-amino- and alpha-amidosulfones. 5. Sulfones as chemical transport forms of substances with germicidae effect," Arch Pharm (Weinheim). 307(8):653-5 (1974). (In German with partial English language translation).
Metzner et al., "Fibroblast growth factor receptors as therapeutic targets in human melanoma: synergism with BRAF inhibition," J Invest Dermatol. 131(10): 2087-2095 (2011).
Meyers et al., "FGFR2 exon IIIa and IIIc mutations in Crouzon, Jackson-Weiss, and Pfeiffer syndromes: evidence for missense changes, insertions, and a deletion due to alternative RNA splicing," Am J Hum Genet. 58(3):491-8 (1996).

(56) References Cited

OTHER PUBLICATIONS

Milella et al., "Therapeutic targeting of the MEK/MAPK signal transduction module in acute myeloid leukemia," J Clin Invest. 108(6): 851-859 (2001).
Mineo et al., "Prognostic impact of VEGF, CD31, CD34, and CD105 expression and tumour vessel invasion after radical surgery for IB-IIA non-small cell lung cancer," J Clin Pathol. 57(6):591-7 (2004).
Miura et al., "Simvastatin suppresses coronary artery endothelial tube formation by disrupting Ras/Raf/ERK signaling," Atherosclerosis. 175(2): 235-243 (2004).
Mohanta et al., "1-(methyldithiocarbony)imidazole: a useful thiocarbonyl transfer reagent for synthesis of substituted thioureas," Tetrahedron. 56(4):629-37 (2000).
Montagut et al.,"Elevated CRAF as a potential mechanism of acquired resistance to BRAF inhibition in melanoma," Cancer Res. 68(12): 4853-4861 (2008) (16 pages).
Moore et al., "ROMP-generated oligomeric sulfonyl chlorides as versatile soluble scavenging agents," Org Lett. 5(2)1 05-7 (2003).
Mukherjee et al., "Raf-1 expression may influence progression to androgen insensitive prostate cancer," Prostate. 64(1):101-107 (2005).
Mukhopadhyay et al., "Role of TNFalpha in pulmonary pathophysiology," Respir Res. 7:125 (2006) (9 pages).
Mustonen et al., "Endothelial receptor tyrosine kinases involved in angiogenesis," J Cell Biol. 129(4):895-8 (1995).
Nakamoto et al., "Diverse roles for the Eph family of receptor tyrosine kinases in carcinogenesis," Miscrosc Res Tech. 59(1):58-67 (2002).
Nakamura et al., "Novel strategies for the treatment of inflammatory bowel disease: Selective inhibition of cytokines and adhesion molecules," World J Gastroenterol. 12(29): 4628-4635 (2006).
Nazarian et al., "Melanomas acquire resistance to B-RAF(V600E) inhibition by RTK or N-RAS upregulation," Nature. 468(7326): 973-977 (2010) (7 pages).
O'Reilly et al., "Angiostatin: A novel angiogenesis inhibitor that mediates the suppression of metastases by a Lewis lung carcinoma," Cell. 79(2):315-28 (1994).
Oeztuerk-Winder et al., "The many faces of p38 mitogen-activated protein kinase in progenitor/stem cell differentiation," Biochem J. 445(1): 1-10 (2012).
Orre et al., "VEGF, VEGFR-1, VEGFR-2, microvessel density and endothelial cell proliferation in tumours of the ovary," Int J Cancer. 84(2)1 01-8 (1999).
Ozawa et al., "Growth factors and their receptors in pancreatic cancer," Teratog Carcinog Mutagen. 21(1):27-44 (2001).
Pabst et al., "Analysis of K-ras mutations in pancreatic tissue after fine needle aspirates," Anticancer Res. 19(4A):2481-3 (1999).
Palanisamy et al., "Rearrangements of the RAF kinase pathway in prostate cancer, gastric cancer and melanoma," Nat. Med. 16(7): 793-798 (2010) (7 pages).
Parlow et al., "Synthesis and crystal structures of substituted benzenes and benzoquinones as tissue factor Vlla inhibitors," J Med Chem. 46(20):4297-312 (2003).
Partanen et al., "A novel endothelial cell surface receptor tyrosine kinase with extracellular epidermal growth factor homology domains," Mol Cell Biol. 12(4):1698-707 (1992).
Partanen et al., "Functions of Tie1 and Tie2 receptor tyrosine kinases in vascular development," Curr Top Microbiol Immunol. 237:159-72 (1999).
Patani et al., "Bioisosterism: a rational approach to drug design," Chem Rev. 96(8):3147-76 (1996).
Paulson et al., "Receptor tyrosine kinases and the regulation of hematopoiesis," Semin Immunol. 7(4):267-77 (1995).
Payne et al., "Human papillomavirus type 6b virus-like particles are able to activate the RAS-MAP kinase pathway and induce cell proliferation," J Virol. 75(9): 4150-4157 (2001).
Peacock et al., "A novel angiogenesis inhibitor suppresses rat adjuvant arthritis," Cell Immunol. 160(2):178-84 (1995).
Peacock et al., "Angiogenesis inhibition suppresses collagen arthritis," J Exp Med. 175(4):1135-8 (1992).
Pelletier et al., "In vivo selective inhibition of mitogen-activated protein kinase kinase 1/2 in rabbit experimental osteoarthritis is associated with a reduction in the development of structural changes," Arthritis Rheum. 48(6): 1582-1593 (2003).
Peters, "Vascular endothelial growth factor and the angiopoietins working together to build a better blood vessel," Circ Res. 83(3):342-3 (1998).
Petrovan et al., "DNA vaccination against VEGF receptor 2 reduces atherosclerosis in LDL receptor-deficient mice," Arterioscler Thromb Vasc Biol. 27(5): 1095-1100 (2007) (11 pages).
Pinedo et al., "Translational research: the role of VEGF in tumor angiogenesis," The Oncologist. 5:1-2 (2000).
Planz et al., "MEK-specific inhibitor U0126 blocks spread of Borna disease virus in cultured cells," J Virol. 75(10): 4871-4877 (2001).
Pleschka et al., "Influenza virus propagation is impaired by inhibition of the Raf/MEK/ERK signalling cascade," Nat Cell Biol. 3(3): 301-305 (2001) (7 pages).
Plomp et al., "Pfeiffer syndrome type 2: further delineation and review of the literature," Am J Med Genet. 75(3):245-51 (1998).
Poulikakos et al., "RAF inhibitor resistance is mediated by dimerization of aberrantly spliced BRAF(V600E)," Nature. 480(7377): 387-390 (2011) (5 pages).
Poulikakos et al., "RAF inhibitors transactivate RAF dimers and ERK signalling in cells with wild-type BRAF," Nature. 464(7287): 427-430 (2010) (5 pages).
Powers et al., "Fibroblast growth factors, their receptors and signalling," Endocr Relat Cancer. 7(3):165-97 (2000).
Prakash et al., "A convenient synthesis of alpha-anilinoacetophenones using hypervalent iodine," Indian Journal of Chemistry, Section B: Organic Chemistry Including Medicinal Chemistry. 31:349-50 (1992).
Prix et al., "Diagnostic biochip array for fast and sensitive detection of K-ras mutations in stool," Clin Chem. 48(3):428-35 (2002).
Rajagopalan et al., "Tumorgenesis: RAF/RAS oncogenes and mismatch-repairs status," Nature. 418(6901):934 (2002).
Ramadas et al., "LAC sulfur assisted synthesis of symmetrical thioureas," Synth Comm. 27(13):2255-60 (1997).
Reck et al., "Novel N-linked aminopiperidine inhibitors of bacterial topoisomerase type II: broad-spectrum antibacterial agents with reduced hERG activity," J Med Chem. 54(22): 7834-7847 (2011).
Remli et al., "Reaction of o-arylenediamines with ethyl 3-fluoro 2-ketoesters synthesis of quinoxaline derivatives," J Fluorine Chem. 44: 15-23 (1989).
Riva et al., "Differential c-myc, c-jun, c-raf and p53 expression in squamous cell carcinoma of the head and neck: implication in drug and radioresistance," Eur J Cancer B Oral Oncol. 31B(6): 384-391 (1995).
Rotsos et al., "Cystoid macular edema," Clin Ophthalmol. 2(4): 919-930 (2008).
Rubinstein et al., "Incidence of the V600K mutation among melanoma patients with BRAF mutations, and potential therapeutic response to the specific BRAF inhibitor PLX4032," J Transl Med. 8: 67 (2010) (3 pages).
Rudy et al., "Zweikernige Alloxan-Abkömmlinge von 2.3-Diaminopyridinen," Chemische Berichte. 71:1323-1332 (1938) (Abstract Included) (11 pages).
Salama et al., "BRAF in Melanoma: Current strategies and future directions," Clin Cancer Res. 19(16): 4326-4334 (2013).
Sarkis et al., "Synthesis and spectroscopic properties of some new N,N'-disubstituted thioureas of potential biological interest," J Heterocyclic Chemistry. 22:137-40 (1985).
Schindler et al., "Analysis of BRAF V600E mutation in 1,320 nervous system tumors reveals high mutation frequencies in pleomorphic xanthoastrocytoma, ganglioglioma and extra-cerebellar pilocytic astrocytoma," Acta Neuropathol. 121(3): 397-405 (2011).
Schreck et al., "Raf kinases: Oncogenesis and drug discovery," Int J Cancer. 119(10): 2261-2271 (2006).
Search Report for British Application No. GB 0423554.5, dated Feb. 23, 2005 (1 page).
Search Report for British Application No. GB 0608268.9, dated Aug. 9, 2006 (1 page).
Search Report for British Application No. GB 0807609.3, dated Aug. 21, 2008 (2 pages).

(56) References Cited

OTHER PUBLICATIONS

Search Report for United Kingdom Application No. GB 1320729.5, dated May 20, 2014 (2 pages).
Search Report for United Kingdom Application No. GB 1320732.9, dated May 19, 2014 (2 pages).
Seki et al., "Reaction products of dialkyl acetylenedicarboxylates with 2,3-diaminopyridine," J Heterocyclic Chem. 32(3): 1071-1073 (1995).
Shakhov et al., "Kappa B-type enhancers are involved in lipopolysaccharide-mediated transcriptional activation of the tumor necrosis factor alpha gene in primary macrophages," J Exp Med. 171(1): 35-47 (1990).
Shapira et al., "Protection against endotoxic shock and lipopolysaccharide-induced local inflammation by tetracycline: correlation with inhibition of cytokine secretion," Infect Immun. 64(3): 825-828 (1996).
Shaw et al., "The preparation of 2,6-diaminopyrazine, 2,6-diazidopyrazine and some of their derivatives," J Heterocycl Chem. 17(1): 11-6 (1980).
Sherman et al., "Synthesis of unsymmetrical and regio-defined 2,3,6-quinoxaline and 2,3,7-pyridopyrazine derivatives," Tetrahedron Lett. 48(51):8943-8946 (2007).
Shi et al., "Melanoma whole-exome sequencing identifies (V600E)B-RAF amplification-mediated acquired B-RAF inhibitor resistance," Nat Commun. 3: 724 (2012) (8 pages).
Shibuya, "Vascular endothelial growth factor and its receptor system: physiological functions in angiogenesis and pathological roles in various diseases," J Biochem. 153(1):13-19 (2013).
Shiina et al., "A new method for the synthesis of carboxamides and peptides using 1,1'-carbonyldioxydi[2(1H)-pyridone] (CDOP) in the absence of basic promoters," Tetrahedron Letters. 44:1951-55 (2003).
Shin et al., "Expression of EphrinB2 identifies a stable genetic difference between arterial and venous vascular smooth muscle as well as endothelial cells, and marks subsets of microvessels at sites of adult neovascularization," Dev Biol. 230(2):139-50 (2001).
Sievert et al.,"Paradoxical activation and RAF inhibitor resistance of BRAF protein kinase fusions characterizing pediatric astrocytomas," Proc Natl Acad Sci USA. 110(15): 5957-5962 (2013) (9 pages).
Singer et al., "Mutations in BRAF and KRAS characterize the development of low-grade ovarian serous carcinoma," J Natl Cancer Inst. 95(6):484-6 (2003).
Smalley et al.,"CRAF inhibition induces apoptosis in melanoma cells with non-V600E BRAF mutations," Oncogene. 28(1): 85-94 (2009).
Smith et al.,"Vascular endothelial growth factor receptors VEGFR-2 and VEGFR-3 are localized primarily to the vasculature in human primary solid cancers," Clin Cancer Res. 16(14): 3548-3561 (2010).
Solit et al., "BRAF mutation predicts sensitivity to MEK inhibition," Nature. 439(7074):358-62 (2006).
Song et al.,"Activation of ERK/CREB pathway in spinal cord contributes to chronic constrictive injury-induced neuropathic pain in rats," Acta Pharmacol Sin. 26(7): 789-98 (2005).
Sosman et al., "Survival in BRAF V600-mutant advanced melanoma treated with vemurafenib," N Engl J Med. 366(8):707-714 (2012).
Srinivas et al., "A highly convenient, efficient, and selective process for preparation of esters and amides from carboxylic acids using Fe(3+)-K-10-montmorillonite clay," J Org Chem. 68(3):1165-7 (2003).
Srivastava et al., "Synthesis and antithyroid activity of some benzimidazolyl and benzenesulphonyl thiocarbamides" Current Science. 50(7):305-7 (1981).
Straussman et al., "Tumour micro-environment elicits innate resistance to RAF inhibitors through HGF secretion," Nature. 487(7408): 500-504 (2012) (7 pages).
Suijkerbuijk et al., "Development of novel, highly potent inhibitors of V-RAF murine sarcoma viral oncogene homologue B1 (BRAF): increasing cellular potency through optimization of a distal heteroaromatic group," J Med Chem. 53(7):2741-56 (2010).

Sullivan et al., "BRAF in melanoma: pathogenesis, diagnosis, inhibition, and resistance," J Skin Cancer. 2011:423239 (2011) (8 pages).
Suri et al., "Requisite role of angiopoietin-1, a ligand for TIE2 receptor, during embryonic angiogenesis," Cell. 87(7):1171-80 (1996).
Tam et al., "Blockade of VEGFR2 and not VEGFR1 can limit diet-induced fat tissue expansion: role of local versus bone marrow-derived endothelial cells," PLoS One. 4(3):e4974 (2009) (6 pages).
Tang et al., "Coexpression of transcripts encoding EPHB receptor protein tyrosine kinases and their ephrin-B ligands in human small cell lung carcinoma," Clin Cancer Res. 5(2):455-60 (1999).
Tang et al., "High-level expression of EPHB6, EFNB2, and EFNB3 is associated with low tumor stage and high TrkA expression in human neuroblastomas," Clin Cancer Res. 5(6):1491-6 (1999).
Tanga et al., "Syntheses of two potential food mutagens," J Heterocycl Chem. 40(4):569-73 (2003).
Taraboletti et al., "Inhibition of angiogenesis and murine hemangioma growth by batimastat, a synthetic inhibitor of matrix metalloproteinases," J Natl Cancer Inst. 87(4):293-8 (1995).
Temple et al., "New anticancer agents: alterations of the carbamate group of ethyl (5-amino-1,2-dihydro-3-phenylpyrido[3,4-b]pyrazin-7-yl)car bamates," J Med Chem. 32(10):2363-7 (1989).
Terao et al., "Synthesis of .alpha.-thio, .alpha.-sulfinyl, and .alpha.-sulfonyl-substituted nitrosamines," Chem Pharm Bull. 25(11):2964-8 (1977).
Thalhamer et al., "MAPKs and their relevance to arthritis and inflammation," Rheumatology (Oxford). 47(4):409-414 (2008).
Thornber, "Isosterism and molecular modification in drug design," Chem Soc Rev. 8(4):563-80 (1979).
Uchida et al., "Studies on 2(1H)-quinolinone derivatives as gastric antiulcer active agents. 2-(4-chlorobenzoylamino)-3-[2(1H)-quinolinon-4-yl]propionic acid and related compounds," Chem Pharm Bull (Tokyo). 33(9):3775-86 (1985).
Vergani et al., "Identification of MET and SRC activation in melanoma cell lines showing primary resistance to PLX4032," Neoplasia. 13(12):1132-1142 (2011) (14 pages).
Villanueva et al., "Acquired resistance to BRAF inhibitors mediated by a RAF kinase switch in melanoma can be overcome by cotargeting MEK and IGF-1R/PI3K," Cancer Cell. 18(6):683-695 (2010) (34 pages).
Wan et al., "Mechanism of activation of the RAF-ERK signaling pathway by oncogenic mutations of B-RAF," Cell. 116(6):855-67 (2004).
Wang et al., "Antisense targeting of basic fibroblast growth factor and fibroblast growth factor receptor-1 in human melanomas blocks intratumoral angiogenesis and tumor growth," Nat Med. 3(8): 887-93 (1997).
Wang et al., "Inhibition of MEK/ERK 1/2 pathway reduces proinflammatory cytokine interleukin-1 expression in focal cerebral ischemia," Brain Res. 996(1):55-66 (2004).
Wang et al., "Molecular distinction and angiogenic interaction between embryonic arteries and veins revealed by ephrin-B2 and its receptor Eph-B4", Cell. 93(5):741-53 (1998).
Wang et al., "Significant neuroprotection against ischemic brain injury by inhibition of the MEK1 protein kinase in mice: exploration of potential mechanism associated with apoptosis," J Pharmacol Exp Ther. 304(1): 172-178 (2003).
Ward et al., "Targeting oncogenic Ras signaling in hematologic malignancies," Blood. 120(17): 3397-3406 (2012).
Wellbrock et al., "The RAF proteins take centre stage," Nat Rev Mol Cell Biol. 5(11):875-85 (2004).
Wellbrock et al., "V599EB-RAF is an oncogene in melanocytes," Cancer Res. 64(7): 2338-2342 (2004) (6 pages).
Whittaker et al., "A novel, selective and efficacious nanomolar pyridopyrazinone inhibitor of V600EBRAF," Cancer Res. 70(20): 8036-8044 (2010) (13 pages).
Wilks, "Structure and function of the protein tyrosine kinases," Prog Growth Factor Res. 2(2):97-111 (1990).
Wilson et al., "Widespread potential for growth-factor-driven resistance to anticancer kinase inhibitors," Nature. 487(7408): 505-509 (2012) (6 pages).

(56) References Cited

OTHER PUBLICATIONS

Xing, "Molecular pathogenesis and mechanisms of thyroid cancer," Nat Rev Cancer. 13(3):184-199 (2013).

Yancopoulos et al., "Vasculogenesis, angiogenesis and growth factors: ephrins enter the fray at the border," Cell. 93(5):661-4 (1998).

Yang et al., "Regulation of human immunodeficiency virus type 1 infectivity by the ERK mitogen-activated protein kinase signaling pathway," J Virol. 73(4):3460-3466 (1999).

Yao et al., "Lipopolysaccharide induction of the tumor necrosis factor-alpha promoter in human monocytic cells. Regulation by Egr-1, c-Jun and NF-kappaB transcription factors," J Biol Chem. 272(28): 17795-17801 (1997).

Yeatman, "A renaissance for SRC," Nat Rev Cancer. 4(6):470-480 (2004).

Young et al., "Ras signaling and therapies," Adv Cancer Res. 102:1-17 (2009).

Yu et al., "Loss of fibroblast growth factor receptor 2 ligand-binding specificity in Apert syndrome," Proc Natl Acad Sci U.S.A. 97(26):14536-41 (2000).

Zambon et al., "Novel hinge binder improves activity and pharmacokinetic properties of BRAF inhibitors," J Med Chem. 53(15):5639-55 (2010).

Zejc et al., "Synthesis and anticonvulsant properties of some arylsuccinate methylpyridylimides", Pol J Pharmacol Pharm. 42(1):69-77 (1990).

Zhang et al., "Activation of the Ras/Raf/MEK pathway facilitates hepatitis C virus replication via attenuation of the interferon-JAK-STAT pathway," J Virol. 86(3): 1544-1554 (2012).

Zhang et al., "Targeting Src family kinases in anti-cancer therapies: turning promise into triumph," Trends Pharmacol Sci. 33(3): 122-128 (2012).

Zhou et al.,"Synthesis and SAR of 5-, 6-, 7- and 8-aza analogues of 3-aryl-4-hydroxyquinolin-2(1H)-one as NMDA/glycine site antagonists," Bioorg Med Chem. 9(8):2061-71 (2001).

Ziegler et al.,"Some 9-Aza-alloxazines," J Am Chem Soc. 71:1891-1893 (1949).

Zouki et al.,"Peroxynitrite induces integrin-dependent adhesion of human neutrophils to endothelial cells via activation of the Raf-1/MEK/Erk pathway," FASEB J. 15(1):25-27 (2001).

\* cited by examiner

1-(5-TERT-BUTYL-2-ARYL-PYRAZOL-3-YL)-3-[2-FLUORO-4-[(3-OXO-4H-PYRIDO [2,3-B]PYRAZIN- 8-YL)OXY]PHENYL]UREA DERIVATIVES AS RAF INHIBITORS FOR THE TREATMENT OF CANCER

RELATED APPLICATION

This application is related to: United Kingdom patent application number 1320729.5 filed 25 Nov. 2013, the contents of which are incorporated herein by reference in their entirety.

TECHNICAL FIELD

The present invention pertains generally to the field of therapeutic compounds.

More specifically the present invention pertains to certain 1-(5-tert-butyl-2-aryl-pyrazol-3-yl)-3-[2-fluoro-4-[(3-oxo-4H-pyrido[2,3-b]pyrazin-8-yl)oxy]phenyl]urea compounds (referred herein as "TBAP compounds") that, inter alia, inhibit RAF (e.g., BRAF, CRAF, etc.).

The present invention also pertains to pharmaceutical compositions comprising such compounds, and the use of such compounds and compositions, both in vitro and in vivo, to inhibit RAF (e.g., BRAF, CRAF, etc.); and to treat disorders including: proliferative disorders; cancer (including, e.g., malignant melanoma, colorectal carcinoma, pancreatic adenocarcinoma); inflammation; immunological disorders; viral infections; fibrotic disorders; disorders associated with a mutated form of RAF (e.g., BRAF, CRAF, etc.); disorders ameliorated by the inhibition of RAF (e.g., BRAF, CRAF, etc.); disorders ameliorated by the inhibition of mutant BRAF; disorders ameliorated by the inhibition of BRAF and CRAF; disorders associated with RAS mutations and/or MAPK pathway activation; disorders ameliorated by the inhibition of SRC, p38, FGFRA, VEGFR-2 (KDR), and/or LCK; etc.

BACKGROUND

A number of publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

RAF, Proliferative Disorders, and Cancer

Mutations in genes that directly or indirectly control cell growth and differentiation are generally considered to be the main cause of cancer. Malignant tumours develop through a series of stepwise, progressive changes that lead to the loss of growth control characteristic of cancer cells, i.e., continuous unregulated proliferation, the ability to invade surrounding tissues, the ability to metastasize to different organ sites, stimulation of angiogenesis, resistance to apoptosis, the ability to evade the immune system, abnormal metabolic pathways, and local inflammation. Carefully controlled in vitro studies have helped define the factors that characterize the growth of normal and neoplastic cells and have led to the identification of specific proteins that control cell growth and differentiation.

RAF is a key downstream target for the RAS Guanine-nucleotide binding/GTPase proteins and mediates the activation of the MAP kinase cascade consisting of RAF-MEK-ERK. Activated ERK is a kinase that subsequently targets a number of proteins responsible for mediating, amongst other things, the growth, survival, and transcriptional functions of the pathway. These include the transcription factors ELK1, C-JUN, the Ets family (including Ets 1, 2, and 7), and the FOS family. The RAS-RAF-MEK-ERK signal transduction pathway is activated in response to many cell stimuli including growth factors such as EGF, PDGF, KGF, etc. Because the pathway is a major target for growth factor action, the activity of RAF-MEK-ERK has been found to be up-regulated in many factor-dependent tumours. The observation that about 20% of all tumours have undergone an activating mutation in one of the RAS proteins indicates that the pathway is more broadly important in tumourigenesis.

The RAF oncogene family includes three highly conserved genes termed ARAF, BRAF and CRAF (also called Raf-1). RAF genes encode protein kinases that are thought to play important regulatory roles in signal transduction processes that regulate cell proliferation. RAF genes code for highly conserved serine-threonine-specific protein kinases, which are recruited to the plasma membrane following direct binding to RAS, which is the initiating event in RAF activation. RAF proteins are part of a signal transduction pathway believed to consist of receptor tyrosine kinases, p21 RAS, RAF, Mek1 (ERK activator or MAPKK) kinases and ERK (MAPK) kinases, which ultimately phosphorylate several cellular substrates, including transcription factors. Signalling through this pathway can mediate differentiation, proliferation, or oncogenic transformation in different cellular contexts. Thus, RAF kinases are believed to play a fundamental role in the normal cellular signal transduction pathway, coupling a multitude of growth factors to their net effect, cellular proliferation. Because RAF proteins are direct downstream effectors of RAS protein, therapies directed against RAF kinases are believed to be useful in treatment of RAS-dependent tumours.

The RAF kinases are differentially regulated and expressed. CRAF is expressed in all organs and in all cell lines that have been examined. ARAF and BRAF also appear to be ubiquitous, but are most highly expressed in urogenital and brain tissues, respectively. Because BRAF is highly expressed in neural tissues it was once thought to be limited to these tissues but it has since been found to be more widely expressed. Although all RAF proteins can bind to active RAS, BRAF is most strongly activated by oncogenic RAS.

BRAF is important in cancer, because it is mutated in about half of malignant melanomas and thyroid papillary carcinomas, 30% of low-grade ovarian cancer, 15% of colon cancers, and with very high frequency in hairy cells leukaemia, as well as occurring at lower frequencies in a number of other cancers, totalling 7% of human cancers. See, e.g., http://www.sanger.ac.uk/genetics/CGP/cosmic/. A specific subtype of pancreatic cancers, KRAS2 wild-type medullary carcinoma of the pancreas, presents BRAF mutations in 30% of samples (see, e.g., Calhoun et al., 2003). In contrast, ARAF and CRAF mutations are very rare in human cancer.

TABLE 1

Frequency of BRAF Mutations in Different Types of Cancers

| Tumour Type | Frequency | Citation |
|---|---|---|
| Malignant Melanoma | 50% | |
| Papillary Thyroid Cancer (PTC) | | Xing, 2013 |
| Conventional PTC) | 45% | |
| Follicular-variant PTC | 15% | |
| Tall-cell PTC | 80-100% | |
| Anaplastic Thyroid Cancer | 25% | |
| Colorectal carcinoma | 15% | |
| Low grade ovarian carcinomas | 30% | |
| Hairy Cells Leukemia | 100% | Arcaini et al., 2012 |
| Cholangiocarcinoma | 15% | |
| Nervous system tumours | 7% | Schindler et al., 2011 |
| Pilocytic astrocytomas | 9% | |
| Ganglioglioma | 18% | |
| Pleomorphic xanthoastrocytoma | 66% | |
| Multiple myeloma | 4% | Chapman et al., 2011 |
| Non-Small Cell Lung Cancer | 1-3% | |
| Medullary carcinoma of the pancreas | 30% | |
| Frequency of BRAF Mutations in Other diseases | | |
| Histiocytosis | | |
| Langerhans cell histiocytosis | 57% | Badalian-Very et al., 2011 |
| Erdheim-Chester disease | 54% | Haroche et al., 2012 |

Over 100 different mutations have been described in BRAF in cancer, but a single mutation (a glutamic acid (E) substitution for the valine (V) at position 600) accounts for about 80% of total BRAF mutations in cancer. This mutant activates BRAF 500-fold, and allows it to stimulate constitutive ERK and NFkB signalling, stimulating survival and proliferation. Consequently, $^{V600E}$BRAF can transform cells such as fibroblasts and melanocytes. Inhibition of $^{V600E}$BRAF in cancer cells inhibits cell proliferation and induces apoptosis in vitro; in vivo, it suppresses tumour cell growth, validating $^{V600E}$BRAF as a therapeutic target.

Other V600 BRAF mutations identified in melanoma are V600K, V600D and V600R (see, e.g., Davies et al., 2002; Wan et al., 2004; Long et al., 2011; Rubinstein et al., 2010). A minor sub-group of melanomas were also identified with BRAF mutations in positions other than 600. These non-V600 position BRAF mutants do not necessarily activate BRAF kinase activity directly, but require the presence of CRAF to transactivate their MAPK signaling (see, e.g., Smalley et al., 2009). In such cases, inhibition of RAF activity would remain a beneficial aim in cancer treatment.

Importantly, it has been shown that drugs that inhibit mutant BRAF such as vemurafenib (PLX4032, RG7204, Zelboraf) (see, e.g., Flaherty et al., 2010) and dabrafenib (GSK-2118436) (see, e.g., Falchook et al., 2012) can mediate impressive responses in patients whose tumours express oncogenic BRAF (reviewed in Salama et al., 2013). In particular, vemurafenib has shown promising results in mutant BRAF driven melanoma (see, e.g., Chapman et al., 2011; Sosman et al., 2012). It was approved in 2011 by the USA Food and Drug Administration (FDA) for the treatment of V600E BRAF mutant late stage metastatic or unresectable melanoma, and in 2012 by the European Medicines Agency (EMA) as monotherapy for the treatment of adult patients with any BRAF V600 mutation-positive unresectable or metastatic melanoma. Dabrafenib was approved by FDA and EMA in 2013 for the same indication.

These data validate mutant BRAF as a therapeutic target in melanoma and a potential target for other cancers and proliferative diseases where BRAF is mutated. This and other evidence suggests that inhibition of RAF (e.g., BRAF) activity would be beneficial in the treatment of cancer, and that inhibition of RAF (e.g., BRAF) activity could be particularly beneficial in those cancers containing a constitutively activated BRAF mutation.

Resistance to BRAF Inhibitors

Despite being able to mediate significant clinical responses, most patients treated with vemurafenib and dabrafenib eventually progress on treatment (see e.g., Flaherty et al., 2010; Sosman et al., 2012) due to the acquisition of resistance that can be mediated by several mechanisms (see, e.g., Sullivan et al., 2011). Furthermore, about 30% of patients present with primary resistance and do not respond despite the presence of a BRAF mutation (see, e.g., Chapman et al., 2011).

Mutations in KRAS (G12S, G12V, G12D, G12A, G12C, G13A, G13D) have been suggested as predictive markers for identifying tumours that are not susceptible to mutant BRAF inhibitor treatment (see, e.g., Hatzivassiliou et al., 2011). The Q16K mutation of NRAS confers resistance to BRAF inhibitor vemurafenib (see, e.g., Nazarian et al., 2010). Similarly, resistance to treatment with the BRAF inhibitor dabrafenib is predicted by the Q16K and A146T mutations of the NRAS protein (see, e.g., Greger et al., 2012). Activation of RAS through mutations lead to an increase in RAF dimerisation (formation of heterodimer of CRAF with the BRAF protein and/or CRAF/BRAF homodimer) with increased signalling through the MAPK cascade and increased cell proliferation (see, e.g., Poulikakos et al. 2010).

Up-regulation of (and mutations in) CRAF is another mechanism of resistance seen in resistant melanomas treated with BRAF inhibitors (see, e.g., Heidorn et al., 2010; Montagut et al., 2008; Antony et al. 2013). panRAF inhibitors of multiple RAF isoforms (BRAF and CRAF especially) are likely therefore to have an enhanced effect in RAS-mutated melanomas and other RAS mutated cancers, and to address one key resistance mechanism to selective BRAF inhibitors.

Copy number gain of the BRAFV600E gene is associated with BRAF inhibitor resistance in BRAF-mutant melanoma (see, e.g., Shi et al., 2012) and colorectal carcinoma (see, e.g., Corcoran et al., 2010). Both these models are sensitive to concomitant inhibition of BRAF and MEK, but only amplified BRAF-mutant melanoma is sensitive to MEK inhibitor alone. This mechanism of resistance is likely to be more sensitive to panRAF inhibition than to BRAF-only inhibition.

In some melanomas, resistance to vemurafenib was acquired via the expression of splice variant isoforms of BRAFV600E. A 61 kDa splice variant of BRAFV600E (p61BRAFV600E) lacked exons 4-8 encoding the RAS binding domain, and was resistant to vemurafenib. p61BRAFV600E is constitutively dimerised in the absence of activated RAS. Dimerization of p61BRAFV600E was shown to be critical for mediating BRAF inhibitor resistance (see, e.g., Poulikakos et al., 2011).

BRAF and CRAF gene fusion is an alternative mechanism of MAPK pathway activation. These activating gene fusion products have been identified in prostate cancer, gastric cancer and melanoma (SLC45A3-BRAF and ESRP1-RAF1) (see, e.g., Palanisamy et al., 2010), thyroid cancers (AKAP9-BRAF) (see, e.g., Ciampi et al., 2005) and pediatric astrocytomas (KIAA1549-BRAF) (see, e.g., Sievert et al., 2013). Some of the models expressing RAF fusions (for example SLC45A3-BRAF) are sensitive to BRAF and MEK inhibition; in contrast, the KIAA1549-BRAF model is resistant to PLX4720, but is sensitive to a second generation BRAF inhibitor.

Kinase suppressor of Ras (KSR) is a conserved positive modulator of the RAS-RAF-MEK-ERK pathway. KSR1 interacts constitutively with MEK and is known to play an important role in co-localizing MEK with RAF at the plasma membrane. KSR1 is involved in the MAPK pathway activation by BRAF inhibitors in RAS-mutant or activated RAS cells (see, e.g., McKay et al., 2011). Two mechanisms of drug activation of the pathway have been proposed. One mechanism involves formation of CRAF-KSR1 dimer, complex formation with MEK and MEK phosphorylation by the KSR1-CRAF dimer (see, e.g., Hu et al., 2011). In the other mechanism, KSR1 dimerises with BRAF, and compete with the BRAF-CRAF heterodimer which is the driver of MEK phosphorylation. It was suggested that RAS activated cells with lower expression of KSR1 will show more paradoxical pathway activation (see, e.g., McKay et al., 2011). In both mechanisms, panRAF inhibitors are likely to reduce pathway activation irrespective of KSR1 level of expression.

Overexpression of receptor tyrosine kinases (RTKs) is another mechanism of resistance to BRAF inhibitors. Overexpression of EGFR (epidermal growth factor receptor) leads to EGFR-mediated MAPK pathway reactivation and resistance to vemurafenib in BRAF-mutant colorectal cancers (see, e.g., Corcoran et al., 2012). In drug-resistant BRAF-mutant melanoma cell lines, EGFR-SFK-STAT3 signalling can mediate resistance to BRAF inhibitors in vitro and in vivo, in melanoma (see, e.g., Girotti et al., 2013). Src Family kinases SFKs play a key role in mediating resistance to BRAF inhibitors in melanoma cells (see, e.g., Girotti et al., 2013; Vergani et al., 2011). Elevated phosphorylation of the SFKs LYN, YES and FYN is observed in the vemurafenib-resistant lines. The growth of resistant cells is sensitive to SFK inhibition: Dasatinib and depletion of SRC and LYN both suppressed invasion of the resistant cells in vitro. Of critical importance, SFK signalling was increased in a tumour from a patient with intrinsic resistance to vemurafenib, and dasatinib inhibited the growth and metastasis of this tumour in mice.

Corcoran et al., 2012, "EGFR-mediated reactivation of MAPK signaling contributes to insensitivity of BRAF-mutant colorectal cancers to RAF inhibition with vemurafenib", *Cancer Discovery*, Vol. 2, pp. 227-235.

PDGFR-β was found to be overexpressed and hyperphosphorylated in mutant BRAF cell lines resistant to vemurafenib, and upregulated in several cases of vemurafenib-resistant tumours from patients, suggesting that this mechanism may be clinically relevant (see, e.g., Nazarian et al., 2010). Up-regulation of PDGFR-3 may drive resistance by activating other ERK1/2-independent downstream pathways (PI3K, PLCγ).

Mechanistic studies showed IGFR1 signalling to mediate increased PI3K/AKT signaling in cells that acquired BRAF inhibitors resistance and that the resistance could be reversed by treating the cells with the combination of a PI3K and a MEK inhibitor or an IGF1R and a MEK inhibitor (see, e.g., Villanueva et al., 2011). The translational relevance of this finding was confirmed by the observation that 1 out of 5 melanoma specimens from patients failing vemurafenib expressed increased levels of IGFR1 (see, e.g., Villanueva et al., 2011).

Growth factor upregulation by the stroma is a mechanism of resistance. A significant correlation has been shown between stromal cell expression of HGF in patients with BRAF-mutant melanoma and innate resistance to RAF inhibitor treatment (see, e.g., Wilson et al., 2012). cMET and/or their ligands are claimed as predictive markers for identifying tumours that are not susceptible to BRAF inhibitor (see, e.g., Hatzivassiliou et al., 2011; Straussman et al., 2012). Dual inhibition of RAF and either HGF or MET resulted in reversal of drug resistance, suggesting RAF plus HGF or MET inhibitory combination therapy as a potential therapeutic strategy (see, e.g., Hatzivassiliou et al., 2011; Straussman et al., 2012).

FGFR1 is implicated in melanoma progression, and knockdown of FGFR1 results in inhibition of melanoma growth in vivo (see, e.g., Wang et al., 1997). Fibroblast growth factor (FGF) rescues some BRAF mutant cells from treatment with PLX4032 (see, e.g., Wilson et al., 2012) and FGFR1 inhibition is synergistic with multikinase/BRAF inhibitor sorafenib and specific BRAF inhibitor RG7204 (see, e.g., Metzner et al., 2012). These findings suggest that inhibition of RTKs such as EGFR, PDGFR-β, HGFR, IGF1R and FGFR, and of SFKs should target a number of resistance mechanisms to selective BRAF inhibitors and consequently be of utility in BRAF mutant tumours that become resistant to BRAF-selective inhibitors.

Cancer and RAS

RAS proteins are small-guanine nucleotide binding proteins that are downstream of growth factor, cytokine and hormone receptors. These cell surface receptors activate proteins called guanine-nucleotide exchange factors (GNEFs), which replace GDP for GTP on RAS proteins, stimulating RAS activation. Other proteins called GTPase-activating proteins (GAPs) stimulate the intrinsic GTPase activity of RAS, thereby promoting GTP hydrolysis and returning RAS to its inactive GDP-bound state. Activated RAS binds to several effector proteins, including phosphoinositide 3-kinase (PI3K), the RAF family of protein kinases, and the Ral guanine-nucleotide exchange factor. These effectors in turn regulate the activity of the signalling pathways that control cell proliferation, senescence, survival, and differentiation. There are three RAS genes in mammals called HRAS, KRAS and NRAS and they serve overlapping but non-conserved functions.

RAS proteins are also important in cancer. 20-30% of human tumours harbour somatic gain-of-function mutations in one of the RAS genes. Most commonly these involve the codons for glycine 12 (G12), glycine 13 (G13) and glutamine 61 (Q61) and these mutations impair, through different mechanisms, the GAP-stimulated intrinsic GTPase activity of RAS, trapping it in the active GTP-bound state and allowing it to promote tumourigenesis. See, e.g., Downward et al., 2003; Young et al., 2009; Bos et al., 1989.

TABLE 2

Frequency of RAS Mutations in Different Types of Cancers

| Tumour Type | Frequency | Citation |
| --- | --- | --- |
| Pancreas | 90% | |
| Thyroid (Undifferentiated papillary) | 60% | |
| Thyroid (Follicular) | 55% | |
| Colorectal | 45% | |
| Seminoma | 45% | |
| Lung adenocarcinoma (non-small-cell) | 35% | |
| Liver | 30% | |
| Haematologic malignancies: | | Ward et al., 2012 |
| Acute myelogenous leukemia (AML) | 16% | |
| Juvenile myelomonocytic leukemia (JMML) | 25% | |
| Chronic myelomonocytic leukemia (JMML) | 30% | |
| Myelodisplastic syndrome (MDS) | 6% | |
| Acute lymphoblastic leukemia (ALL) | 14% | |
| Multiple Myeloma (MM) | 26% | |
| Burkitt's lymphoma | 10% | |
| Hodgkin's lymphoma | 16% | |
| Malignant Melanoma | 20% | |
| Bladder Transitional Cell carcinoma | 12% | Fernandes-Medarde, 2011 |
| Kidney | 10% | |
| Epithelial ovarian cancers | 11% | www.mycancergenome.org |
| Low grade serous (Type I) | 33% | |
| Mucinous (Type I) | 50-75% | |
| Endometrial cancers | 0-46% | Mammas et al., 2005 |
| Cervical cancer | 0-61% | Mammas et al., 2005 |
| Biliary tract adenocarcinoma | 35% | Fernandes-Medarde, 2011 |
| Soft tissue sarcoma* | | Fernandes-Medarde, 2011 |
| Angiosarcoma | 49% | |
| Leiomyosarcoma | 8% | |
| Rhabdomyosarcoma | 11% | |
| Myxoma | 11% | |
| Malignant fibrous histiocytoma | 16% | |

*The most frequently mutated RAS quoted (KRAS or NRAS or HRAS).

Other cancers have less frequent mutations of the RAS family genes, but their mutation is predictive of prognosis, for example neuroblastoma (8% NRAS mutation), stomach adenocarcinoma (6% KRAS mutant).

RAS and RAF

Active RAS proteins activate several downstream effectors, including the proteins of the RAF family. There are three RAF proteins, ARAF, BRAF and CRAF. Activated RAF phosphorylates and activates a second protein kinase called MEK, which then phosphorylates and activates a third protein kinase called ERK. ERK phosphorylates a multitude of cytosolic and nuclear substrates, thereby regulating cell processes such as proliferation, survival, differentiation and senescence.

Notably, however, in cancer cells, oncogenic RAS does not signal through BRAF, but instead signals exclusively through CRAF to activate MEK.

In the vast majority of cancers, BRAF and RAS mutations are mutually exclusive. This provides genetic evidence to suggest that these proteins are on the same pathway and that they drive the same processes in cancer cells. However, there are clear differences between oncogenic BRAF and oncogenic RAS functions in cancer cells. First, RAS activates several pathways, whereas BRAF is only known to activate the MEK/ERK pathway. As a consequence, BRAF mutant cells are more dependent on MEK/ERK signalling and so are considerably more sensitive to BRAF or MEK inhibitors than cell in which RAS is mutated. See, e.g., Garnett et al., 2004; Wellbrock et al., 2004; Gray-Schopfer et al., 2007; Solit et al., 2006.

Apart from mutations, signalling proteins in the MAPK cascade are overexpressed in a number of malignancies. For example, HRAS and NRAS are overexpressed in cervical cancers. RAS mutations are rare in adrenocortical carcinoma, but the collective population of tumours with mutations in RAS, BRAF and EGFR show increased signalling through the pathway and can be a target for MAPK pathway inhibitors (see, e.g., Kotoula et al., 2009). Low grade ovarian cancers and peritoneal cancer respond to blockage of the MAPK pathway with MEK inhibitor selumetinib independent of the RAS/RAF mutation status. In uveal melanoma, the MAPK pathway is activated through the mutation of GNAQ which accounts for 50% of uveal melanomas (see, e.g., Gaudi et al., 2011). cRAF is overexpressed in a variety of primary human cancers, such as lung, liver, prostate, primitive neurodermal tumours, head and neck squamous cell carcinoma (see, e.g., Damodar Reddy et al., 2001; Hwang et al., 2004; Mukterjee et al., 2005; Schreck et al., 2006; Riva et al., 1995). The MAPK pathway is activated in 74% of acute myeloid leukemia patients samples (see, e.g., Milella et al., 2001). In neurofibromatosis type 1, loss of NF1 tumour suppressor gene leads to hyperactivated RAS signalling, and deregulated Ras/ERK signalling which is critical for the growth of NF1 peripheral nerve tumours (see, e.g., Jessen et al., 2013). A panRAF inhibitor elicit an effective blockade of the MAPK pathway for BRAF mutant tumours and for RAS mutant tumours and has broad application for cancers with deregulation of the MAPK signalling pathway.

Cancers with activating mutations of RAS, RAF and EGFR or over expression of RAS, RAF and EGFR including any of the isoforms thereof, may be therefore particularly sensitive to panRAF (e.g., CRAF and BRAF) inhibition. Cancers with other abnormalities leading to an upregulated RAF-MEK-ERK pathway signal may also be particularly sensitive to treatment with inhibitors of panRAF (e.g., CRAF and BRAF) activity. Examples of such abnormalities include constitutive activation of a growth factor receptor;

overexpression of one or more growth factor receptors; overexpression of one or more growth factors; KSR-mediated pathway activation; and BRAF or CRAF gene fusions.

MAPK Pathway in Other Diseases

The RAF-MEK-ERK pathway functions downstream of many receptors and stimuli indicating a broad role in regulation of cell function. For this reason, inhibitors of RAF may find utility in other disease conditions that are associated with up-regulation of signalling via this pathway. The RAF-MEK-ERK pathway is also an important component of the normal response of non-transformed cells to growth factor action. Therefore, inhibitors of RAF may be of use in diseases where there is inappropriate or excessive proliferation of normal tissues. These include, for example, glomerulonephritis and psoriasis.

The function of inflammatory cells is controlled by many factors, the effects of which are mediated by different signal transduction pathways. Although some key pro-inflammatory functions are mediated by p38 Map kinase (e.g., TNF release), others are mediated by other pathways. The RAF-MEK-ERK pathway, in particular, is an important activating and proliferative signal in many inflammatory cells. B and T lymphocytes, in particular, require activation of the RAF-MEK-ERK pathway for clonal expansion and generation of effector populations (see, e.g., Cantrell, 2003; Genot et al., 2000). The cellular signalling pathway of which RAF is a part has been implicated in inflammatory disorders characterized by T-cell proliferation (T-cell activation and growth), such as tissue graft rejection, endotoxin shock, and glomerular nephritis.

Activation of the MAPK/ERK signalling has been demonstrated in many models of disease models, and inhibition of the pathway, using for example MEK inhibitors, have been shown to be potentially beneficial in these various diseases such as:

Pain: Evidence of Efficacy in Pain Models: MEK pathway is upregulated in dorsal horn neurons in persistent pain (see, e.g., Ji et al., 2002; Song et al., 2005; Ma et al., 2005; Karim et al., 2006); Mek inhibitors in neuropathic pain (see, e.g., Dixon et al., 2001).

Stroke: Evidence of Efficacy in Stroke Models Significant Neuroprotection against Ischemic Brain Injury by Inhibition of the MEK (see, e.g., Wang et al., 2003; Wang et al., 2004; Maddahi et al., 2010).

Diabetes: Evidence In Diabetic Complications (see, e.g., Fujita et al., 2004).

Inflammation: Evidence of Efficacy in Inflammation Models (see, e.g., Jaffee et al., 2000; Thalhamer et al., 2008; Geppert et al., 1994).

Arthritis: Evidence of efficacy in experimental osteoarthritis (see, e.g., Pelletier et al., 2003); model of rheumatoid arthritis (see, e.g., Chun et al., 2002; Dudley et al., 2000); reviewed in Thalhamer et al., 2008.

Heart remodelling, for example, in metabolic syndrome (see, e.g., Asrih et al., 2013).

Organ injury, for example, in cisplatin-induced renal injury (see, e.g., Jo et al., 2005).

Haemoglobinopathies: sickle-cell disease, β-thalassemia, haemoglobin H disease (see, e.g., Zennadi et al., 2012).

Asthma (see, e.g., Bridges et al., 2000).

Transplant rejection (see, e.g., Gilbertsen et al., 2000).

Septic shock (see, e.g., Geppert et al., 1994).

Viral infection, for example hepatitis B (see, e.g., Benn et al., 1994), hepatitis C (see, e.g., Zhang et al., 2012), human immunodeficiency virus (HIV) (see, e.g., Yang et al., 1999), Epstein-Barr virus (EBV) (see, e.g., Fukuda et al., 2007), HPV (see, e.g., Payne et al., 2001), human herpesvirus-8 (HHV) associated with Kaposi sarcoma (see, e.g., Akula et al., 2004), human cytomegalovirus (see, e.g., Johnson et al., 2001), Coxsackievirus B3 (see, e.g., Luo et al., 2002), Borna virus (see, e.g., Planz et al., 2001), influenza virus (see, e.g., Pleschka et al., 2001).

chronic infections and autoimmune diseases, for example, by inhibiting regulatory T-cells activity (see, e.g., Kjetil et al., 2013).

Atherosclerosis (see, e.g., Miura et al., 2004).

Restenosis (see, e.g., Graf et al., 1997).

Cardiomyopathy (see, e.g., Lorenz et al., 2009).

Cardiac ischemia reperfusion injury (see, e.g., Zouki et al., 2000).

Psoriasis (see, e.g., Haase et al., 2001).

Alzheimer's disease (see, e.g., Mei et al., 2006) and other induced neurological disorders such as HTLV-I-associated myelopathy/tropical spastic parasite or neurodegenerative diseases such as Parkinson's disease or Amyloid Lateral Sclerosis via CD44 splice-variants modulation (see, e.g., Pinner et al., 2009).

Chronic obstructive pulmonary disorder (see, e.g., Mercer et al., 2006).

Inflammatory bowel disease (see, e.g., Lowenberg et al., 2005).

Fibrogenetic diseases, such as cystic fibrosis (see, e.g., Li et al., 1998), liver fibrosis, for example, liver cirrhosis (see, e.g., Davies et al., 1996).

Hereditary RAS mutations lead to a group of diseases named collectively as rasopathy. Targeting the MAPK pathway in these diseases has been proposed as a therapeutic approach in these type of diseases such as Noonan Syndrome (see, e.g., Gu et al., 2013), Cardiofaciocutaneous Syndrome (see, e.g., Anastasaki et al., 2012) and capillary malformations (see, e.g., Vikkula et al., 2004).

RTKs

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity that leads to phosphorylation of tyrosine residues on both the receptor and other intracellular proteins, leading to a variety of cellular responses. To date, at least nineteen distinct RTK subfamilies, defined by amino acid sequence homology, have been identified.

FGFR

The fibroblast growth factor (FGF) family of signaling polypeptides regulates a diverse array of physiologic functions including mitogenesis, wound healing, cell differentiation and angiogenesis, and development. Both normal and malignant cell growth as well as proliferation are affected by changes in local concentration of these extracellular signalling molecules, which act as autocrine as well as paracrine factors. Autocrine FGF signalling may be particularly important in the progression of steroid hormone-dependent cancers and to a hormone independentstate (see, e.g., Powers et al., 2000).

FGFs and their receptors are expressed at increased levels in several tissues and cell lines and overexpression is believed to contribute to the malignant phenotype. Furthermore, a number of oncogenes are homologues of genes encoding growth factor receptors, and there is a potential for aberrant activation of FGF-dependent signaling in human pancreatic cancer (see, e.g., Ozawa et al., 2001).

The two prototypic members are acidic fibroblast growth factor (aFGF or FGF1) and basic fibroblast growth factors (bFGF or FGF2), and to date, at least twenty distinct FGF family members have been identified. The cellular response to FGFs is transmitted via four types of high affinity transmembrane tyrosine-kinase fibroblast growth factor receptors numbered 1 to 4 (FGFR-1 to FGFR-4). Upon ligand binding, the receptors dimerize and auto- or trans-phosphorylate specific cytoplasmic tyrosine residues to transmit an intracellular signal that ultimately reaches nuclear transcription factor effectors.

Disruption of the FGFR-1 (FGFRA) pathway should affect tumour cell proliferation since this kinase is activated in many tumour types in addition to proliferating endothelial cells. The overexpression and activation of FGFR-1 in tumour-associated vasculature has suggested a role for these molecules in tumour angiogenesis.

FGFR-2 has high affinity for the acidic and/or basic fibroblast growth factors, as well as the keratinocyte growth factor ligands. FGFR-2 also propagates the potent osteogenic effects of FGFs during osteoblast growth and differentiation. Mutations in FGFR-2, leading to complex functional alterations, were shown to induce abnormal ossification of cranial sutures (craniosynostosis), implying a major role of FGFR signaling in intramembranous bone formation. For example, in Apert (AP) syndrome, characterized by premature cranial suture ossification, most cases are associated with point mutations engendering gain-of-function in FGFR-2 (see, e.g., Lemonnier et al., 2001).

Lemonnier et al., 2001, "Role of N-cadherin and protein kinase C in osteoblast gene activation induced by the S252W fibroblast growth factor receptor 2 mutation in Apert craniosynostosis", *J. Bone Miner. Res*. Vol. 16, pp. 832-845.

Several severe abnormalities in human skeletal development, including Apert, Crouzon, Jackson-Weiss, Beare-Stevenson cutis gyrata, and Pfeiffer syndromes are associated with the occurrence of mutations in FGFR-2. Most, if not all, cases of Pfeiffer Syndrome (PS) are also caused by de novo mutation of the FGFR-2 gene (see, e.g., Meyers et al., 1996; Plomp et al., 1998), and it was recently shown that mutations in FGFR-2 break one of the cardinal rules governing ligand specificity. Namely, two mutant splice forms of fibroblast growth factor receptor, FGFR2c and FGFR2b, have acquired the ability to bind to and be activated by atypical FGF ligands. This loss of ligand specificity leads to aberrant signalling and suggests that the severe phenotypes of these disease syndromes result from ectopic ligand-dependent activation of FGFR-2 (see, e.g., Yu et al., 2000).

Activating mutations of the FGFR-3 receptor tyrosine kinase such as chromosomal translocations or point mutations produce deregulated, constitutively active, FGFR-3 receptors which have been involved in multiple myeloma and in bladder and cervix carcinomas (see, e.g., Powers et al., 2000). Accordingly, FGFR-3 inhibition would be useful in the treatment of multiple myeloma, bladder, and cervix carcinomas.

Angiogenesis

Chronic proliferative diseases are often accompanied by profound angiogenesis, which can contribute to or maintain an inflammatory and/or proliferative state, or which leads to tissue destruction through the invasive proliferation of blood vessels. See, e.g., Folkman, 1995; Folkman, 1997; Folkman et al., 1992.

Angiogenesis is generally used to describe the development of new or replacement blood vessels, or neovascularisation. It is a necessary and physiological normal process by which the vasculature is established in the embryo. Angiogenesis does not occur, in general, in most normal adult tissues, exceptions being sites of ovulation, menses, and wound healing. Many diseases, however, are characterized by persistent and unregulated angiogenesis. For instance, in arthritis, new capillary blood vessels invade the joint and destroy cartilage (see, e.g., Colville-Nash and Scott, 1992). In diabetes (and in many different eye diseases), new vessels invade the macula or retina or other ocular structures, and may cause blindness (see, e.g., Alon et al., 1995). The process of atherosclerosis has been linked to angiogenesis (see, e.g., Kahlon et al., 1992). Tumour growth and metastasis have been found to be angiogenesis-dependent (see, e.g., Folkman, 1992; Denekamp, 1993; Fidler and Ellis, 1994).

The recognition of the involvement of angiogenesis in major diseases has been accompanied by research to identify and develop inhibitors of angiogenesis. These inhibitors are generally classified in response to discrete targets in the angiogenesis cascade, such as activation of endothelial cells by an angiogenic signal; synthesis and release of degradative enzymes; endothelial cell migration; proliferation of endothelial cells; and formation of capillary tubules. Therefore, angiogenesis occurs in many stages and attempts are underway to discover and develop compounds that work to block angiogenesis at these various stages.

There are many publications that teach that inhibitors of angiogenesis, working by diverse mechanisms, are beneficial in diseases such as cancer and metastasis (see, e.g., O'Reilly et al., 1994; Ingber et al., 1990), ocular diseases (see, e.g., Friedlander et al., 1995), arthritis (see, e.g., Peacock et al., 1992; Peacock et al., 1995), and hemangioma (see, e.g., Taraboletti et al., 1995).

VEGFR

Vascular endothelial growth factor (VEGF), a polypeptide, is mitogenic for endothelial cells in vitro and stimulates angiogenic responses in vivo. VEGF has also been linked to inappropriate angiogenesis (see, e.g., Pinedo et al., 2000). VEGFR(s) are receptor tyrosine kinases (RTKs). RTKs catalyze the phosphorylation of specific tyrosyl residues in proteins involved in the regulation of cell growth and differentiation (see, e.g., Wilks et al., 1990; Courtneidge et al., 1993; Cooper et al., 1994; Paulson et al., 1995; Chan et al., 1996).

Three RTK receptors for VEGF have been identified: VEGFR-1 (Flt-1), VEGFR-2 (Flk-1 or KDR), and VEGFR-3 (Flt-4). These receptors are involved in angiogenesis and participate in signal transduction (see, e.g., Mustonen et al., 1995).

Of particular interest is VEGFR-2 (KDR), which is a transmembrane receptor RTK expressed primarily in endothelial cells. Activation of VEGFR-2 by VEGF is a critical step in the signal transduction pathway that initiates tumour angiogenesis. VEGF expression may be constitutive to tumour cells and can also be up-regulated in response to certain stimuli. One such stimuli is hypoxia, where VEGF expression is upregulated in both tumour and associated host tissues. The VEGF ligand activates VEGFR-2 by binding with its extracellular VEGF binding site. This leads to receptor dimerization of VEGFRs and auto-phosphorylation of tyrosine residues at the intracellular kinase domain of VEGFR-2. The kinase domain operates to transfer a phosphate from ATP to the tyrosine residues, thus providing binding sites for signalling proteins downstream of VEGFR-2 leading ultimately to initiation of angiogenesis (see, e.g., McMahon et al., 2000).

Inhibition at the kinase domain binding site of VEGFR-2 would block phosphorylation of tyrosine residues and serve to disrupt initiation of angiogenesis.

VEGFR-2 (and VEGFR-3) are primarily localized to the tumour vasculature (blood and/or lymphatic) supporting the majority of solid cancers, and is significantly upregulated. The primary clinical mechanism of action of VEGF signaling inhibitors is likely to be through the targeting of tumour vessels rather than tumour cells (see, e.g., Smith et al., 2010), although other mechanisms have been described. Vascular endothelial growth factor (VEGF)-targeted agents, administered either as single agents or in combination with chemotherapy, have been shown to benefit patients with advanced-stage malignancies (see, e.g., Ellis et al., 2008).

KDR plays a crucial role in other diseases, and inhibitors of KDR may find utility in these conditions.

Atherosclerosis:

KDR is strongly expressed both on endothelial cells during angiogenesis and on the luminal endothelium of human atherosclerotic vessels, but not in normal arteries or veins (see, e.g., Belgore et al., 2004). The interaction between VEGF and VEGF receptor 2 (KDR, human; Flk-1, mouse) is key to pathologic angiogenesis and has been implicated in the development of atherosclerotic lesions (see, e.g., Inoue et al., 1998). Vaccination against KDR resulted in T-cell activation, suppression of neo-angiogenesis, and a marked reduction in atherosclerosis which was independent of hypercholesterolemia in both male and female mice (see, e.g., Petrovan et al., 2007).

Obesity:

Formation of new vessels in fat tissues during diet-induced obesity is largely due to angiogenesis rather than de novo vasculogenesis. Anti-angiogenic treatment by blockade of VEGFR2 but not VEGFR1 may limit adipose tissue expansion (see, e.g., Tam et al., 2009).

Retinopathy and Maculopathy:

Abnormal activation of the VEGF-VEGFR system is intimately involved in the progression of age-related macular degeneration (AMD). Therefore, an aptamer against VEGF-$A_{165}$, a VEGF-neutralizing antibody (Fab type) and VEGF-Trap are now approved for AMD treatment (see, e.g., Masabumi et al., 2013). Bevazucimab, an anti-VEGF antibody, is used off-label in conditions such as AMD, diabetic retinopathy, and diabetic macular edema (DME) (see, e.g., Rotsos et al., 2008).

Neuropathic Pain Syndrome:

VEGF and VEGFR2 are involved in the pathogenesis of neuropathic pain. Anti-rVEGF treatment in CCI rats may alleviate chronic neuropathic pain by decreasing the expressions of VEGFR2 and P2X2/3 receptors on DRG neurons to inhibit the transmission of neuropathic pain signaling (see, e.g., Lin et al., 2010).

Rheumatoid Arthritis:

PTK787/ZK222584, a receptor tyrosine kinase inhibitors with specific activity against the VEGFRs, and that exhibits strong inhibition of VEGF-R2 (KDR) and slightly weaker inhibition of VEGFR1 (Flt-1), Flk-1 (the mouse homologue of KDR), and Flt-4 (the receptor found in the lymphatic system), inhibited knee swelling by 40%, severity scores (by 51%) and global histological scores in mice with collagen-induced arthritis (see, e.g., Grosios et al., 2004)

TIE

Angiopoietin 1 (Ang1), a ligand for the endothelium-specific receptor tyrosine kinase TIE-2 is an angiogenic factor (see, e.g., Davis et al., 1996; Partanen et al., 1992; Davis et al., 1994; Davis et al., 1996; Alitalo et al., 1996; Godowski et al., 1997). The acronym TIE represents "tyrosine kinase containing Ig and EGF homology domains". TIE is used to identify a class of receptor tyrosine kinases, which are exclusively expressed in vascular endothelial cells and early hemopoietic cells. Typically, TIE receptor kinases are characterized by the presence of an EGF-like domain and an immunoglobulin (IG) like domain, which consists of extracellular folding units, stabilized by intra-chain disulfide bonds (see, e.g., Partanen et al., 1999). Unlike VEGF, which functions during the early stages of vascular development, Ang1 and its receptor TIE-2 function in the later stages of vascular development, i.e., during vascular remodelling (remodelling refers to formation of a vascular lumen) and maturation (see, e.g., Yancopoulos et al., 1998; Peters et al., 1998; Suri et al., 1996).

Consequently, inhibition of TIE-2 would be expected to serve to disrupt remodelling and maturation of new vasculature initiated by angiogenesis thereby disrupting the angiogenic process.

p38 p38 is a MAPK family member of 38 kDa that is activated in response to stress and plays an important role in the immune response and cell survival and differentiation. Four p38 MAPK kinases have been described; these proteins share a high degree of homology (p38$\alpha$, $\beta$, $\gamma$, and $\delta$). p38 MAPKs can be activated by different stimuli such as growth factors, inflammatory cytokines, or a variety of environmental stresses. p38 MAPKs can in turn activate a number of downstream targets, including protein kinases, cytosolic substrates, transcription factors and chromatin remodeling factors. Strong activation of p38 MAPKs by cytokines and cellular stresses generally promotes the inhibition of cell growth and induces apoptosis (see, e.g., review in Cuadrado et al., 2010). More recently, p38$\alpha$ has been found to play important roles in the maintenance of homoeostasis and related pathologies. The best-known and most widely reported role of p38$\alpha$ in disease is related to its function in cytokine signaling and promotion of pathological inflammation. Several studies have shown how p38$\alpha$ can mediate a series of disease models, including rheumatoid arthritis, psoriasis, Alzheimer's disease, inflammatory bowel disease, Crohn's disease, tumourigenesis, cardiovascular disease, and stroke. Moreover, there is evidence of a role for p38 MAPK in the development and maintenance of a number of pulmonary diseases, such as asthma, cystic fibrosis, idiopathic pulmonary fibrosis, and chronic obstructive pulmonary disease. Thus, p38$\alpha$ is an interesting pharmaceutical target especially because of its important role in inflammatory diseases (see, e.g., review in Oeztuerk-Winder et al., 2012). Pyridinyl-imidazole drugs such as SB203580 were the first p38 MAPK inhibitors to be identified that bind competitively at the ATP-binding pocket, and have been widely used to study p38 MAPK functions (see, e.g., Coulthard et al., 2009).

SRC c-SRC belongs to the non-receptor SRC family kinases (SFKs). These proteins are involved in many cellular events such as proliferation, survival, and cell motility. Thus, hyper-activation of SRC signaling contributes to diverse aspects of tumour development.

The most prominent function of c-SRC is its extensive interaction with transmembrane receptor tyrosine kinases (RTKs) at the cell membrane via its SH2 and SH3 domains. c-SRC interacts with many RTKs including epidermal growth factor receptor (EGFR), human epidermal growth factor receptor 2 (HER2), platelet-derived growth factor receptor (PDGFR), insulin-like growth factor-1 receptor (IGF-1R) and c-Met/hepatocyte growth factor receptor (HGFR). Through these interactions, c-SRC integrates and regulates RTK signaling and directly transduces survival signals to downstream effectors such as phosphoinositide 3-kinases (PI3Ks), Akt, and signal transducer and activator of transcription 3 (STAT3) (see, e.g., Zhang et al., 2012). Other membrane receptors such as integrins can also activate c-SRC thus triggering a signal cascade that regulates cell migration adhesion and invasion. c-Src activation through the interaction with p120 catenin promotes dissociation of cell-cell adherens junctions thus enhancing cell motility. c-SRC directly phosphorylates the focal adhesion kinase (FAK) stabilizing focal adhesion complexes, which consist of FAK, paxillin, RhoA, and other components, and enhances cell adhesion to the extracellular matrix. Furthermore, c-SRC plays an important role in regulating the tumour microenvironment. c-SRC activation in hypoxia promotes angiogenesis through stimulation of the expression of vascular endothelial growth factor (VEGF), matrix metalloproteinase (MMPs) and interleukin-8 (IL-8) (see, e.g., Yeatman et al., 2004).

Targeting SFKs is a well established therapeutic approach for many types of cancer. Dasatinib is an orally available small-molecule multi-kinase inhibitor that potently inhibits SRC-family kinases (SRC, LCK, YES, FYN), but also BCR-ABL, c-KIT, PDGFR-α and β, and ephrin receptor kinase (see, e.g., Lindauer et al., 2010). More recent studies have reported that Src is also involved in the inflammation-related signaling pathway. Many studies have shown that c-SRC plays a critical role in macrophage-mediated inflammatory responses. Importantly, a variety of inflammatory diseases is closely related to macrophage activation; therefore, c-SRC inhibition may represent a useful therapeutic strategy for macrophage-mediated diseases (see, e.g., Byeon et al., 2012).

Lck

Lck (lymphocyte specific kinase) is a kinase of the SFKs that is critical for T-cell activation, and its activity is induced by the T-cell receptor (TCR). TCR signals initiated by Lck lead to gene regulation events resulting in cytokine release, proliferation and survival of antigen specific T-cells thereby amplifying specific immune responses. Inhibition of Lck is expected to offer a new therapeutic approach for the treatment of T-cell-mediated autoimmune and inflammatory disorders and/or organ transplant rejection (see, e.g., Martin et al., 2010).

Known Compounds

Niculescu-Duvaz et al., 2006, describes certain imidazo[4,5-b]pyridin-2-one and oxazolo[4,5-b]pyridin-2-one compounds which, inter alia, inhibit RAF (e.g., BRAF) activity, and which are useful in the treatment of proliferative disorders such as cancer. A number of compounds shown therein have a 5-(tert-butyl)-2-(phenyl)-pyrazol-3-yl group or a 5-(tert-butyl)-2-(pyridyl)-pyrazol-3-yl group. However, in every case, the phenyl and pyridyl group is unsubstituted, para-substituted, or ortho, para-disubstituted; in none of the compounds is it meta-substituted. The following compounds are shown:

| Structure | Citation |
|---|---|
| 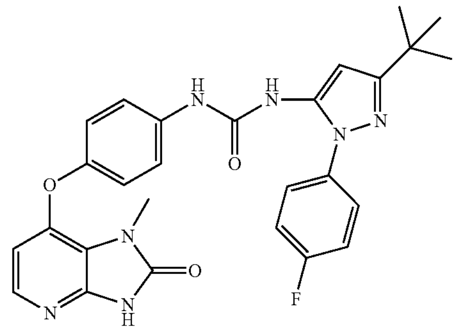 [SMILES: Cn1c(=O)[nH]c2nccc(Oc3ccc(NC(=O)Nc4cc(C(C)(C)C)nn4-c4ccc(F)cc4)cc3)c21] | CJS 3247 |
| 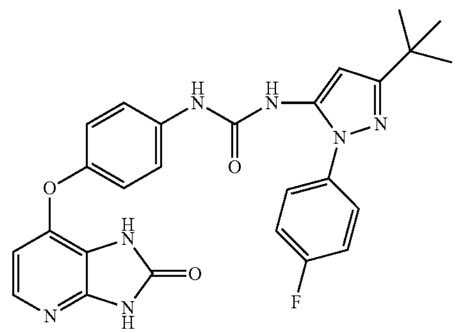 [SMILES: CC(C)(C)c1cc(NC(=O)Nc2ccc(Oc3ccnc4[nH]c(=O)[nH]c34)cc2)n(-c2ccc(F)cc2)n1] | CJS 3600 |
| 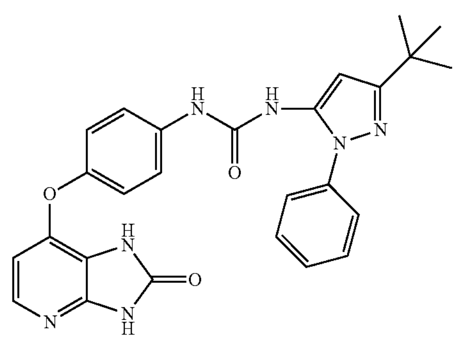 [SMILES: CC(C)(C)c1cc(NC(=O)Nc2ccc(Oc3ccnc4[nH]c(=O)[nH]c34)cc2)n(-c2ccccc2)n1] | CJS 3608 |
| 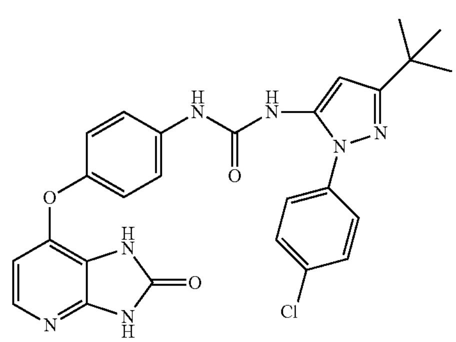 [SMILES: CC(C)(C)c1cc(NC(=O)Nc2ccc(Oc3ccnc4[nH]c(=O)[nH]c34)cc2)n(-c2ccc(Cl)cc2)n1] | CJS 3609 |

| Structure | Citation |
|---|---|
| 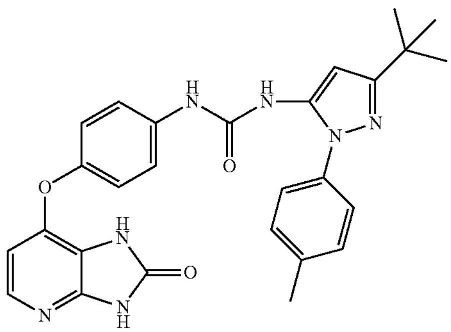 [SMILES: Cc1ccc(-n2nc(C(C)(C)C)cc2NC(=O)Nc2ccc(Oc3ccnc4[nH]c(=O)[nH]c34)cc2)cc1] | CJS 3614 |
| 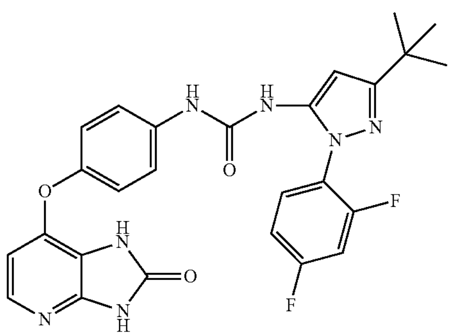 [SMILES: CC(C)(C)c1cc(NC(=O)Nc2ccc(Oc3ccnc4[nH]c(=O)[nH]c34)cc2)n(-c2ccc(F)cc2F)n1] | CJS 3615 |
| 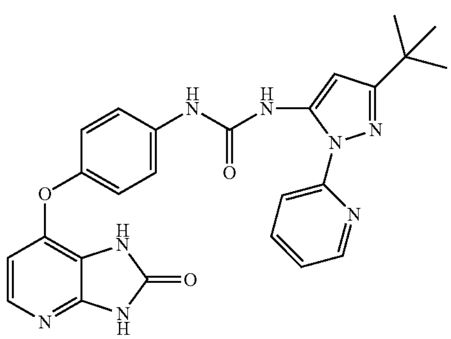 [SMILES: CC(C)(C)c1cc(NC(=O)Nc2ccc(Oc3ccnc4[nH]c(=O)[nH]c34)cc2)n(-c2ccccn2)n1] | CJS 3617 |

Niculescu-Duvaz et al., 2007, describes certain imidazo[4,5-b]pyridin-2-one and oxazolo[4,5-b]pyridin-2-one compounds which, inter alia, inhibit RAF (e.g., BRAF) activity, and which are useful in the treatment of proliferative disorders such as cancer. A number of compounds shown therein have a 5-(tert-butyl)-2-(phenyl)-pyrazol-3-yl group. However, in every case, the phenyl group is unsubstituted or para-substituted; in none of the compounds is it meta-substituted. The following compounds are shown:

| Structure | Citation |
|---|---|
| 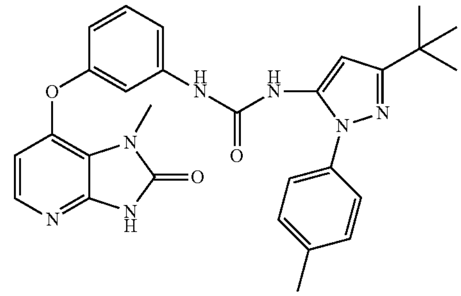 [SMILES: Cc1ccc(-n2nc(C(C)(C)C)cc2NC(=O)Nc2cccc(Oc3ccnc4[nH]c(=O)n(C)c34)c2)cc1] | CJS 3683 |
| 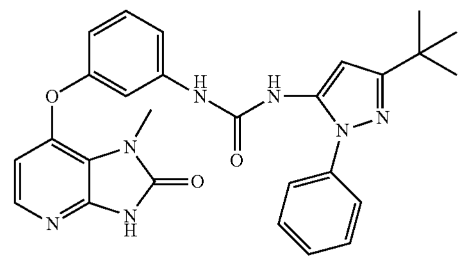 [SMILES: Cn1c(=O)[nH]c2nccc(Oc3cccc(NC(=O)Nc4cc(C(C)(C)C)nn4-c4ccccc4)c3)c21] | CJS 3741 |
| 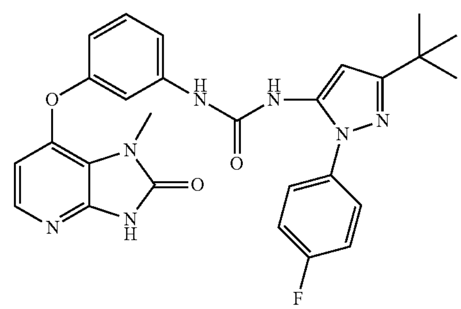 [SMILES: Cn1c(=O)[nH]c2nccc(Oc3cccc(NC(=O)Nc4cc(C(C)(C)C)nn4-c4ccc(F)cc4)c3)c21] | CJS 3742 |

Springer et al., 2009, describes certain pyrido[2,3-b]pyrazin-8-substituted compounds which, inter alia, inhibit RAF (e.g., BRAF) activity, and which are useful in the treatment of proliferative disorders such as cancer. A number of compounds shown therein have a 5-(tert-butyl)-2-(phenyl)-pyrazol-3-yl group or a 5-(tert-butyl)-2-(pyridyl)-pyrazol-3-yl group. However, in every case, the phenyl and pyridyl group is unsubstituted or para-substituted; in none of the compounds is it meta-substituted. The following compounds are shown:

| Structure | Citation |
|---|---|
| 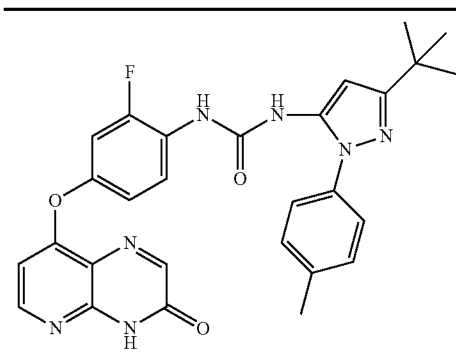 | Compound AA-018 |

| Structure | Citation |
|---|---|
| 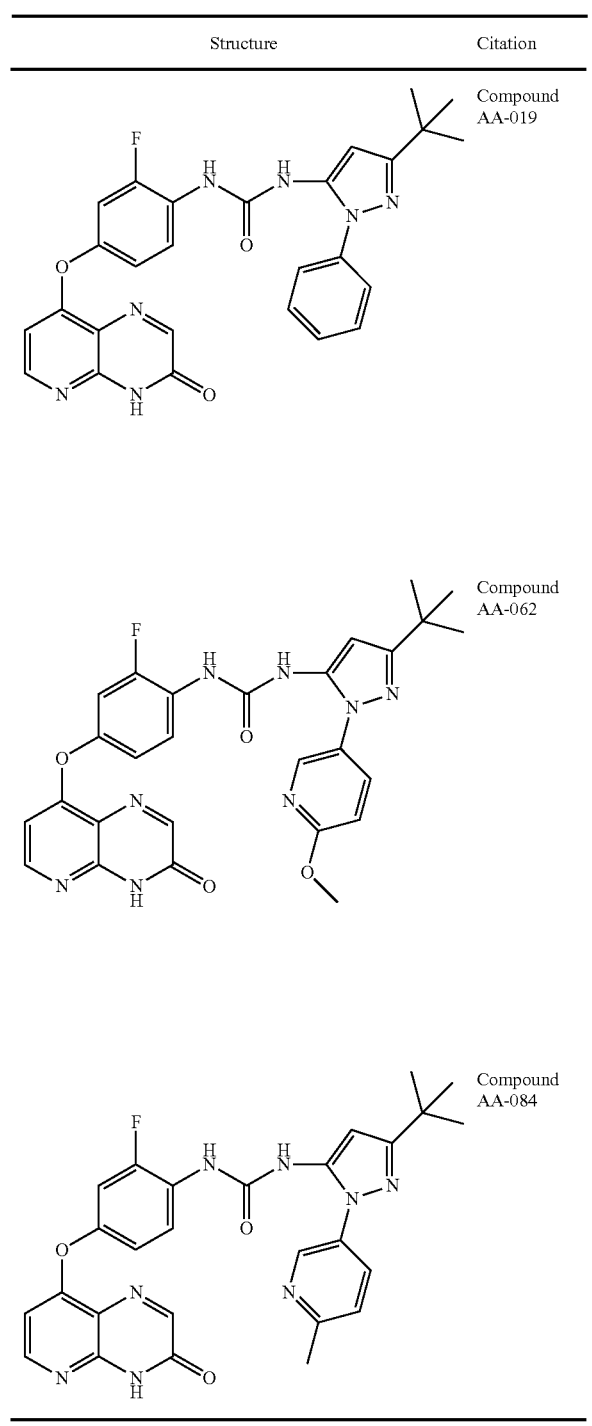 | Compound AA-019 |
| 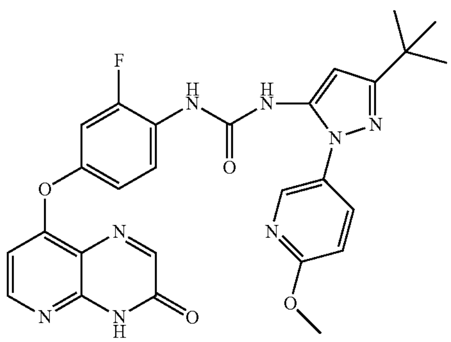 [SMILES: COc1ccc(-n2nc(C(C)(C)C)cc2NC(=O)Nc2ccc(Oc3ccnc4[nH]c(=O)cnc34)cc2F)cn1] | Compound AA-062 |
| 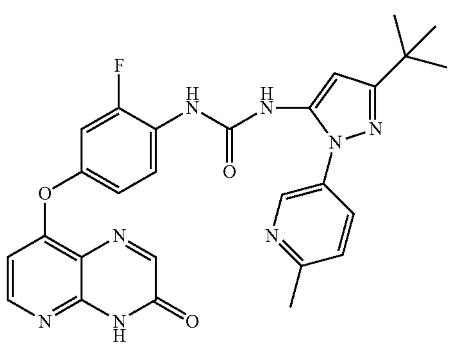 [SMILES: Cc1ccc(-n2nc(C(C)(C)C)cc2NC(=O)Nc2ccc(Oc3ccnc4[nH]c(=O)cnc34)cc2F)cn1] | Compound AA-084 |

| Structure | Citation |
|---|---|
| 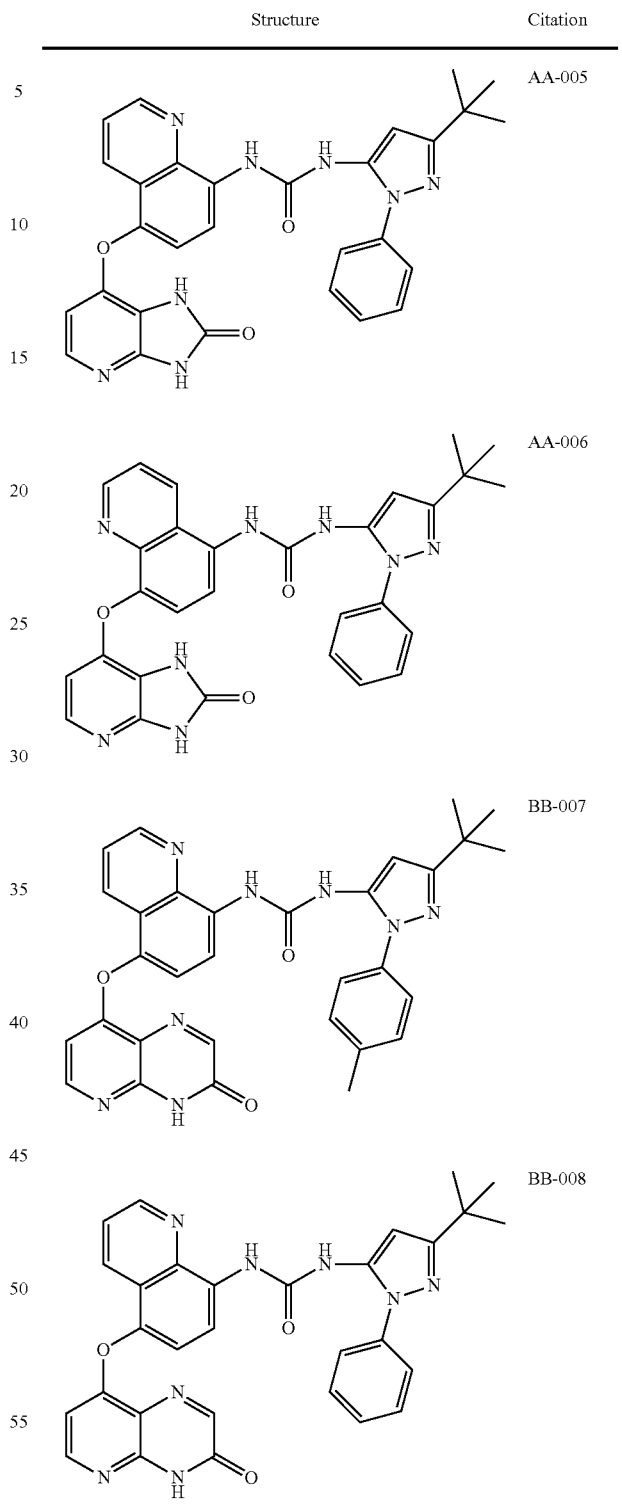 | AA-005 |
| 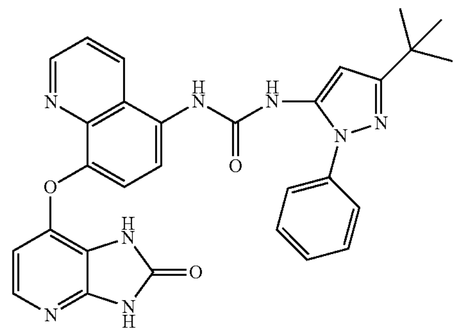 [SMILES: CC(C)(C)c1cc(NC(=O)Nc2ccc(Oc3ccnc4[nH]c(=O)[nH]c34)c3ncccc23)n(-c2ccccc2)n1] | AA-006 |
| 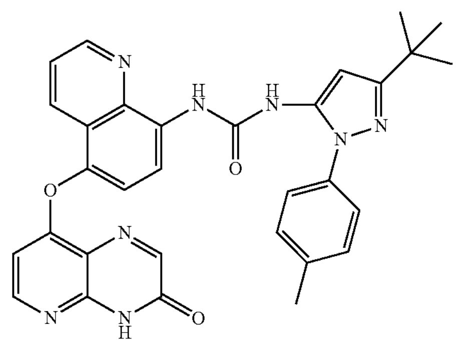 [SMILES: Cc1ccc(-n2nc(C(C)(C)C)cc2NC(=O)Nc2ccc(Oc3ccnc4[nH]c(=O)cnc34)c3cccnc23)cc1] | BB-007 |
| 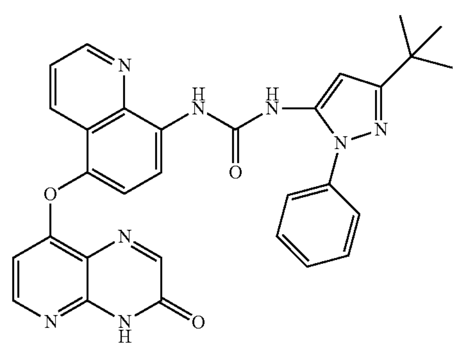 [SMILES: CC(C)(C)c1cc(NC(=O)Nc2ccc(Oc3ccnc4[nH]c(=O)cnc34)c3cccnc23)n(-c2ccccc2)n1] | BB-008 |

Niculescu-Duvaz et al., 2009, describes certain arylquinolinyl compounds which, inter alia, inhibit RAF (e.g., BRAF) activity, and which are useful in the treatment of proliferative disorders such as cancer. A number of compounds shown therein have a 5-(tert-butyl)-2-(phenyl)-pyrazol-3-yl group. However, in every case, the phenyl group is unsubstituted or para-substituted; in none of the compounds is it meta-substituted. The following compounds are shown:

Springer et al., 2011, describes certain 1-(5-tert-butyl-2-phenyl-2H-pyrazol-3-yl)-3-[2-fluoro-4-(1-methyl-2-oxo-2,3-dihydro-1H-imidazo[4,5-b]pyridin-7-yloxy)-phenyl]urea compounds which, inter alia, inhibit RAF (e.g., BRAF) activity, and which are useful in the treatment of proliferative disorders such as cancer. The following compound is shown:

| Structure | Citation |
|---|---|
| 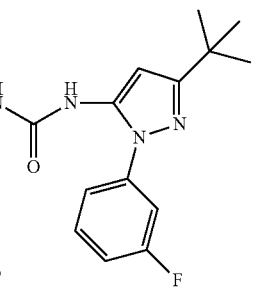 | Compound AA-04 |

Murray et al., 2011, describes certain compounds for use in the treatment of an inflammatory disease or a respiratory disorder. A few of the compounds shown therein have a 5-(tert-butyl)-2-(phenyl)-pyrazol-3-yl group or a 5-(tert-butyl)-2-(pyridyl)-pyrazol-3-yl group. However, in every case, the phenyl and pyridyl group is unsubstituted, para-substituted, or meta, para-substituted; in none of the compounds is it meta-substituted, para-unsubstituted. The following compounds are shown:

| Structure | Citation |
|---|---|
| 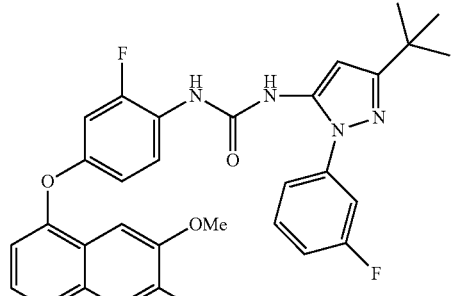 | Example 18 (page 58) |
| 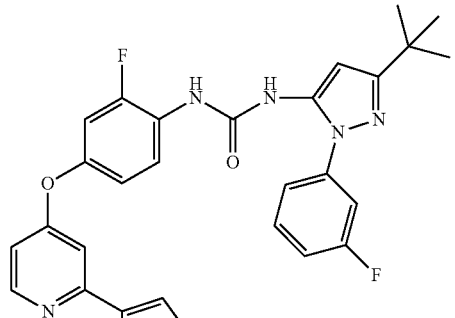 | Example 32 (page 63) |

A number of compounds having a 5-(tert-butyl)-2-(3-fluoro-phenyl)-pyrazol-3-yl group are known, including the following:

| Structure | Citation |
|---|---|
| 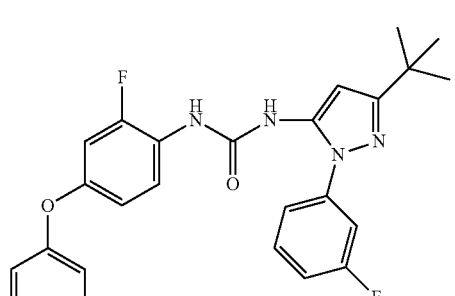 | Furuta et al., 2012 |
| 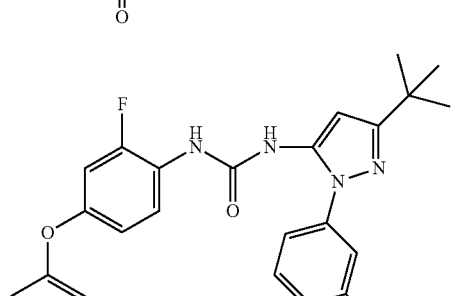 | Flynn et al., 2008 |
| 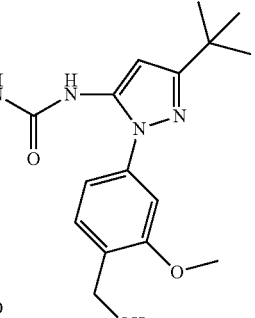 | Smith et al., 2007 |
| 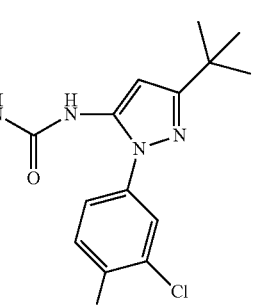 | Cantin et al., 2007 |

SUMMARY OF THE INVENTION

One aspect of the invention pertains to certain 1-(5-tert-butyl-2-aryl-pyrazol-3-yl)-3-[2-fluoro-4-[(3-oxo-4H-pyrido[2,3-b]pyrazin-8-yl)oxy]phenyl]urea compounds (referred to herein as "TBAP compounds"), as described herein.

Another aspect of the invention pertains to a composition (e.g., a pharmaceutical composition) comprising a TBAP compound, as described herein, and a pharmaceutically acceptable carrier or diluent.

Another aspect of the invention pertains to a method of preparing a composition (e.g., a pharmaceutical composition) comprising the step of mixing a TBAP compound, as described herein, and a pharmaceutically acceptable carrier or diluent.

Another aspect of the present invention pertains to a method of inhibiting RAF (e.g., BRAF, CRAF, etc.) function (e.g., in a cell), in vitro or in vivo, comprising contacting the cell with an effective amount of a TBAP compound, as described herein.

Another aspect of the present invention pertains to a TBAP compound as described herein for use in a method of treatment of the human or animal body by therapy, for example, for use in a method of treatment of a disorder (e.g., a disease) as described herein.

Another aspect of the present invention pertains to use of a TBAP compound, as described herein, in the manufacture of a medicament, for example, for use in a method of treatment, for example, for use in a method of treatment of a disorder (e.g., a disease) as described herein.

Another aspect of the present invention pertains to a method of treatment, for example, a method of treatment of a disorder (e.g., a disease) as described herein, comprising administering to a subject in need of treatment a therapeutically-effective amount of a TBAP compound, as described herein, preferably in the form of a pharmaceutical composition.

Another aspect of the present invention pertains to a kit comprising (a) a TBAP compound, as described herein, preferably provided as a pharmaceutical composition and in a suitable container and/or with suitable packaging; and (b) instructions for use, for example, written instructions on how to administer the compound.

Another aspect of the present invention pertains to a TBAP compound obtainable by a method of synthesis as described herein, or a method comprising a method of synthesis as described herein.

Another aspect of the present invention pertains to a TBAP compound obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspects of the invention.

DETAILED DESCRIPTION OF THE INVENTION

Compounds

One aspect of the present invention relates to certain 1-(5-tert-butyl-2-aryl-pyrazol-3-yl)-3-[2-fluoro-4-[(3-oxo-4H-pyrido[2,3-b]pyrazin-8-yl)oxy]phenyl]urea compounds which are structurally related the following compounds:

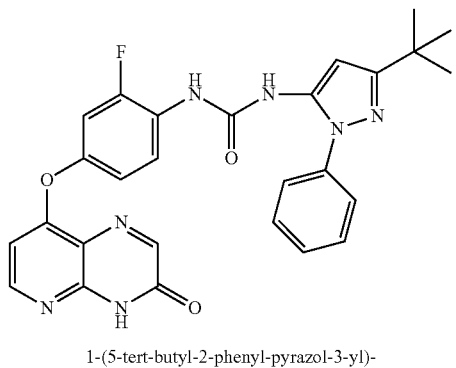

1-(5-tert-butyl-2-phenyl-pyrazol-3-yl)-
3-[2-fluoro-4-[(3-oxo-4H-pyrido[2,3-
b]pyrazin-8-yl)oxy]phenyl]urea

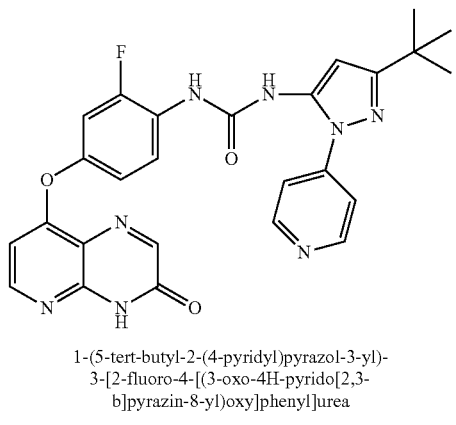

1-(5-tert-butyl-2-(4-pyridyl)pyrazol-3-yl)-
3-[2-fluoro-4-[(3-oxo-4H-pyrido[2,3-
b]pyrazin-8-yl)oxy]phenyl]urea More particularly, the present invention relates to certain related compounds which additionally have a single meta substituent (denoted herein as —Y).

Thus, one aspect of the present invention pertains to compounds selected from compounds of the following formula, and pharmaceutically acceptable salts, N-oxides, hydrates, and solvates thereof, wherein =X— and —Y are as defined herein (for convenience, collectively referred to herein as "TBAP compounds"):

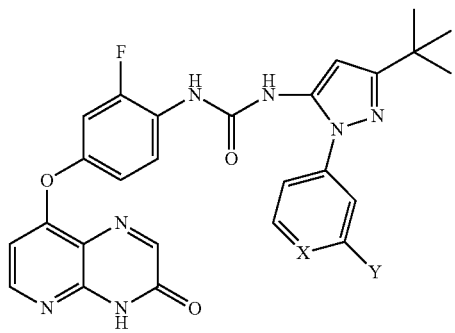

Some embodiments of the invention include the following:

(1) A compound selected from compounds of the following formula, and pharmaceutically acceptable salts, N-oxides, hydrates, and solvates thereof:

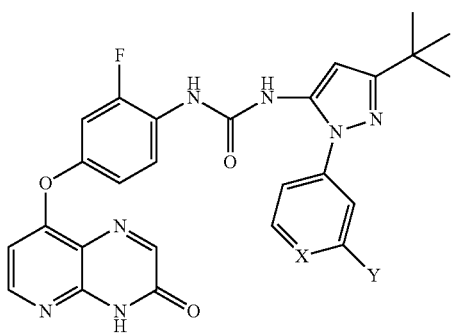

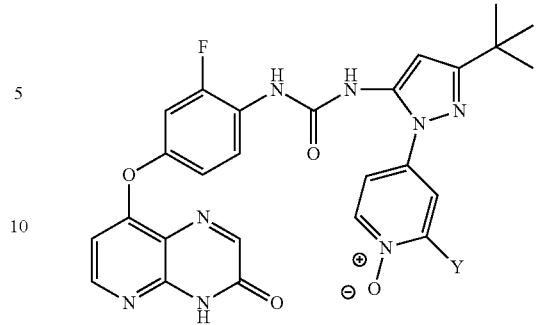

wherein:

=X— is independently =CH— or =N—;

—Y is independently —Y$^1$, —Y$^2$, —Y$^3$, —Y$^4$, —Y$^5$, or —Y$^6$;

—Y$^1$ is independently —F, —Cl, —Br, or —I;

—Y$^2$ is linear or branched saturated C$_{1-4}$alkyl;

—Y$^3$ is linear or branched saturated C$_{1-4}$haloalkyl;

—Y$^4$ is —OH;

—Y$^5$ is linear or branched saturated C$_{1-4}$alkoxy; and

—Y$^6$ is linear or branched saturated C$_{1-4}$haloalkoxy.

Note that, tautomerisation is possible on the 3-oxo-3,4-dihydropyrido[3,2-b]pyrazin-8-yl group, as shown below. Unless otherwise indicated, a reference to one tautomer is intended to be a reference to both tautomers.

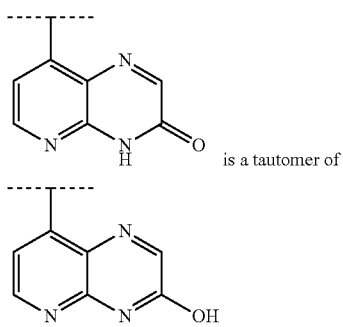

Note that when —X= is —N= and —Y is —Y$^4$ (i.e., —OH), tautomerisation is possible on the resulting 2-hydroxy-pyrid-4-yl group, as shown below. Unless otherwise indicated, a reference to one tautomer is intended to be a reference to both tautomers.

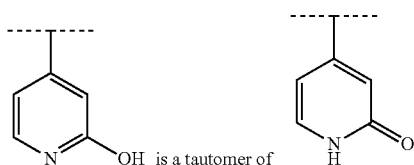

Note that when =X— is =N—, the resulting group is a pyridyl-4-yl group, and an N-oxide may be formed, as shown below.

For the avoidance of doubt, the term "linear or branched saturated C$_{1-4}$haloalkyl" relates to a linear or branched saturated C$_{1-4}$alkyl group that has 1 or more (e.g., 1, 2, 3, etc.) halogen (e.g., —F, —Cl, —Br, —I) substituents. An example of such a group is —CF$_3$.

For the avoidance of doubt, the term "linear or branched saturated C$_{1-4}$alkoxy" relates to a group —OR, where R is a linear or branched saturated C$_{1-4}$alkyl group. An example of such a group is —OMe.

Similarly, the term "linear or branched saturated C$_{1-4}$haloalkoxy" relates to a group —OR, where R is a linear or branched saturated C$_{1-4}$haloalkyl group. An example of such a group is —OCF$_3$.

For the avoidance of doubt: methyl is abbreviated as -Me; ethyl is abbreviated as -Et; n-propyl is abbreviated as -nPr; iso-propyl is abbreviated as -iPr; n-butyl is abbreviated as -nBu; iso-butyl is abbreviated as -iBu; sec-butyl is abbreviated as -sBu; tert-butyl is abbreviated as -tBu; and phenyl is abbreviated as -Ph.

The Group =X—

(2) A compound according to (1), wherein =X— is =CH—.

(3) A compound according to (1), wherein =X— is =N—.

The Group —Y (4) A compound according to any one of (1) to (3), wherein —Y is —Y$^1$.

(5) A compound according to any one of (1) to (3), wherein —Y is —Y$^2$.

(6) A compound according to any one of (1) to (3), wherein —Y is —Y$^3$.

(7) A compound according to any one of (1) to (3), wherein —Y is —Y$^4$.

(8) A compound according to any one of (1) to (3), wherein —Y is —Y$^5$.

(9) A compound according to any one of (1) to (3), wherein —Y is —Y$^8$.

The Group —Y$^1$

(10) A compound according to any one of (1) to (9), wherein —Y$^1$, if present, is independently —F, —Cl, —Br.

(11) A compound according to any one of (1) to (9), wherein —Y$^1$, if present, is independently —F or —Cl.

(12) A compound according to any one of (1) to (9), wherein —Y$^1$, if present, is —F.

(13) A compound according to any one of (1) to (9), wherein —Y$^1$, if present, is —Cl.

(14) A compound according to any one of (1) to (9), wherein —Y, if present, is —Br.

(15) A compound according to any one of (1) to (9), wherein —Y$^1$, if present, is —I.

The Group —Y²

(16) A compound according to any one of (1) to (15), wherein —Y², if present, is independently -Me, -Et, -nPr, -iPr, -nBu, -iBu, -sBu, or -tBu.

(17) A compound according to any one of (1) to (15), wherein —Y², if present, is independently -Me, -Et, -nPr, or -iPr.

(18) A compound according to any one of (1) to (15), wherein —Y², if present, is independently -Me or -Et.

(19) A compound according to any one of (1) to (15), wherein —Y², if present, is -Me.

The Group —Y³

(20) A compound according to any one of (1) to (19), wherein —Y³, if present, is linear or branched saturated $C_{1-4}$fluoroalkyl.

(21) A compound according to any one of (1) to (19), wherein —Y³, if present, is independently —$CH_2F$, —$CHF_2$, —$CF_3$, —$CH_2CH_2F$, —$CH_2CHF_2$, or —$CH_2CF_3$.

(22) A compound according to any one of (1) to (19), wherein —Y³, if present, is independently —$CH_2F$, —$CHF_2$, or —$CF_3$.

(23) A compound according to any one of (1) to (19), wherein —Y³, if present, is —$CF_3$.

The Group —Y⁵

(24) A compound according to any one of (1) to (23), wherein —Y⁵, if present, is independently —O-Me, —O-Et, —O-nPr, —O-iPr, —O-nBu, —O-iBu, —O-sBu, or —O-tBu.

(25) A compound according to any one of (1) to (23), wherein —Y⁵, if present, is independently —O-Me, —O-Et, —O-nPr, or —O-iPr.

(26) A compound according to any one of (1) to (23), wherein —Y⁵, if present, is independently —O-Me or —O-Et.

(27) A compound according to any one of (1) to (23), wherein —Y⁵, if present, is —O-Me.

The Group —Y⁶

(28) A compound according to any one of (1) to (27), wherein —Y⁶, if present, is linear or branched saturated $C_{1-4}$fluoroalkoxy.

(29) A compound according to any one of (1) to (27), wherein —Y⁶, if present, is independently —O—$CH_2F$, —O—$CHF_2$, —O—$CF_3$, —O—$CH_2CH_2F$, —O—$CH_2CHF_2$, or —O—$CH_2CF_3$.

(30) A compound according to any one of (1) to (27), wherein —Y⁶, if present, is independently —O—$CH_2F$, —O—$CHF_2$, or —O—$CF_3$.

(31) A compound according to any one of (1) to (27), wherein —$Y^E$, if present, is —O—$CF_3$.

Some Preferred Compounds

(32) A compound according to (1), selected from compounds of the following formulae and pharmaceutically acceptable salts, N-oxides, hydrates, and solvates thereof:

| Code | Structure |
| --- | --- |
| TBAP-01 | *(structure)* |
| TBAP-02 | *(structure)* |
| TBAP-03 | *(structure)* |
| TBAP-04 | *(structure)* |
| TBAP-05 | *(structure)* |

Combinations

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the chemical groups represented by the variables (e.g., =X—, —Y, —Y¹, —Y², —Y³, —Y⁴, —Y⁵, —Y⁶, etc.) are specifically embraced by the present invention and are disclosed herein just as if each and every combination was individually and explicitly disclosed, to the extent that such combinations embrace compounds that are stable compounds (i.e., compounds that can be isolated, characterised, and tested for biological activity). In addition, all sub-combinations of the chemical groups listed in the embodiments describing such variables are also specifically embraced by the present invention and are disclosed herein just as if each and every such sub-combination of chemical groups was individually and explicitly disclosed herein.

Substantially Purified Forms

One aspect of the present invention pertains to TBAP compounds, as described herein, in substantially purified form and/or in a form substantially free from contaminants.

In one embodiment, the compound is in substantially purified form and/or in a form substantially free from contaminants.

In one embodiment, the compound is in a substantially purified form with a purity of least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

In one embodiment, the compound is in a form substantially free from contaminants wherein the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight. Unless specified, the contaminants refer to other compounds.

Isomers

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms: d- and l-forms; (+) and (−) forms; keto-, enol-, and enolate-forms: syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH₃, is not to be construed as a reference to its structural isomer, a hydroxymethyl group, —CH₂OH. Similarly, a reference to ortho-chlorophenyl is not to be construed as a reference to its structural isomer, meta-chlorophenyl. However, a reference to a class of structures may well include structurally isomeric forms falling within that class (e.g., C₇alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

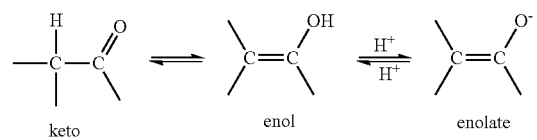

Note that specifically included in the term "isomer" are compounds with one or more isotopic substitutions. For example, H may be in any isotopic form, including ¹H, ²H (D), and ³H (T); C may be in any isotopic form, including ¹²C, ¹³C, and ¹⁴C; O may be in any isotopic form, including ¹⁶O and ¹⁸O; and the like.

Unless otherwise specified, a reference to a particular compound includes all such isomeric forms, including mixtures thereof. Methods for the preparation and separation of such isomeric forms are either known in the art or are readily obtained by adapting the methods taught herein, or known methods, in a known manner.

Salts

It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group which may be anionic (e.g., —COOH may be —COO⁻), then a salt may be formed with a suitable cation. Examples of suitable inorganic cations include, but are not limited to, alkali metal ions such as Na⁺ and K⁺, alkaline earth cations such as Ca²⁺ and Mg²⁺, and other cations such as Al³⁺. Examples of suitable organic cations include, but are not limited to, ammonium ion (i.e., NH₄⁺) and substituted ammonium ions (e.g., NH₃R⁺, NH₂R₂⁺, NHR₃⁺, NR₄⁺). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH₃)₄⁺.

If the compound is cationic, or has a functional group which may be cationic (e.g., —NH₂ may be —NH₃⁺), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetoxybenzoic, acetic, ascorbic, aspartic, benzoic, camphorsulfonic, cinnamic, citric, edetic, ethanedisulfonic, ethanesulfonic, formic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

N-Oxides

It may be convenient or desirable to prepare, purify, and/or handle a corresponding N-oxide of the compound. For example, a compound having a pyridyl group may be prepared, purified, and/or handled as the corresponding N-oxide.

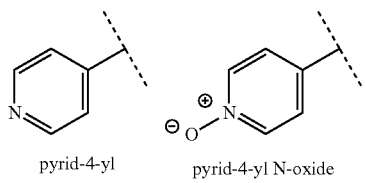

pyrid-4-yl        pyrid-4-yl N-oxide

Unless otherwise specified, a reference to a particular compound also includes N-oxide forms thereof.

Hydrates and Solvates

It may be convenient or desirable to prepare, purify, and/or handle a corresponding solvate of the compound. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes solvate and hydrate forms thereof.

Chemically Protected Forms

It may be convenient or desirable to prepare, purify, and/or handle the compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well-known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Greene and P. Wuts; 4th Edition; John Wiley and Sons, 2006).

A wide variety of such "protecting," "blocking," or "masking" methods are widely used and well-known in organic synthesis. For example, a compound which has two nonequivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH$_3$, —OAc).

For example, an aldehyde or ketone group may be protected as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

Prodrugs

It may be convenient or desirable to prepare, purify, and/or handle the compound in the form of a prodrug. The term "prodrug," as used herein, pertains to a compound which, when metabolised (e.g., in vivo), yields the desired active compound. Typically, the prodrug is inactive, or less active than the desired active compound, but may provide advantageous handling, administration, or metabolic properties.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Chemical Synthesis

Methods for the chemical synthesis of compounds of the present invention are described herein. These and/or other well-known methods may be modified and/or adapted in known ways in order to facilitate the synthesis of additional compounds within the scope of the present invention.

Descriptions of general laboratory methods and procedures, useful for the preparation of the compounds described herein, are provided in *Vogel's Textbook of Practical Organic Chemistry*, 5th Edition, 1989, (Editors: Furniss, Hannaford, Smith, and Tatchell) (published by Longmann, UK).

Methods for the synthesis of pyridine compounds in particular are described in *Heterocyclic Chemistry*, 3rd Edition, 1998, (Editors: Joule, Mills, and Smith) (published by Chapman & Hall, UK).

The TBAP compounds described herein may be prepared via key intermediate (2). This intermediate may be prepared from commercially available starting material, 2-amino-3-nitro-4-chloropyridine (1), and 3-fluoro-4-aminophenol. Intermediate (2) can be protected selectively at the amino group, for example as a BOC carbamate, to afford intermediate (3).

An example of such a method is illustrated in the following scheme.

Scheme 1

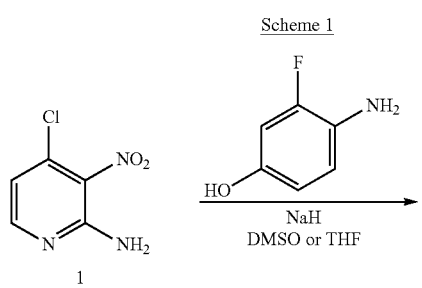

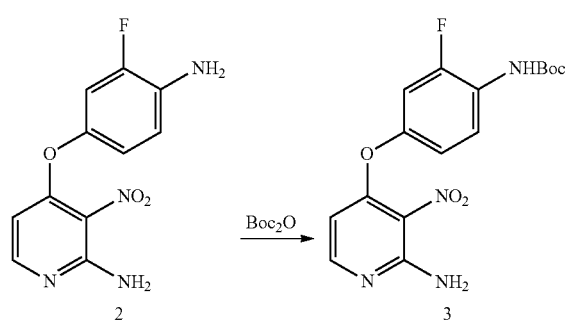

Intermediate (3) can also be obtained directly from 2-amino-3-nitro-4-chloropyridine (1) and N-BOC-protected 3-fluoro-4-aminophenol.

An example of such a method is illustrated in the following scheme.

Scheme 2

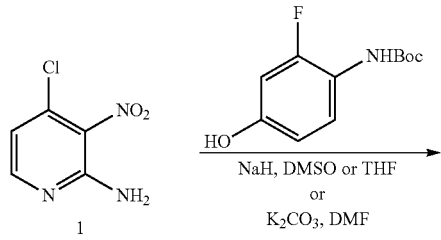

The nitro group of the protected intermediate (3) may be reduced to give an amino group, for example, with Pd/C and ammonium formate or hydrogen, or with NiCl$_2$ and NaBH$_4$, to give the diamino intermediate (4).

An example of such a method is illustrated in the following scheme.

Scheme 3

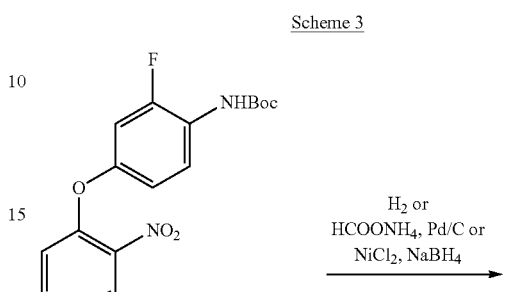

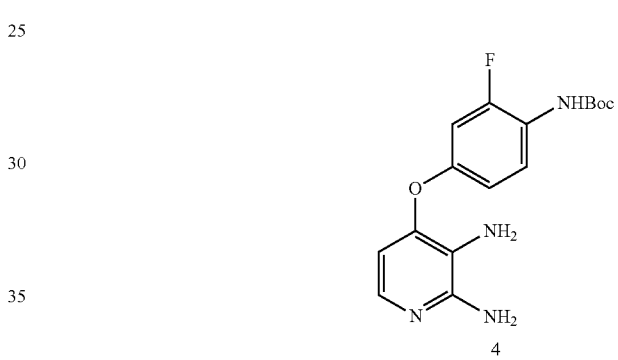

Pyridopyrazinones can be obtained from intermediate (4) by reaction with ethyl glyoxylate or glyoxylic acid. Both isomers (5) and (6) can be obtained from the reaction of (4) with ethyl glyoxalate or glyoxylic acid. The ratio of the two isomers can be influenced by the choice of reagents and solvents, so that one is obtained preferentially. The desired isomer (5) can be separated from the mixture by column chromatography or selective crystallisation from the mixture.

An example of such a method is illustrated in the following scheme.

Scheme 4

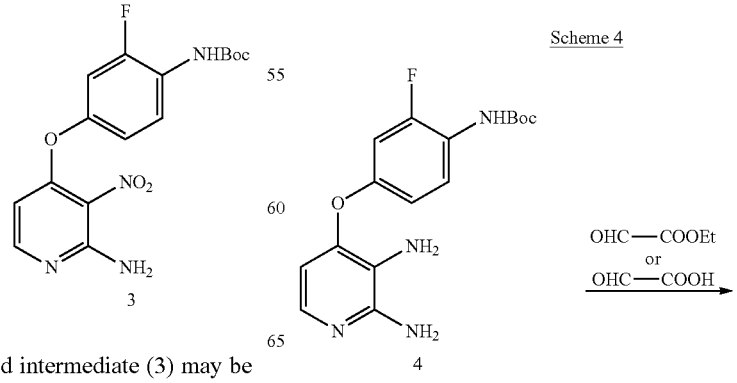

-continued

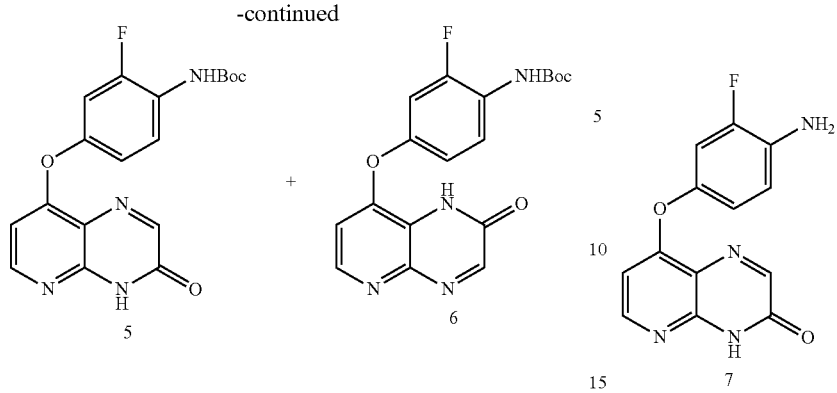

5

6

Scheme 6

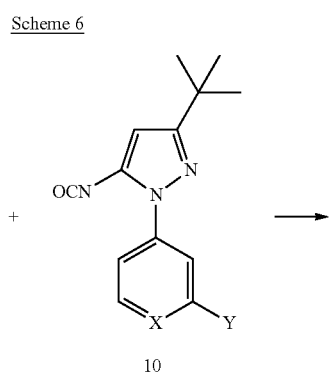

7

10

Deprotection of the protecting group (PG), for example, with tetrabutyl ammonium fluoride (TBAF) for a Boc protecting group, produces the common intermediate (7).

An example of such a method is illustrated in the following scheme.

Scheme 5

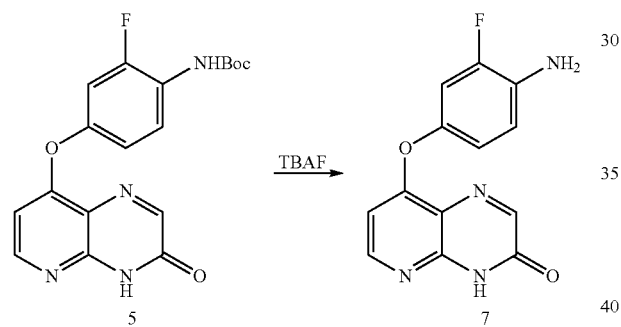

5

7

The key intermediate (7) is reacted with 3-tert-butyl-5-isocyanato-1-aryl-1H-pyrazoles (10) to afford the corresponding ureas (11).

An example of such a method is illustrated in the following scheme.

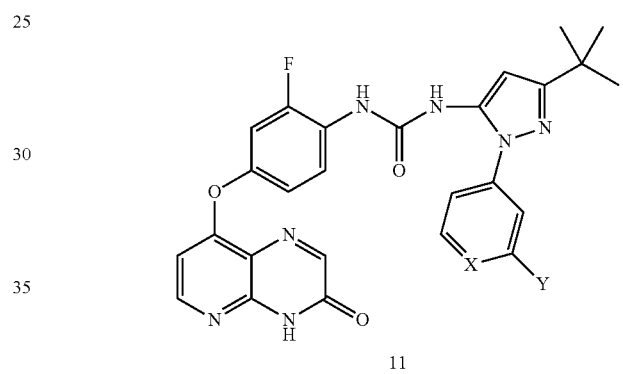

11

The respective isocyanates (10) can be obtained, for example, by the reaction of amines (9) with phosgene, triphosgene or their derivatives, or by conversion of the corresponding carboxylic acids (8) to acyl azides with, for example, diphenyl phosphoryl azide, followed by Curtius rearrangement. These reagents are identified for illustration only, and it should be noted that other suitable reagents are known in the art which may also be used to convert amines or carboxylic acids to isocyanates.

Examples of such methods are illustrated in the following scheme.

Scheme 7

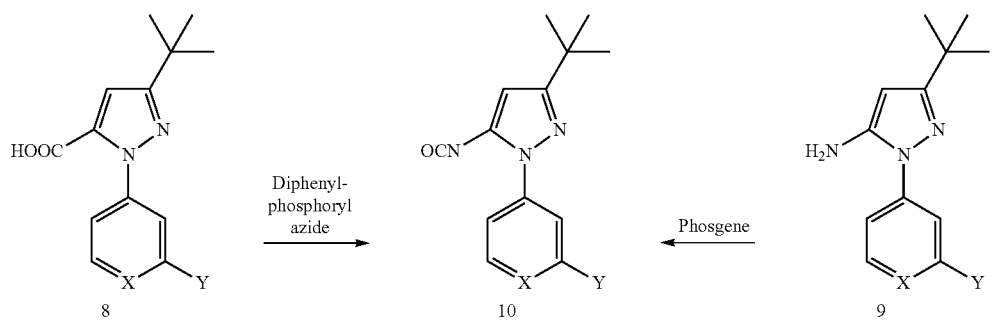

8

10

9

The desired carboxylic acids (8) can be obtained, for example, by the reaction of the corresponding meta-substituted phenyl or pyridyl boronic acids (R is H) or boronic esters (R is alkyl) (12) with 3-tert-butyl-1H-pyrazole-5-carboxylate ester followed by hydrolysis of the ester to carboxylic acid. The boronic esters, B(OR)$_2$ include cyclic esters, such as 4,4,5,5-tetramethyl-1,3,2-dioxaborolan-2-yl.

An example of such a method is illustrated in the following scheme.

Scheme 8

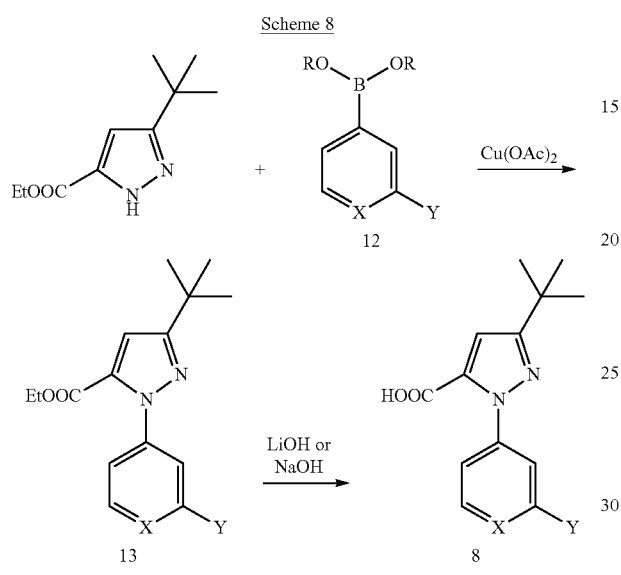

The desired amines (9) can be obtained, for example, by the reaction of the corresponding meta-substituted phenyl or pyridyl hydrazines (14) with 4,4-dimethyl-3-oxopentane nitrile.

An example of such a method is illustrated in the following scheme.

Scheme 9

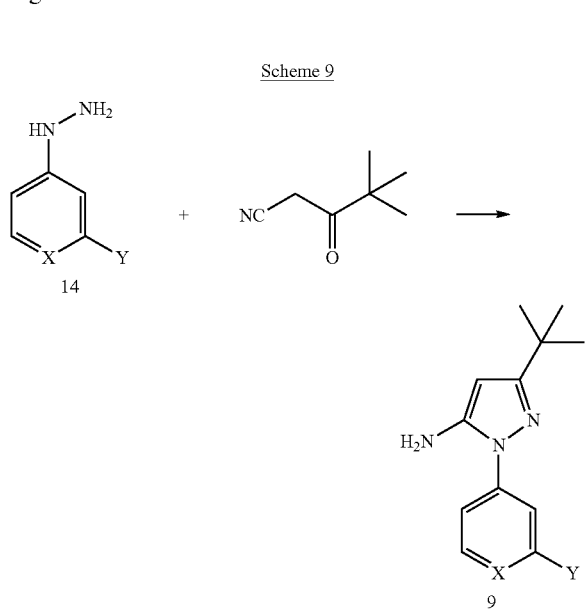

In an alternative approach, the intermediate (7) is reacted with activated carbamates of 3-tert-butyl-5-amino-1-aryl-1H-pyrazoles to afford the corresponding ureas.

An example of such a method is illustrated in the following scheme.

Scheme 10

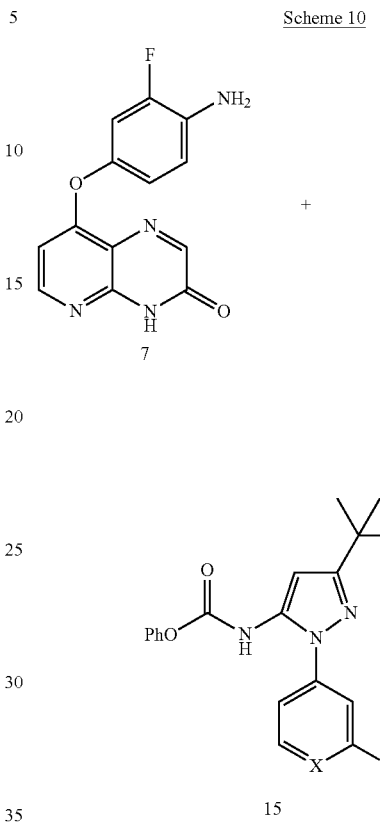

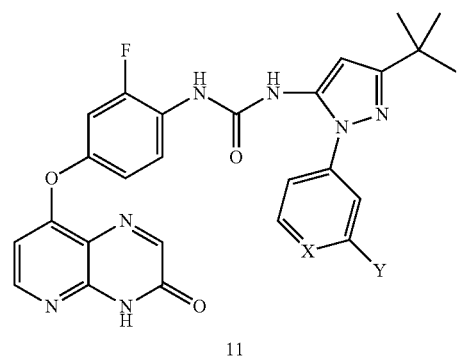

The respective activated carbamates can be obtained, for example, by the reaction of amines (9) with chloroformates, for example, with phenyl chloroformate to form phenyl (3-(tert-butyl)-1-aryl-1H-pyrazol-5-yl)carbamate (15) or with 1-methylvinyl chloroformate to form 1-methylvinyl (3-(tert-butyl)-1-aryl-1H-pyrazol-5-yl)carbamate.

Alternatively, the amino position of the common intermediate (7) can be activated by reaction, for example, with phenyl chloroformate or 1-methylvinylchloroformate.

An example of such a method is illustrated in the following scheme.

Scheme 11

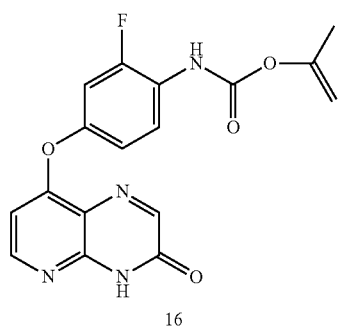

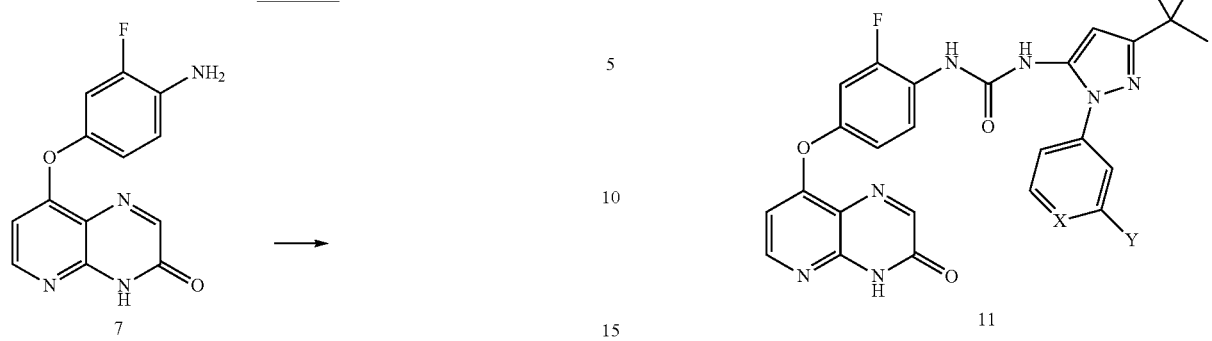

The activated carbamate so formed can then be reacted with an aromatic amine to afford the corresponding urea.

An example of such a method is illustrated in the following scheme.

Scheme 12

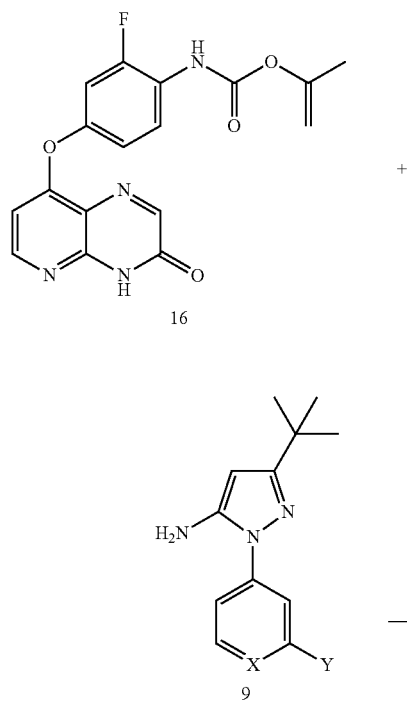

The activated carbamates shown in Schemes 10-12 above are merely examples. Other activated carbamates known in the art may also be used, including, for example, 4-nitrophenyl carbamates and N-hydroxysuccinimide carbamates.

In an alternative approach, the urea is formed first, prior to cyclisation.

An example of such a method is illustrated in the following scheme.

Scheme 13

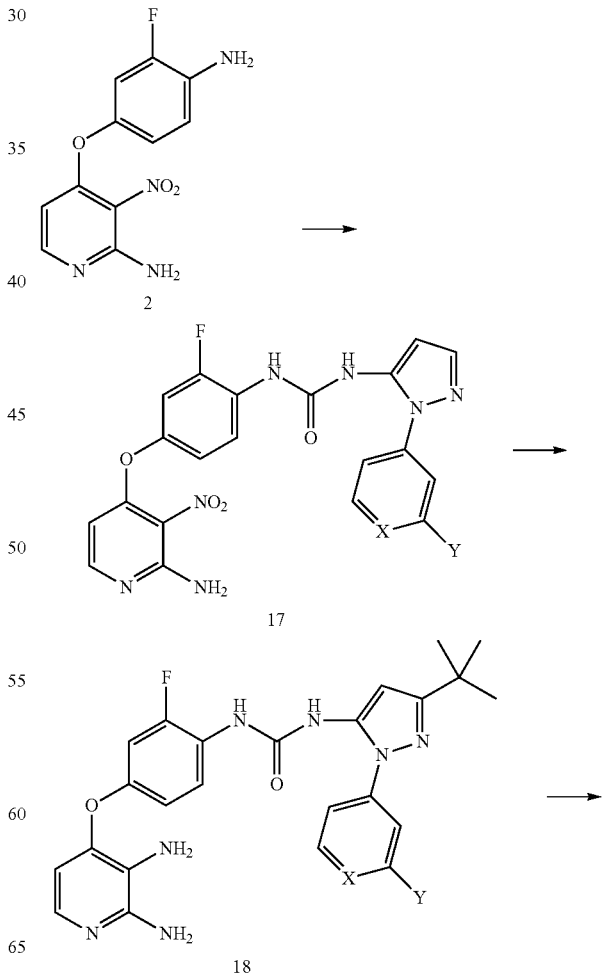

-continued

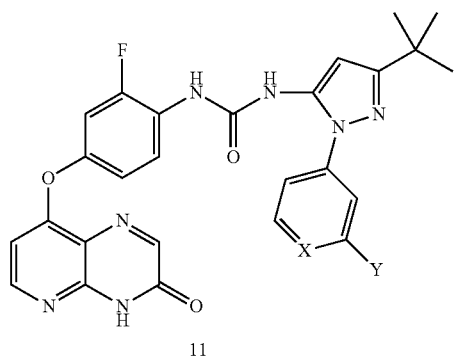

In an alternative approach, aminophenols can be converted to ureas to form intermediates (20).

An example of such a method is illustrated in the following scheme.

Scheme 14

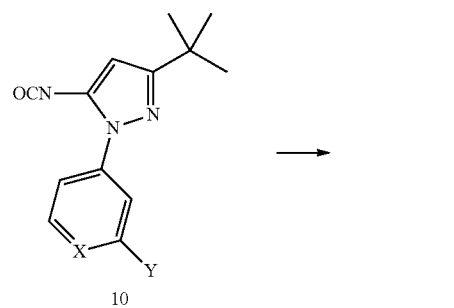

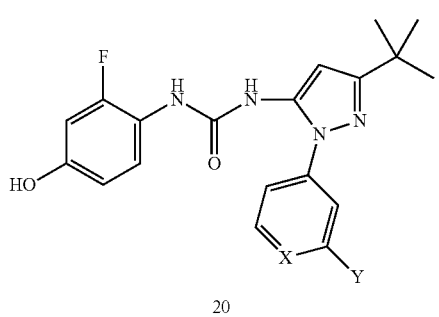

The intermediates (20) can then be coupled with (1) to afford (17). Further conversion, for example, as described above in Scheme 13, leads to product (11).

An example of such a method is illustrated in the following scheme.

Scheme 15

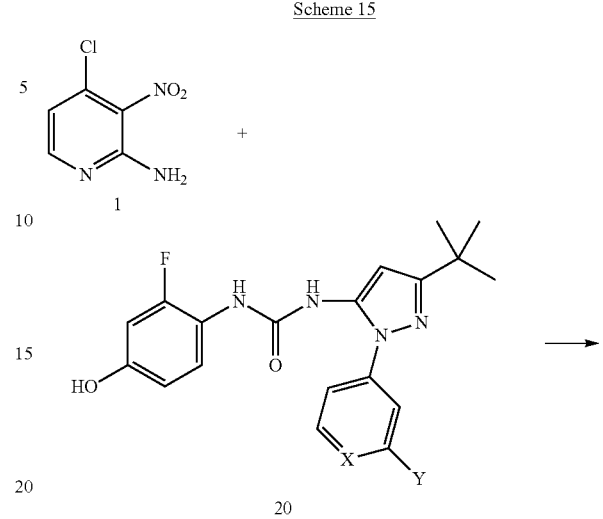

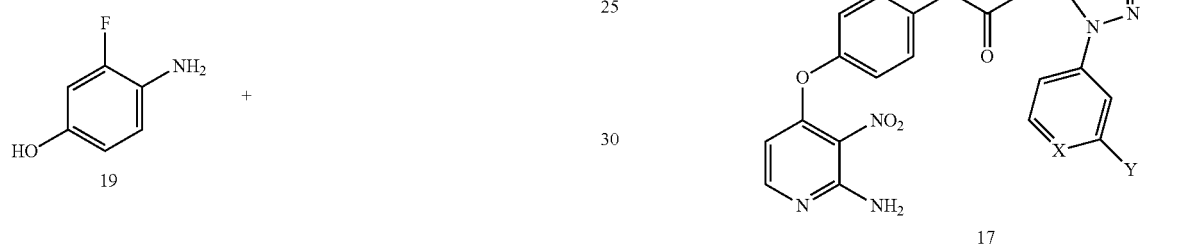

Compositions

One aspect of the present invention pertains to a composition (e.g., a pharmaceutical composition) comprising a TBAP compound, as described herein, and a pharmaceutically acceptable carrier, diluent, or excipient.

Another aspect of the present invention pertains to a method of preparing a composition (e.g., a pharmaceutical composition) comprising mixing a TBAP compound, as described herein, and a pharmaceutically acceptable carrier, diluent, or excipient.

Uses

The TBAP compounds described herein are useful in the treatment of, for example, proliferative disorders (as "anti-proliferative agents"), cancer (as "anti-cancer agents"), inflammatory diseases (as "anti-inflammatory agents"), viral infections (as "anti-viral agents"), neurodegenerative diseases (as "anti-neurodegenerative agents"), fibrotic diseases (as "anti-fibrotic agents"), etc.

Use in Methods of Inhibiting RAF (e.g., BRAF, CRAF, Etc.)

One aspect of the present invention pertains to a method of inhibiting RAF (e.g., BRAF, CRAF, etc.) function (e.g., in a cell), in vitro or in vivo, comprising contacting the cell with an effective amount of a TBAP compound, as described herein.

One of ordinary skill in the art is readily able to determine whether or not a candidate compound inhibits RAF (e.g., BRAF, CRAF, etc.). For example, suitable assays are described herein or are known in the art.

In one embodiment, the method is performed in vitro.

In one embodiment, the method is performed in vivo.

In one embodiment, the TBAP compound is provided in the form of a pharmaceutically acceptable composition.

Any type of cell may be treated, including adipose, lung, gastrointestinal (including, e.g., bowel, colon), breast (mammary), ovarian, prostate, liver (hepatic), kidney (renal), bladder, pancreas, brain, and skin.

For example, a sample of cells may be grown in vitro and a compound brought into contact with said cells, and the effect of the compound on those cells observed. As an example of "effect," the morphological status of the cells (e.g., alive or dead, etc.) may be determined. Where the compound is found to exert an influence on the cells, this may be used as a prognostic or diagnostic marker of the efficacy of the compound in methods of treating a patient carrying cells of the same cellular type.

Use in Methods of Inhibiting Cell Proliferation, Etc.

The TBAP compounds described herein, e.g., (a) regulate (e.g., inhibit) cell proliferation; (b) inhibit cell cycle progression; (c) promote apoptosis; or (d) a combination of one or more of these.

One aspect of the present invention pertains to a method of regulating (e.g., inhibiting) cell proliferation (e.g., proliferation of a cell), inhibiting cell cycle progression, promoting apoptosis, or a combination of one or more these, in vitro or in vivo, comprising contacting a cell with an effective amount of a TBAP compound, as described herein.

In one embodiment, the method is a method of regulating (e.g., inhibiting) cell proliferation (e.g., proliferation of a cell), in vitro or in vivo, comprising contacting a cell with an effective amount of a TBAP compound, as described herein.

In one embodiment, the method is performed in vitro.

In one embodiment, the method is performed in vivo.

In one embodiment, the TBAP compound is provided in the form of a pharmaceutically acceptable composition.

Any type of cell may be treated, including lung, gastrointestinal (including, e.g., bowel, colon), breast (mammary), ovarian, prostate, liver (hepatic), kidney (renal), bladder, pancreas, brain, and skin.

One of ordinary skill in the art is readily able to determine whether or not a candidate compound regulates (e.g., inhibits) cell proliferation, etc. For example, assays which may conveniently be used to assess the activity offered by a particular compound are described herein.

For example, a sample of cells (e.g., from a tumour) may be grown in vitro and a compound brought into contact with said cells, and the effect of the compound on those cells observed. As an example of "effect," the morphological status of the cells (e.g., alive or dead, etc.) may be determined. Where the compound is found to exert an influence on the cells, this may be used as a prognostic or diagnostic marker of the efficacy of the compound in methods of treating a patient carrying cells of the same cellular type.

Use in Methods of Therapy

Another aspect of the present invention pertains to a TBAP compound, as described herein, for use in a method of treatment of the human or animal body by therapy, for example, for use a method of treatment of a disorder (e.g., a disease) as described herein.

Use in the Manufacture of Medicaments

Another aspect of the present invention pertains to use of a TBAP compound, as described herein, in the manufacture of a medicament, for example, for use in a method of treatment, for example, for use in a method of treatment of a disorder (e.g., a disease) as described herein.

In one embodiment, the medicament comprises the TBAP compound.

Methods of Treatment

Another aspect of the present invention pertains to a method of treatment, for example, a method of treatment of a disorder (e.g., a disease) as described herein, comprising administering to a subject in need of treatment a therapeutically-effective amount of a TBAP compound, as described herein, preferably in the form of a pharmaceutical composition.

Disorders Treated—Proliferative Disorders

In one embodiment (e.g., for use in methods of therapy, of use in the manufacture of medicaments, of methods of treatment), the treatment is treatment of a proliferative disorder.

The term "proliferative disorder," as used herein, pertains to an unwanted or uncontrolled cellular proliferation of excessive or abnormal cells which is undesired, such as neoplastic or hyperplastic growth.

In one embodiment, the treatment is treatment of: a proliferative disorder characterised by benign, pre-malignant, or malignant cellular proliferation.

In one embodiment, the treatment is treatment of: hyperplasia; a neoplasm; a tumour (e.g., a histocytoma, a glioma, an astrocyoma, an osteoma); cancer; psoriasis; a bone disease; a fibroproliferative disorder (e.g., of connective tissues); pulmonary fibrosis; atherosclerosis; or smooth muscle cell proliferation in the blood vessels (e.g., stenosis or restenosis following angioplasty).

Disorders Treated—Cancer

In one embodiment (e.g., of use in methods of therapy, of use in the manufacture of medicaments, of methods of treatment), the treatment is treatment of cancer.

In one embodiment, the treatment is treatment of cancer metastasis.

Included Among Cancers are:

(1) Carcinomas, including tumours derived from stratified squamous epithelia (squamous cell carcinomas) and tumours arising within organs or glands (adenocarcinomas). Examples include breast, colorectal, lung, pancreas, prostate, ovary.

(2) Sarcomas, including: osteosarcoma and osteogenic sarcoma (bone); chondrosarcoma (cartilage); leiomyosarcoma (smooth muscle); rhabdomyosarcoma (skeletal muscle); mesothelial sarcoma and mesothelioma (membranous lining of body cavities); fibrosarcoma (fibrous tissue); angiosarcoma and haemangioendothelioma (blood vessels); liposarcoma (adipose tissue); glioma and astrocytoma (neurogenic connective tissue found in the brain); myxosarcoma (primitive embryonic connective tissue); mesenchymous and mixed mesodermal tumour (mixed connective tissue types).

(3) Myeloma.

(4) Melanomas including, e.g., superficial spreading melanoma, nodular melanoma, lentigo malignant melanoma, acral melanoma, and uveal melanoma.

(5) Haematopoietictumours, including: myelogenous and granulocytic leukaemia (malignancy of the myeloid and granulocytic white blood cell series); lymphatic, lymphocytic, and lymphoblastic leukaemia (malignancy of the lymphoid and lymphocytic blood cell series); polycythaemia vera (also known as erythremia) (malignancy of various blood cell products, but with red cells predominating).

(6) Lymphomas, including: Hodgkin and Non-Hodgkin lymphomas.

(7) Mixed Types, including, e.g., adenosquamous carcinoma; mixed mesodermal tumour; carcinosarcoma; teratocarcinoma.

In one embodiment, the cancer is characterised by, or further characterised by, cancer stem cells.

In one embodiment, the treatment is treatment of cancer that is resistant to treatment with an antibody, e.g., a known antibody, e.g., a legislatively approved antibody. In one embodiment, the treatment is treatment of melanoma that is resistant to treatment with an antibody, e.g., a known antibody, e.g., a legislatively approved antibody. Examples of such antibodies which are known for treating melanoma include: antibodies that bind to CTLA-4 (cytotoxic T lymphocyte-associated antigen 4), such as ipilimumab (approved); antibodies that bind to PD-1 (programmed cell death 1 receptor), such as pembrolizumab (approved) and nivolumab (approved); antibodies that bind to PD-L1 (programmed death ligand 1), such as MEDI4736 (in clinical trials) and MPDL3280A (in clinical trials); antibodies and antibody-conjugates that bind to melanoma antigen glycoprotein NMB, such as glembatumumab vedotin (in clinical trials); antibodies that bind anti-tumor endothelial marker 1, such as ontuxizumab (in clinical trials); antibodies that bind to VEGF, such as bevacizumab, alone or in combination with standard chemotherapy or low-dose IFN-α2b (in clinical trials); antibodies that binds to ganglioside GD3, such as KW-2871 (in clinical trials); antibodies that bind Integrin isoforms, such as $\alpha_v\beta_1$, $\alpha_v\beta_3$, $\alpha_v\beta_5$, and $\alpha_v\beta_6$, such as intetumumab (in clinical trials).

The anti-cancer effect may arise through one or more mechanisms, including but not limited to, the regulation of cell proliferation, the inhibition of cell cycle progression, the inhibition of angiogenesis (the formation of new blood vessels), the inhibition of metastasis (the spread of a tumour from its origin), the inhibition of cell migration (the spread of cancer cells to other parts of the body), the inhibition of invasion (the spread of tumour cells into neighbouring normal structures), the promotion of apoptosis (programmed cell death), death by necrosis, or induction of death by autophagy. The compounds described herein may be used in the treatment of the cancers described herein, independent of the mechanisms discussed herein.

Disorders Treated—Inflammation

In one embodiment (e.g., for use in methods of therapy, of use in the manufacture of medicaments, of methods of treatment), the treatment is treatment of inflammation (e.g., an inflammatory disorder or reaction).

In one embodiment, the treatment is treatment of acute inflammation (e.g., mediated by acute infection).

In one embodiment, the treatment is treatment of chronic inflammation (e.g., mediated by chronic infection).

In one embodiment, the inflammatory disease is selected from inflammatory diseases of the lung (e.g., asthma; chronic obstructive pulmonary disease (COPD)); eye (e.g., uveitis); and gastrointestinal tract (e.g., Crohn's disease; ulcerative colitis).

In one embodiment, the inflammatory disease is selected from:
(i) lung diseases or disorders having an inflammatory component, such as cystic fibrosis, pulmonary hypertension, lung sarcoidosis, idiopathic pulmonary fibrosis, and, particularly, COPD (including chronic bronchitis and emphysema), asthma, and paediatric asthma;
(ii) skin diseases or disorders having an inflammatory component, such as atopic dermatitis, allergic dermatitis, contact dermatitis, and psoriasis;
(iii) nasal diseases or disorders having an inflammatory component, such as allergic rhinitis, rhinitis, and sinusitis;
(iv) eye diseases or disorders having an inflammatory component, such as conjunctivitis, allergic conjunctivitis, keratoconjunctivitis sicca (dry eye), glaucoma, diabetic retinopathy, macular oedema (including diabetic macular oedema), central retinal vein occlusion (CRVO), dry and/or wet age related macular degeneration (AM O), post-operative cataract inflammation, and, particularly, uveitis (including posterior, anterior and pan uveitis), corneal graft and limbal cell transplant rejection; and
(v) gastrointestinal diseases or disorders having an inflammatory component, such as gluten sensitive enteropathy (coeliac disease), eosinophilic eosophagitis, intestinal graft versus host disease, and, particularly, Crohn's disease and ulcerative colitis.

In one embodiment, the inflammatory disease is selected from: cystic fibrosis; pulmonary hypertension; lung sarcoidosis; idiopathic pulmonary fibrosis; chronic obstructive pulmonary disease (COPD) (including chronic bronchitis and emphysema); asthma; paediatric asthma; atopic dermatitis; allergic dermatitis; contact dermatitis; psoriasis; allergic rhinitis; rhinitis; sinusitis; conjunctivitis; allergic conjunctivitis; keratoconjunctivitis sicca (dry eye); glaucoma; diabetic retinopathy; macular oedema (including diabetic macular oedema); central retinal vein occlusion (CRVO); dry and/or wet age related macular degeneration (AMD); postoperative cataract inflammation; uveitis (including posterior, anterior, and pan uveitis); corneal graft and limbal cell transplant rejection; gluten sensitive enteropathy (coeliac disease); eosinophilic eosophagitis; intestinal graft versus host disease; Crohn's disease; and ulcerative colitis.

In one embodiment, the inflammatory disease is asthma or COPD.

In one embodiment, the inflammatory disease is uveitis, Crohn's disease, or ulcerative colitis.

Disorders Treated—Immunological Disorders

In one embodiment (e.g., for use in methods of therapy, of use in the manufacture of medicaments, of methods of treatment), the treatment is treatment of an immunological disorder.

In one embodiment, the treatment is treatment of an allergy.

In one embodiment, the treatment is treatment of an inflammatory airways disease, such as asthma.

In one embodiment, the treatment is treatment of allergic contact dermatitis.

In one embodiment, the treatment is treatment of a disease of the immune system.

In one embodiment, the treatment is treatment of an autoimmune disease, e.g., rheumatoid arthritis; systemic lupus erythematosus (lupus); inflammatory bowel disease (IBD); multiple sclerosis (MS); type 1 diabetes mellitus; Guillain-Barre syndrome; psoriasis; Graves' disease; Hashimoto's thyroiditis; myasthenia gravis; vasculitis; an immune deficiency disease; severe combined immune deficiency (SCID); common variable immune deficiency (CVID); human immunodeficiency virus (HIV); acquired immune deficiency syndrome (AIDS); drug-induced immune deficiency; or graft versus host syndrome.

Disorders Treated—Viral Infection

In one embodiment (e.g., for use in methods of therapy, of use in the manufacture of medicaments, of methods of treatment), the treatment is treatment of a viral infection.

In one embodiment, the treatment is treatment of a viral infection by:
(Group I:) a dsDNA virus, e.g., an adenovirus, a herpesvirus, a poxvirus;
(Group II:) a ssDNA virus, e.g., a parvovirus;
(Group III:) a dsRNA virus, e.g., a reovirus;

(Group IV:) a (+)ssRNA virus, e.g., a picornavirus, a togavirus;

(Group V:) a (−)ssRNA virus, e.g., an orthomyxovirus, a rhabdovirus;

(Group VI:) a ssRNA-RT virus, e.g., a retrovirus; or (Group VII:) a dsDNA-RT virus, e.g., a hepadnavirus.

As used above: ds: double strand; ss: +strand; (+)ssRNA: +strand RNA; (−)ssRNA: -strand RNA; ssRNA-RT: (+strand)RNA with DNA intermediate in life-cycle.

In one embodiment, the treatment is treatment of: human immunodeficiency virus (HIV); hepatitis B virus (HBV); hepatitis C virus (HCV); human papilloma virus (HPV); cytomegalovirus (CMV); or Epstein-Barr virus (EBV); human herpesvirus 8 (HHV) associated with Kaposi sarcoma; Coxsackievirus B3; Borna virus; influenza virus.

Disorders Treated—Fibrotic Disorders

In one embodiment (e.g., for use in methods of therapy, of use in the manufacture of medicaments, of methods of treatment), the treatment is treatment of a fibrotic disorder (e.g., a disorder characterised by excess fibrosis, e.g., an excess of fibrous connective tissue in a tissue or organ, e.g., triggered by a reparative or reactive process, e.g., in response to injury (e.g., scarring, healing) or excess fibrotic tissue arising from a single cell line (e.g., fibroma)).

In one embodiment, the treatment is treatment of:

(for lungs:) pulmonary fibrosis; pulmonary fibrosis secondary to cystic fibrosis; idiopathic pulmonary fibrosis; coal worker's progressive massive fibrosis;

(for liver:) cirrhosis;

(for heart:) endomyocardial fibrosis; old myocardial infarction; atrial fibrosis;

(for mediastinum:) mediastinal fibrosis;

(for bone:) myelofibrosis;

(for retroperitoneum:) retroperitoneal fibrosis;

(for skin:) nephrogenic systemic fibrosis; keloid scarring; systemic sclerosis; scleroderma;

(for intestines:) Crohn's disease;

(for connective tissue:) arthrofibrosis; or capsulitis.

Disorders Treated—Disorders Ameliorated by the Inhibition of Mutant BRAF

In one embodiment (e.g., for use in methods of therapy, of use in the manufacture of medicaments, of methods of treatment), the treatment is treatment of a disorder (e.g., a disease) (e.g., a proliferative disorder, e.g., cancer) that is associated with a mutated form of RAF (e.g., BRAF), such as, for example, the mutations described in Davies et al., 2002; Wan et al., 2004; and Stratton et al., 2003.

In one embodiment (e.g., for use in methods of therapy, of use in the manufacture of medicaments, of methods of treatment), the treatment is treatment of a disorder (e.g., a disease) (e.g., a proliferative disorder, e.g., cancer) that is ameliorated by the inhibition of RAF (e.g., BRAF).

In one embodiment, the treatment is treatment of: a disorder (e.g., a disease) which is characterised by cells which overexpress mutant RAF (e.g., BRAF) (e.g., as compared to corresponding normal cells; e.g., wherein the overexpression is by a factor of 1.5, 2, 3, 5, 10, 20 or 50).

Proliferative Disorders:

In one embodiment, the treatment is treatment of: malignant melanoma; colorectal carcinoma; metastatic colorectal carcinoma; follicular thyroid cancer; insular thyroid cancer; papillary thyroid cancer; ovarian carcinoma; low grade ovarian carcinoma; non-small cell lung cancer; hairy cell leukemia; cholangiocarcinoma; pediatric low-grade glioma (e.g., pilocytic astrocytoma; ganglioglioma; pleomorphic xanthoastrocytoma); multiple myeloma; or medullary carcinoma of the pancreas. In one embodiment, the treatment is treatment of: pancreatic ductal adenocarcinoma.

In one embodiment, the treatment is treatment of a disorder (e.g., a disease) that is associated with a mutated form of RAF (e.g., BRAF, CRAF, etc.) but that is resistant to treatment with a known (e.g., approved) RAF (e.g., BRAF, CRAF, etc.) inhibitor. Examples of known (e.g., approved) BRAF inhibitors include vemurafenib (PLX4032, RG7204, Zelboraf) (approved) and dabrafenib (GSK-2118436) (approved).

In one embodiment, the treatment is treatment of a disorder (e.g., a disease) that is associated with a mutated form of RAF (e.g., BRAF, CRAF, etc.) but that is resistant to treatment with a combination of a known (e.g., approved) RAF (e.g., BRAF, CRAF, etc.) inhibitor and a known (e.g., approved) MEK inhibitor. Examples of MEK inhibitors include: trametinib (GSK 1120212) (approved); selumetinib (AZD6244) (in clinical trials); PD 325901 (in clinical trials); cobimetinib (GDC 0973, XL 518) (in clinical trials); and CI 1040 (PD184352) (in clinical trials).

In one embodiment, the treatment is treatment of: BRAF-mutant melanoma intrinsically resistant to vemurafenib; BRAF-mutant melanoma that acquires resistance to vemurafenib treatment; BRAF-mutant melanoma intrinsically resistant to dabrafenib; BRAF-mutant melanoma that acquires resistance to dabrafenib treatment; or BRAF-mutant melanoma that acquires resistance to a combination of a BRAF inhibitor and a MEK inhibitor (e.g., dabrafenib and trametinib).

Other Disorders:

In one embodiment, the treatment is treatment of: Langerhans cell histiocytosis (LCH) or Erdheim-Chester disease.

Disorders Treated—Disorders Ameliorated by the Inhibition of Both BRAF and CRAF

Cancers with, for example, activating mutations of RAS, RAF, and EGFR or overexpression of RAS, RAF, and EGFR, including any of the isoforms thereof, may be particularly sensitive to panRAF (e.g., CRAF and BRAF) inhibition. Cancers with other abnormalities leading to an up-regulated RAF-MEK-ERK pathway signal may also be particularly sensitive to treatment with inhibitors to panRAF (e.g., CRAF and BRAF) activity. Examples of such abnormalities include constitutive activation of a growth factor receptor; overexpression of one or more growth factor receptors; overexpression of one or more growth factors; KSR-mediated pathway activation; and BRAF or CRAF gene fusions.

In one embodiment (e.g., for use in methods of therapy, of use in the manufacture of medicaments, of methods of treatment), the treatment is treatment of a disorder (e.g., a disease) (e.g., a proliferative disorder, e.g., cancer) that is ameliorated by the inhibition of both BRAF and CRAF.

In one embodiment, the treatment is treatment of: a disorder (e.g., a disease) (e.g., a proliferative disorder, e.g., cancer) which is characterised by constitutive activation of a growth factor receptor; overexpression of one or more growth factor receptors (e.g., as compared to corresponding normal cells; e.g., wherein the overexpression is by a factor of 1.5, 2, 3, 5, 10, 20 or 50); overexpression of one or more growth factors (e.g., as compared to corresponding normal cells; e.g., wherein the overexpression is by a factor of 1.5, 2, 3, 5, 10, 20 or 50); and/or BRAF and/or CRAF activating gene fusions.

In one embodiment, the treatment is treatment of: a disorder (e.g., a disease) (e.g., a proliferative disorder, e.g., cancer) that is characterised by one or more or all of:

(a) activating mutants of RAS and/or RAF;
(b) up-regulation of RAS and/or RAF;
(c) up-regulation of RAF-MEK-ERK pathway signals; and
(d) up-regulation of growth factor receptors (e.g., ERBB2 and EGFR).

In one embodiment, the treatment is treatment of: an inflammatory disease; an infection; an autoimmune disorder; stroke; ischaemia; a cardiac disorder; a neurological disorder; a fibrogenetic disorder, a proliferative disorder; a hyperproliferative disorder; a non-cancer hyperproliferative disorder; a tumour; leukaemia; a neoplasm; cancer; carcinoma; a metabolic disease; a malignant disease; vascular restenosis; psoriasis; atherosclerosis; rheumatoid arthritis; osteoarthritis; heart failure; chronic pain; neuropathic pain; dry eye; closed angle glaucoma; or wide angle glaucoma.

Disorders Treated—Disorders Associated with RAS Mutations and/or MAPK Pathway Activation In one embodiment (e.g., for use in methods of therapy, of use in the manufacture of medicaments, of methods of treatment), the treatment is treatment of a disorder (e.g., a disease) that is associated with a RAS (e.g., KRAS, NRAS, HRAS) mutation and/or MAPK pathway activation (e.g., hyperactivity of the MAPK pathway).

Proliferative Disorders:

In one embodiment, the treatment is treatment of a proliferative disorder (e.g., cancer) that is associated with a RAS (e.g., KRAS, NRAS, HRAS) mutation and/or MAPK pathway activation (e.g., hyperactivity of the MAPK pathway).

In one embodiment, the treatment is treatment of: non-small cell lung carcinoma; colorectal cancer; metastatic colorectal cancer; hepatocellular carcinoma; pancreatic adenocarcinoma; malignant melanoma; a haematological malignancy (e.g., juvenile myelomonocytic leukaemia (JMML); chronic myelomonocytic leukaemia (CMML); myelodysplastic syndrome (MDS); acute lymphoblastic leukaemia (ALL); multiple myeloma (MM); Burkitt's lymphoma; Hodgkin's lymphoma); Type I epithelial ovarian cancer; primary peritoneal cancer; biliary tract adenocarcinoma; follicular thyroid cancer; undifferentiated papillary thyroid cancer; soft tissue sarcoma (e.g., angiosarcoma; leiomyosarcoma; rhabdomyosarcoma; myxoma; malignant fibrous histiocytoma); neurofibromatosis type 1 (NF1); inoperable plexiform neurofibromas (PN); uveal melanoma; ciliary body melanoma; choroid melanoma; iris melanoma; metastatic intraocular melanoma; adrenocortical carcinoma; renal cancer; seminoma; bladder cancer; endometrial cancer; cervical cancer; neuroblastoma; stomach adenocarcinoma; head and neck squamous cell carcinoma; or prostate cancer.

Other Disorders:

In one embodiment, the treatment is treatment of: transplant (e.g., xenograft; skin; limb; organ; bone marrow) rejection; osteoarthritis; rheumatoid arthritis; cystic fibrosis; a complication of diabetes (e.g., diabetic retinopathy; diabetic nephropathy); hepatomegaly; cardiomegaly; Noonan syndrome; cardiofaciocutaneous syndrome; hypertrophic cardiomyopathy; stroke (e.g., acute focal ischemic stroke; global cerebral ischemia); heart failure; septic shock; asthma; chronic obstructive pulmonary disorder; Alzheimer's disease; chronic pain (e.g., idiopathic pain; pain associated with chronic alcoholism, vitamin deficiency, uraemia, or hypothyroidism; chronic pain associated with inflammation; chronic post-operative pain); or neuropathic pain (e.g., associated with inflammation; post-operative pain; phantom limb pain; burn pain; gout; trigeminal neuralgia; acute herpetic pain; post-herpetic pain; causalgia; diabetic neuropathy; plexus avulsion; neuroma; vasculitis; viral infection; crush injury; constriction injury; tissue injury; limb amputation; nerve injury between the peripheral nervous system and the central nervous system).

Disorders Treated—Disorders Ameliorated by the Inhibition of SRC

In one embodiment (e.g., for use in methods of therapy, of use in the manufacture of medicaments, of methods of treatment), the treatment is treatment of a disorder (e.g., a disease) that is ameliorated by the inhibition of SRC.

In one embodiment, the treatment is treatment of: a disorder (e.g., a disease) (e.g., a proliferative disorder) that is associated with SRC mutation; SRC overexpression (e.g., as compared to corresponding normal cells; e.g., wherein the overexpression is by a factor of 1.5, 2, 3, 5, 10, 20 or 50); or upstream pathway activation of SRC (e.g., by elevated RTK signalling).

In one embodiment, the treatment is treatment of: endometrial cancer; non-small cell lung carcinoma; malignant pleural mesothelioma; malignant melanoma; chronic myeloid leukaemia (e.g., imatinib-resistant); bone metastases; hormone-resistant prostate cancer; recurrent prostate cancer; recurrent osteosarcoma; acute lymphoblastic leukaemia; colorectal cancer; metastatic colorectal cancer; breast cancer; ovarian cancer; recurrent or metastatic head and neck cancer (e.g., metastatic squamous neck cancer with occult primary squamous cell carcinoma; recurrent metastatic squamous neck cancer with occult primary; recurrent squamous cell carcinoma of the hypopharynx; recurrent squamous cell carcinoma of the larynx; recurrent squamous cell carcinoma of the lip and oral cavity; recurrent squamous cell carcinoma of the nasopharynx; recurrent squamous cell carcinoma of the oropharynx; recurrent squamous cell carcinoma of the paranasal sinus and nasal cavity; recurrent verrucous carcinoma of the larynx; recurrent verrucous carcinoma of the oral cavity; squamous cell carcinoma of the hypopharynx; squamous cell carcinoma of the larynx; squamous cell carcinoma of the lip and oral cavity; squamous cell carcinoma of the nasopharynx; squamous cell carcinoma of the oropharynx; squamous cell carcinoma of the paranasal sinus and sasal cavity; verrucous carcinoma of the larynx; verrucous carcinoma of the oral cavity; tongue cancer); recurrent skin cancer; squamous cell carcinoma of the skin; acute myelogenous leukemia; glioblastoma; or diffuse intrinsic pontine glioma.

Disorders Treated—Disorders Ameliorated by the Inhibition of p38

In one embodiment (e.g., for use in methods of therapy, of use in the manufacture of medicaments, of methods of treatment), the treatment is treatment of a disorder (e.g., a disease) that is ameliorated by the inhibition of p38 (e.g., p38α, p38γ).

In one embodiment, the treatment is treatment of: a disorder (e.g., a disease) (e.g., a proliferative disorder) that is associated with p38 (e.g., p38α, p38γ) mutation; p38 (e.g., p38α, p38γ) overexpression (e.g., as compared to corresponding normal cells; e.g., wherein the overexpression is by a factor of 1.5, 2, 3, 5, 10, 20 or 50); or upstream pathway activation of p38 (e.g., p38α, p38γ).

Proliferative Disorders:

In one embodiment, the treatment is treatment of: ovarian cancer; oral cavity squamous cell cancer; multiple myeloma; bone marrow neoplasms; or myelodysplastic syndrome.

Other Disorders:

In one embodiment, the treatment is treatment of: an inflammatory disorder characterized by T-cell proliferation (e.g., T-cell activation and growth).

In one embodiment, the treatment is treatment of: rheumatoid arthritis; osteoarthritis; psoriatic arthritis; Reiter's syndrome; traumatic arthritis; rubella arthritis; acute synovitis; gouty arthritis; or spondylitis.

In one embodiment, the treatment is treatment of: psoriasis; eczema; allergic rhinitis; allergic conjunctivitis; asthma; adult respiratory distress syndrome; acute lung injury (ALI); acute respiratory distress syndrome (ARDS); chronic pulmonary inflammation; chronic obstructive pulmonary disease; systemic cachexia; glomerulonephritis; chronic heart failure; atherosclerosis; acute coronary syndrome: cardiac ischemia; or myocardial infarction.

In one embodiment, the treatment is treatment of: endotoxaemia; toxic shock syndrome; inflammatory bowel disease; atherosclerosis; irritable bowel syndrome; Crohn's disease; ulcerative colitis; a bone resorption disease; osteoporosis; diabetes; reperfusion injury; graft versus host reaction; allograft rejection; sepsis; septic shock; endotoxic shock; Gram-negative sepsis; glomerulonephritis; restenosis; or thrombosis.

In one embodiment, the treatment is treatment of pain.

In one embodiment, the treatment is treatment of: chronic pain; neuromuscular pain; headache; cancer pain; acute or chronic inflammatory pain associated with osteoarthritis or rheumatoid arthritis; post-operative inflammatory pain; neuropathic pain; diabetic neuropathy; trigeminal neuralgia; post-hepatic neuralgia; inflammatory neuropathy; migraine pain; lumbosacral radiculopathy; dental pain; nerve trauma; or neural ischemia.

Disorders Treated—Disorders Ameliorated by the Inhibition of FGFR1

In one embodiment (e.g., for use in methods of therapy, of use in the manufacture of medicaments, of methods of treatment), the treatment is treatment of a disorder (e.g., a disease) that is ameliorated by the inhibition of FGFR1.

In one embodiment, the treatment is treatment of: a disorder (e.g., a disease) (e.g., a proliferative disorder) that is associated with FGFR1 mutation; FGFR1 overexpression (e.g., as compared to corresponding normal cells; e.g., wherein the overexpression is by a factor of 1.5, 2, 3, 5, 10, 20 or 50); or upstream pathway activation of FGFR1.

In one embodiment, the treatment is treatment of: breast cancer; squamous lung cancer; stomach cancer; urothelial carcinoma; multiple myeloma; 8p11 myeloproliferative syndrome; or hepatocellular carcinoma.

Disorders Treated—Disorders Ameliorated by the Inhibition of VEGFR-2 (KDR)

In one embodiment (e.g., for use in methods of therapy, of use in the manufacture of medicaments, of methods of treatment), the treatment is treatment of a disorder (e.g., a disease) that is ameliorated by the inhibition of VEGFR-2 (KDR).

In one embodiment, the treatment is treatment of: a disorder (e.g., a disease) (e.g., a proliferative disorder) that is associated with VEGFR-2 mutation; VEGFR-2 overexpression (e.g., as compared to corresponding normal cells; e.g., wherein the overexpression is by a factor of 1.5, 2, 3, 5, 10, 20 or 50); or upstream pathway activation of VEGFR-2.

In one embodiment, the treatment is treatment of: a disorder (e.g., a disease) that is characterised by increased production of VEGF (e.g., by either cancer cells or stromal cells).

Proliferative Disorders:

In one embodiment, the treatment is treatment of: pancreatic cancer; non-small cell lung cancer (NSCLC); ovarian neoplasms; peritoneal neoplasms; fallopian tube neoplasms; lung cancer and associated pleural effusion; recurrent or metastatic squamous cell cancer of the head and neck; locally advanced nasopharyngeal carcinoma; glioblastoma (e.g., glioblastoma multiforme; giant cell glioblastoma); gliosarcoma; diffuse intrinsic pontine glioma; HIV-related kaposi sarcoma; multiple myeloma; renal cell carcinoma; metastatic gastric adenocarcinoma; acute myeloid leukemia (AML); hepatocellular carcinoma; dermatofibrosarcoma; medullary thyroid cancer (MTC); papillary thyroid cancer; follicular thyroid cancer; myelodysplastic syndrome; neurofibromatosis type 1; plexiform neurofibroma; spinal cord neurofibroma; breast cancer; biliary tract neoplasms; cervical cancer; prostate cancer; melanoma; bladder carcinoma; urethra carcinoma; ureter carcinoma; renal carcinoma; pelvis carcinoma; sarcoma; liposarcoma; colon cancer; osteosarcoma; synovial carcinoma; neuroblastoma; or rhabdomyosarcoma.

Other Disorders:

In one embodiment, the treatment is treatment of: atherosclerosis; obesity; neuropathic pain syndrome; age-related macular degeneration; diabetic retinopathy; diabetic macular oedema; or rheumatoid arthritis.

Disorders Treated—Disorders Ameliorated by the Inhibition of LCK

In one embodiment (e.g., for use in methods of therapy, of use in the manufacture of medicaments, of methods of treatment), the treatment is treatment of a disorder (e.g., a disease) that is ameliorated by the inhibition of LCK.

In one embodiment, the treatment is treatment of: a disorder (e.g., a disease) that is associated with LCK mutation; LCK overexpression (e.g., as compared to corresponding normal cells; e.g., wherein the overexpression is by a factor of 1.5, 2, 3, 5, 10, 20 or 50); or upstream pathway activation of LCK.

In one embodiment, the treatment is treatment of: an immunologic disease or pathological condition involving an immunologic component.

In one embodiment, the treatment is treatment of: rheumatoid arthritis; inflammatory bowel disease (e.g., ulcerative colitis; Crohn's disease); psoriasis; psoriasis arthritis; tissue or organ transplant rejection (including, e.g., prevention of); acute or chronic graft-versus-host disease; allograft rejection; xenograft rejection; allergic asthma; multiple sclerosis; type 1 diabetes; lung fibrosis; or a hypersensitivity reaction of the skin.

Treatment

The term "treatment," as used herein in the context of treating a disorder, pertains generally to treatment of a human or an animal (e.g., in veterinary applications), in which some desired therapeutic effect is achieved, for example, the inhibition of the progress of the disorder, and includes a reduction in the rate of progress, a halt in the rate of progress, alleviation of symptoms of the disorder, amelioration of the disorder, and cure of the disorder. Treatment as a prophylactic measure (i.e., prophylaxis) is also included. For example, use with patients who have not yet developed the disorder, but who are at risk of developing the disorder, is encompassed by the term "treatment."

For example, treatment includes the prophylaxis of cancer, reducing the incidence of cancer, alleviating the symptoms of cancer, etc.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Combination Therapies

The term "treatment" includes combination treatments and therapies, in which two or more treatments or therapies are combined, for example, sequentially or simultaneously. For example, the compounds described herein may also be used in combination therapies, e.g., in conjunction with other agents. Examples of treatments and therapies include chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; photodynamic therapy; gene therapy; and controlled diets.

One aspect of the present invention pertains to a compound as described herein, in combination with one or more (e.g., 1, 2, 3, 4, etc.) additional therapeutic agents, as described below.

The particular combination would be at the discretion of the physician who would select dosages using his common general knowledge and dosing regimens known to a skilled practitioner.

The agents (i.e., the compound described herein, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., the compound described here, plus one or more other agents) may be formulated together in a single dosage form, or alternatively, the individual agents may be formulated separately and presented together in the form of a kit, optionally with instructions for their use.

Examples of additional agents/therapies that may be co-administered/combined with treatment with the TBAP compounds described herein include the following: antimetabolites; alkylating agents; spindle poisons; topoisomerase inhibitors; DNA binding agents; kinase inhibitors; therapeutic antibodies; PARP inhibitors; NAD metabolism inhibitors; metabolic inhibitors; targeted agents; endocrine agents; etc.

Other Uses

The TBAP compounds described herein may also be used as cell culture additives to inhibit RAF (e.g., BRAF, CRAF, etc.).

The TBAP compounds described herein may also be used as part of an in vitro assay, for example, in order to determine whether a candidate host is likely to benefit from treatment with the compound in question.

The TBAP compounds described herein may also be used as a standard, for example, in an assay, in order to identify other active compounds, other RAF (e.g., BRAF, CRAF, etc.) inhibitors, etc.

Kits

One aspect of the invention pertains to a kit comprising (a) a TBAP compound as described herein, or a composition comprising a TBAP compound as described herein, e.g., preferably provided in a suitable container and/or with suitable packaging; and (b) instructions for use, e.g., written instructions on how to administer the compound or composition.

The written instructions may also include a list of indications for which the active ingredient is a suitable treatment.

Routes of Administration

The TBAP compound or pharmaceutical composition comprising the TBAP compound may be administered to a subject by any convenient route of administration, whether systemically/peripherally or topically (i.e., at the site of desired action).

Examples of routes of administration include oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus.

In one preferred embodiment, the subject/patient is a human.

Formulations

While it is possible for a TBAP compound to be administered alone, it is preferable to present it as a pharmaceutical formulation (e.g., composition, preparation, medicament) comprising at least one TBAP compound, as described herein, together with one or more other pharmaceutically acceptable ingredients well-known to those skilled in the art, including pharmaceutically acceptable carriers, diluents, excipients, adjuvants, fillers, buffers, preservatives, antioxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising mixing at least one TBAP compound, as described herein, together with one or more other pharmaceutically acceptable ingredients well-known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences*, 18th edition, Mack Publishing Company, Easton, Pa., 1990; and *Handbook of Pharmaceutical Excipients*, 5th edition, 2005.

The formulations may be prepared by any methods well-known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The compound may be dissolved in, suspended in, or mixed with one or more other pharmaceutically acceptable ingredients. The compound may be presented in a liposome or other microparticulate which is designed to target the compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the compound in a flavored basis, usually sucrose and acacia or tragacanth. Pastilles typically comprise the compound in an inert matrix, such as gelatin and glycerin, or sucrose and acacia. Mouthwashes typically comprise the compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprise a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the compound is dissolved or suspended in a suitable carrier, especially an aqueous solvent for the compound.

Formulations suitable for rectal administration may be presented as a suppository with a suitable base comprising, for example, natural or hardened oils, waxes, fats, semiliquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additionally contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/mL to about 10 µg/mL, for example from about 10 ng/mL to about 1 µg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the TBAP compounds, and compositions comprising the TBAP compounds, can vary from patient to patient. Determining the optimal dosage will generally involve the balancing of the level of therapeutic benefit against any risk or deleterious side effects. The selected dosage level will depend on a variety of factors including the activity of the particular TBAP compound, the route of administration, the time of administration, the rate of excretion of the TBAP compound, the duration of the treatment, other drugs, compounds, and/or materials used in combination, the severity of the disorder, and the species, sex, age, weight, condition, general health, and prior medical history of the patient. The amount of TBAP compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well-known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the TBAP compound is in the range of about 10 µg to about 250 mg (more typically about 100 µg to about 25 mg) per kilogram body weight of the subject per day. Where the compound is a salt, an ester, an amide, a prodrug, or the like, the amount administered is calculated on the basis of the parent compound and so the actual weight to be used is increased proportionately.

Chemical Synthesis

All starting materials, reagents and solvents for reactions were reagent grade and used as purchased. Chromatography solvents were HPLC grade and were used without further purification. Reactions were monitored by thin layer chromatography (TLC) analysis using Merck silica gel 60 F-254 thin layer plates. Flash column chromatography was carried out on Merck silica gel 60 (0.015-0.040 mm) or in disposable Isolute Flash Si and Si II silica gel columns. LCMS analyses were performed on a Micromass LCT/Water's Alliance 2795 HPLC system with a Discovery 5 µm, C18, 50 mm×4.6 mm i.d. column from Supelco at a temperature of 22° C. using the following solvent systems: Solvent A: Methanol; Solvent B: 0.1% formic acid in water at a flow rate of 1 mL/min. Gradient starting with 10% A/90% B (by volume) from 0-0.5 minutes then 10% A/90% B to 90% A/10% B from 0.5 minutes to 6.5 minutes and continuing at 90% A/10% B up to 10 minutes. From 10-10.5 minutes the gradient reverted back to 10% A/90% where the concentrations remained until 12 minutes. UV detection was at 254 nm and ionisation was positive or negative ion electrospray. Molecular weight scan range is 50-1000. Samples were supplied as 1 mg/mL in DMSO or methanol with 3 µL injected on a partial loop fill. NMR spectra were recorded in DMSO-d on a Bruker Advance 500 MHz spectrometer.

Part (I): N-Arylation of Pyrazolecarboxylate Esters
Method A:

Ethyl, 3-tert-butyl-1H-pyrazole-5-carboxylate (1 equiv.), the desired boronic acid (2 equiv.), copper (II) acetate (1.5 equiv) and dry DMF were added under stirring to give a blue solution. Dry pyridine (2 equiv.) was added, upon which the colour turned to green, followed by a spoonful of oven-dried, powdered 4 Å (0.4 nm) molecular sieves. The mixture was stirred at room temperature under an argon atmosphere until reaction completion, as verified by LC-MS. After reaction completion, the mixture was diluted with AcOEt and NH$_4$Cl solution. The organic phase was isolated, washed with NH$_4$Cl solution, sat. aq. NaHCO$_3$, dried (MgSO$_4$ with Cu-catch resin), filtered, and evaporated to give an oily substance, which in some cases was further purified by column chromatography.

Synthesis 1

Ethyl, 3-tert-butyl-1-(3-methoxyphenyl)-1H-pyrazole-5-carboxylate

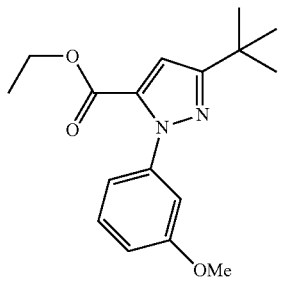 [SMILES: CCOC(=O)c1cc(C(C)(C)C)nn1-c1cccc(OC)c1]

Method A was used with ethyl 3-tert-butyl-1H-pyrazole-5-carboxylate (320 mg, 1.631 mmol) and 3-methoxyphenyl boronic acid (307 mg, 2.020 mmol). The reaction was completed after stirring at room temperature for 22 hours. After workup, the resulting yellow oil was dissolved in DCM/hexane and was loaded onto a 50 g SNAP column, which was eluted with 2→20% (by volume) EtOAc in hexane. The title compound was obtained as a colourless oil.

Yield: 462 mg (94%, 92% pure). $^1$H-NMR (DMSO-d$_6$), δ (ppm), J (Hz): 1.17 (t, 3H, $^3J_{HH}$=7.1, CH$_3$), 1.30 (s, 9H, tert-Bu), 3.79 (s, 3H, OCH$_3$), 4.17 (q, 2H, $^3J_{HH}$=7.1, OH$_2$CH$_3$), 6.98 (m, 4H, ArH), 7.36 (t, 1H, $^3J_{HH}$=8.1, ArH). LC-MS (2.79 min): m/z calcd. for C$_{17}$H$_{22}$N$_2$O$_3$ [M+H]$^+$: 303.1; found: 303.2.

Synthesis 2

Ethyl, 3-tert-butyl-1-(3-trifluoromethylphenyl)-1H-pyrazole-5-carboxylate

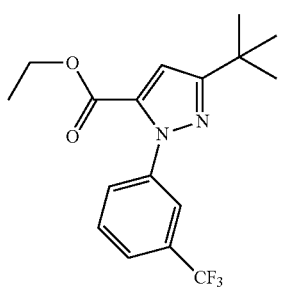 [SMILES: CCOC(=O)c1cc(C(C)(C)C)nn1-c1cccc(C(F)(F)F)c1]

Method A was used with ethyl, 3-tert-butylpyrazole-5-carboxylate (320 mg, 1.60 mmol), and 3-trifluoromethylphenyl boronic acid (307 mg, 1.60 mmol). After 20 hours, the reaction mixture was diluted with AcOEt (20 mL), washed with 2×20 mL water, NaHCO$_3$ (20 mL, conc.) and finally with 20 mL brine. The organic layer was dried (MgSO$_4$) and evaporated to dryness to give an oil (417 mg). The compound was used for the subsequent hydrolysis step without further purification.

Synthesis 3

Ethyl, 3-tert-butyl-1-(3-methylphenyl)-1H-pyrazole-5-carboxylate

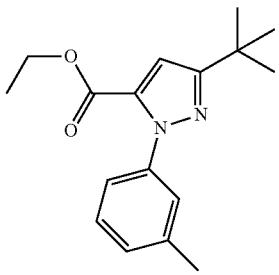 [SMILES: CCOC(=O)c1cc(C(C)(C)C)nn1-c1cccc(C)c1]

Method A was used with ethyl, 3-tert-butylpyrazole-5-carboxylate (320 mg, 1.60 mmol), and 3-methylphenyl boronic acid (218 mg, 1.60 mmol). After 20 hours, the reaction mixture was diluted with AcOEt (20 mL), washed with 2×20 mL water, NaHCO$_3$ (20 mL; conc.) and finally with 20 mL brine. The organic layer was dried (MgSO$_4$) and evaporated to dryness to give an oil (466 mg). The compound was used in the subsequent hydrolysis step without further purification.

Synthesis 4

Ethyl, 3-tert-butyl-1-(3-fluorophenyl)-1H-pyrazole-5-carboxylate

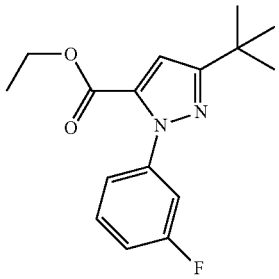 [SMILES: CCOC(=O)c1cc(C(C)(C)C)nn1-c1cccc(F)c1]

Method A was used with ethyl, 3-tert-butylpyrazole-5-carboxylate (320 mg, 1.60 mmol), and 3-fluorophenyl boronic acid (224 mg, 1.60 mmol). After 20 hours, the reaction mixture was diluted with AcOEt (20 mL), washed with 2×20 mL water, NaHCO$_3$ (20 mL; conc.) and finally with 20 mL brine. The organic layer was dried (MgSO$_4$) and evaporated to dryness to give an oil (463 mg). The compound was used in the subsequent hydrolysis step without further purification.

Synthesis 5

Ethyl, 3-tert-butyl-1-(2-methoxypyridin-4-yl)-1H-pyrazole-5-carboxylate

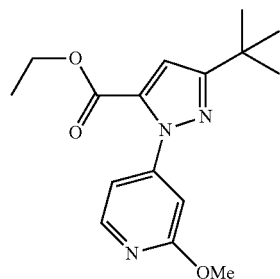 [SMILES: CCOC(=O)c1cc(C(C)(C)C)nn1-c1ccnc(OC)c1]

Method A was used with ethyl, 3-tert-butylpyrazole-5-carboxylate (202 mg, 1.03 mmol), and 2-methoxypyridin-4-yl boronic acid (208 mg, 1.360 mmol). Purification with 2→50% (by volume) EtOAc in hexane gave the title compound as a colorless oil.

Yield: 243 mg (59%). $^1$H-NMR (DMSO-d$_5$), δ (ppm), J (Hz): 1.22 (t, 3H, $^3J_{HH}$=7.1, CH$_3$), 1.29 (s, 9H, tert-Bu), 3.90 (s, 3H, OCH$_3$), 4.23 (q, 2H, $^3J_{HH}$=7.1, OCH$_2$CH$_3$), 6.94 (d, 1H, $^3J_{HH}$=1.7, PyrH), 7.07 (s, 1H, ArH), 7.13 (dd, 1H, $^3J_{HH}$=5.6, 1.7, PyrH), 8.23 (d, 1H, $^3J_{HH}$=5.6, PyrH). LC-MS (2.83 min): m/z calcd. for C$_{16}$H$_{21}$N$_3$O$_3$ [M+H]$^+$: 304.1; found: 303.1.

Part (II): Ethyl Ester Hydrolysis

Method B.

The appropriate 1-substituted ethyl, 3-tert-butyl-1H-pyrazole-5-carboxylate (1 equiv.) was dissolved in a 4:1:1 mixture of THF/MeOH/H$_2$O, lithium hydroxide monohydrate (1.1 equiv.) was added and the colourless mixture was stirred for 16 hours at room temperature. The volatiles were subsequently evaporated, and the resulting solid was re-dissolved in H$_2$O and the pH of the solution was adjusted to 1 with 10% aqueous HCl. The resulting milky mixture was extracted with EtOAc two times and the combined organic fraction was washed with brine, dried, and concentrated to dryness to give a white crystalline solid.

Method C.

The appropriate 1-substituted ethyl, 3-tert-butylpyrazole-5-carboxylate (1 equiv.), was refluxed for 30 minutes in 10 mL EtOH and 3 mL NaOH solution (2 M). After cooling at room temperature, the reaction mixture was neutralised to pH 4.0 (AcOH), diluted with 20 mL water, and extracted with AcOEt. The organic layer was washed with 2×20 mL water, dried (MgSO$_4$), and evaporated to dryness and the residue thus obtained was purified using a Biotage Isolera system.

Synthesis 6

3-tert-butyl-1-(3-methoxyphenyl)-1H-pyrazole-5-carboxylic acid

Using Method B with ethyl, 3-tert-butyl-1-(4-methoxyphenyl)-1H-pyrazole-5-carboxylate (442 mg, 1.345 mmol) yielded the title compound as white crystals.

Yield: 300 mg (81%). $^1$H-NMR (DMSO-d$_6$), δ (ppm), J (Hz): 1.29 (s, 9H, tert-Bu), 3.78 (s, 3H, OCH$_3$), 6.90 (s, 1H, ArH), 6.97 (m, 4H, ArH), 7.35 (t, 1H, $^3J_{HH}$=8.1, ArH), 13.14 (s, 1H, COOH). LC-MS (2.51 min): m/z calcd. for C$_{15}$H$_{18}$N$_2$O$_3$ [M+H]$^+$: 275.1; found: 275.0.

Synthesis 7

3-tert-butyl-1-(3-trifluoromethylphenyl)-1H-pyrazole-5-carboxylic acid

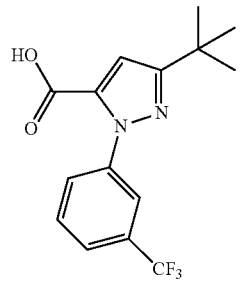 [SMILES: CC(C)(C)c1cc(C(=O)O)n(-c2cccc(C(F)(F)F)c2)n1]

Using Method C with crude ethyl, 3-tert-butyl-1-(3-trifluoromethylphenyl)-1H-pyrazole-5-carboxylate (471 mg), a solid product was obtained which was submitted to further purification using an Biotage Isolera System and a cyclohexane:EtOAc 1:1 mixture as eluent (isocratic mode) and gave the title compound.

Yield: 133 mg (26.6% over 2 steps). $^1$H NMR (DMSO), δ$_H$ (ppm), J (Hz): 1.31 (s, 9H, (CH$_3$)$_3$C), 6.99 (s, 1H, Pyr-H), 7.70 (t, 1H, Arom-H$_5$, J=7.7 Hz), 7.76-7.82 (m, 3H, Arom-H$_{2+4+e}$), 13.32 (s, 1H, Pyr-CO$_2$H). Ac. mass: (C$_{15}$H$_{16}$F$_3$N$_2$O$_2$) calc. 313.1157, found 313.1155.

Synthesis 8

3-tert-butyl-1-(3-methylphenyl)-1H-pyrazole-5-carboxylic acid

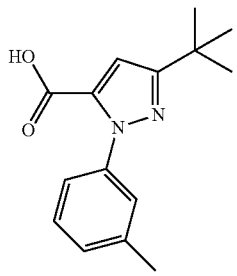 [SMILES: Cc1cccc(-n2nc(C(C)(C)C)cc2C(=O)O)c1]

Using Method C with crude ethyl, 3-tert-butyl-1-(3-methylphenyl)-1H-pyrazole-5-carboxylate (460 mg), the title compound was obtained after purification using an Biotage Isolera System and a cyclohexane:EtOAc 1:1 mixture as eluent (isocratic mode).

Yield: 101 mg (24.% over 2 steps). $^1$H NMR (DMSO), $\square_H$ (ppm), J (Hz): 1.29 (s, 9H, (C$\underline{H}_3$)$_3$C), 2.35 (s, 3H, 3-CH$_3$), 6.89 (s, 1H, Pyr-H), 7.18 (d, 1H, Arom-H$_2$, J=7.2 Hz), 7.20-7.24 (m, 2H, Arom-H$_{4+6}$), 7.32 (t, 1H, Arom-H$_5$, J=7.3 Hz), 13.09 (s, 1H, Pyr-CO$_2$$\underline{H}$). Ac. mass: (C$_{15}$H$_{18}$N$_2$O$_2$) calc. 258.1368, found 258.1373.

Synthesis 9

3-tert-butyl-1-(3-fluorophenyl)-1H-pyrazole-5-carboxylic acid

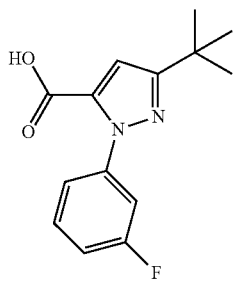 [SMILES: CC(C)(C)c1cc(C(=O)O)n(-c2cccc(F)c2)n1]

Using Method C with crude ethyl, 3-tert-butyl-1-(3-fluorophenyl)-1H-pyrazole-5-carboxylate (463 mg), the title compound was obtained. See, e.g., Springer et al., 2011.

Yield 166 mg (39.6% over 2 steps). $^1$H NMR (DMSO), $\square_H$ (ppm), J (Hz): 1.29 (s, 9H, (C$\underline{H}_3$)$_3$C), 6.95 (s, 1H, Pyr-H), 7.23-7.30 (m, 2H, Arom-H$_{4+5}$), 7.35 (d, 1H, Arom-H$_2$, J=9.8 Hz), 7.44-7.53 (m, 1H, Arom-H$_6$), 13.24 (s, 1H, Pyr-CO$_2$$\underline{H}$) Ac. Ac. mass: (C$_{14}$H$_{15}$FN$_2$O$_2$) calc. 262.1118, found 262.1117.

Synthesis 10

3-tert-butyl-1-(2-oxo-1,2-dihydropyridin-4-yl)-1H-pyrazole-5-carboxylic acid hydrochloride

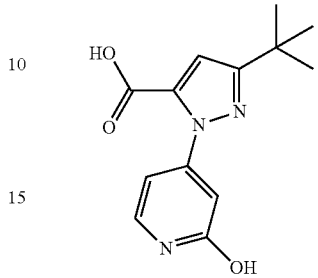

Method D:

Ethyl, 3-tert-butyl-1-(2-methoxypyridin-4-yl)-1H-pyrazole-5-carboxylate (110 mg, 0.363 mmol) was dissolved in 6M HCl in H$_2$O (4.5 mL, 27.00 mmol) and the colorless solution was heated to 90° C. for 48 h. All volatiles were subsequently evaporated and the resulting colorless oil was coevaporated with DCM (10 mL) and then with Et$_2$O (10 mL), which gave the title compound as a white solid.

Yield: 93 mg (98%). $^1$H-NMR (DMSO-d$_6$), δ (ppm), J (Hz): 1.28 (s, 9H, 9H, tert-Bu), 6.32 (d, 1H, J=1.9, ArH), 6.37 (dd, 1H, J=7.1, 1.9, ArH), 6.99 (s, 1H, ArH), 7.46 (d, 1H, J=7.1, ArH). LC-MS (2.14 min): m/z calcd. for C$_{13}$H$_{16}$N$_3$O$_3$ [M-Cl]$^+$: 262.1; found: 262.0;

Part (III): Formation of 5-aminopyrazoles

Synthesis 11

3-(tert-butyl)-1-(3-fluorophenyl)-1H-pyrazol-5-amine

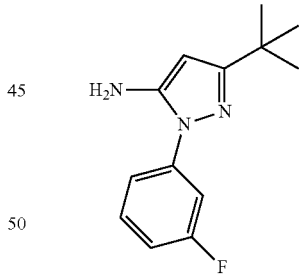

Method E:

A mixture of 4,4-dimethyl-3-oxopentane nitrile (77 g, 0.62 mol) and 3-fluorophenylhydrazine hydrochloride (100 g, 0.62 mol) was added to toluene (1 L) and heated to 100° C. for 24 hours, after which point the reaction was allowed to cool to 20° C. The mixture was filtered, washed with toluene (2×250 mL) and pulled dry. The crude HCl salt was combined with a previous batch (performed using 180 g of 3-fluorophenylhydrazine hydrochloride and 234 g of 3-fluorophenylhydrazine hydrochloride) and partitioned between DCM (4 L) and sat. aq. NaHCO$_3$ (4 L). The mixture was stirred until no solid remained. The DCM layer was separated off, dried (MgSO$_4$), filtered and concentrated in vacuo to provide the title compound as an orange solid (210 g) in 52% yield. Purity>95% (on a molar basis) by NMR and 94.4% (on a molar basis) by LCMS.

Part (IV): Formation of 5-Aminopyrazole Carbamates

Synthesis 12

Phenyl N-[3-tert-butyl-1-(3-fluorophenyl)-1H-pyrazol-5-yl]carbamate

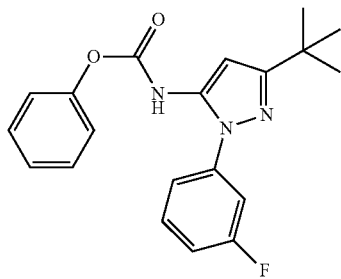 [SMILES: CC(C)(C)c1cc(NC(=O)Oc2ccccc2)n(-c2cccc(F)c2)n1]

Method F:

3-(tert-butyl)-1-(3-fluorophenyl)-1H-pyrazol-5-amine (210 g, 0.90 mol) was dissolved in THF (5 L) at 00° C. before the addition of pyridine (146 mL, 1.80 mol). Phenyl chloroformate (113 mL, 0.90 mol) in THF (300 mL) was charged dropwise at 0-5° C. over 30 minutes. The reaction mixture was stirred at 00° C. for 30 minutes, and then allowed to warm to room temperature. After 4 hours, HPLC showed 8% of stage 1 remained. A further charge of phenyl chloroformate (11 mL, 0.088 mol) was added and after 30 minutes, HPLC analysis indicated that the reaction was complete. EtOAc (5 L) was charged and the organic layer washed with 1 M HCl (2×1.2 L), water (1.2 L), sat. aq. NaHCO$_3$ (1.2 L) and sat. brine (1.2 L). The organic layer was dried (MgSO$_4$), filtered, and concentrated in vacuo. The crude oil was taken up in a 1:3 mixture of EtOAc/heptane and concentrated in vacuo to give a solid. The solid was slurried in heptane (2.5 L) for 1 hour, filtered, and washed with heptane (200 mL). The material was dried at 400° C. overnight to give the title compound (286 g) in 90% yield. Purity>95% by NMR.

Part (V): Coupling of Arylpyrazole and 4-aminophenoxypyridopyrazinone Fragments with Formation of Urea Linker Synthesis 13

1-[3-tert-butyl-1-[(3-fluoro-phenyl)-1H-pyrazol-5-yl]3-[2-fluoro-4(3-oxo-3,4-dihydro pyrido[2,3-b] pyrazin-8-yloxy)phenyl]urea (TBAP-001)

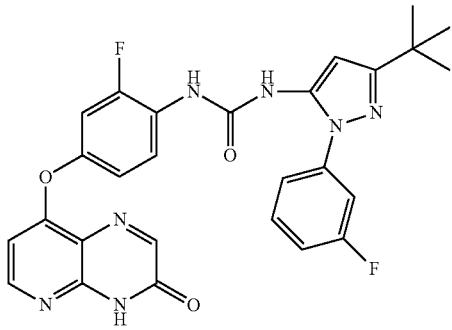 [SMILES: CC(C)(C)c1cc(NC(=O)Nc2ccc(Oc3ccnc4[nH]c(=O)cnc34)cc2F)n(-c2cccc(F)c2)n1]

Method G:

81 mg (0.31 mmol) 3-tert-butyl-1-(3-fluorophenyl)-pyrazole-5-carboxylic acid were dissolved in 2 mL DMF in a Carousel tube under stirring and inert atmosphere. Then 0.044 mL (0.32 mmol) triethyl amine and 0.067 mL (0.032 mmol) DPPA were added and the stirring continued for 30 minutes at 0'C and for an additional 1 hour at room temperature. To this reaction mixture, the 4-(3-fluoro-4-aminophenyl)-pyridine-[2,3-b]-pyrazin-2-one (40 mg, 0.15 mmol) (see, e.g., Zambon et al., 2010) was added at once and the tube with the reaction mixture heated at 100° C. for 30 minutes, under stirring and an argon atmosphere. After cooling at room temperature, the solution was diluted with 10 mL AcOEt. The organic layer was washed with 2×10 mL brine, dried (MgSO$_4$), and evaporated to dryness. The residue thus obtained was triturated with Et$_2$O and filtered to give the title compound as a pale brown amorphous solid.

Yield: 66 mg (83.0%). $^1$H NMR (500 MHz, DMSO-d$_6$) δ: 1.29 (s, 9H, t-Bu), 6.41 (s, 1H, H$_{Pyrazol}$), 6.64 (d, 1H, H$_{Pyr}$, J=5.6 Hz), 7.02-7.07 (m, 1H, H$_{Arom\ central}$), 7.22-7.30 (m, 2H, H$_{Arom\ pyrazol}$), 7.40-7.44 (m, 2H, H$_{Arom\ central}$+H$_{Arom\ pyrazol}$), 7.53-7.60 (m, 1H, H$_{Arom\ pyrazol}$), 8.14 (t, 1H, H$_{Arom\ central}$, J=9.1 Hz), 8.17 (S, 1H, H$_{pyazinone}$), 8.36 (d, 1H, H$_{Pyr}$, J=5.6 Hz), 8.87 (s, 1H, NH$_{urea}$), 8.98 (s, 1H, NH$_{urea}$), 12.90 (s, 1H, NH). LC-MS, t$_R$=2.61 min, m/z: 531.2 (M)$^+$, calcd for C$_{27}$H$_{23}$F$_2$N$_7$O$_3$. HRMS: (M)$^+$ calcd for C$_{27}$H$_{23}$F$_2$N$_7$O$_3$, 531.1830, found: 531.1832.

Method H:

To 4-(3-fluoro-4-aminophenyl)-pyridine-[2,3-b]-pyrazin-2-one (169.5 g, 0.623 mol) was charged phenyl N-[3-tert-butyl-1-(3-fluorophenyl)-1H-pyrazol-5-yl]carbamate (220 g, 0.623 mol) and DMSO (1.7 L). The reaction mixture was stirred at 20-22° C. overnight. $^1$H NMR indicated that the reaction was complete. The reaction was quenched into water (8.6 L) and stirred for 1 hour before being filtered and washed with water (2×2 L). The material was dried at 60° C. over the weekend. The solid was slurried in EtOAc (3.39 L) for 1 hour, filtered, and washed with EtOAc (750 mL) to give 320 g of the title compound. NMR indicated that phenol was still present. The material was re-slurried in EtOAc (3.2 L) for 1 hour, filtered, and washed with EtOAc (500 mL) and dried to afford 293 g of the title compound (9% EtOAc by weight) by NMR, one single impurity 0.8% by weight). The solid was recrystallised from THF (5.7 L) and heptane (2.85 L), allowing the batch to cool to room temperature before filtering off the solids. The filter cake was washed with heptane (2.85 L) and dried at 45° C. overnight to give 221 g of the title compound. HPLC analysis showed that the previous impurity at 0.8% (by weight) was reduced to 0.23% (by weight); however, the urea impurity was enriched to 0.58% (by weight). $^1$H NMR showed 5% heptane (by weight). The material was dried at 110° C. for 12 hours to bring the heptane level to <0.5% (by weight) by NMR, giving a total of 211 g of the title compound as a white crystalline solid at a 64% yield. HPLC purity 98.8% (by weight), one single impurity 0.58% (by weight).

Synthesis 14

1-[3-tert-butyl-1-[(3-methyl-phenyl)-1H-pyrazol-5-yl]3-[2-fluoro-4(3-oxo-3,4-dihydro pyrido[2,3-b]pyrazin-8-yloxy)phenyl]urea (TBAP-002)

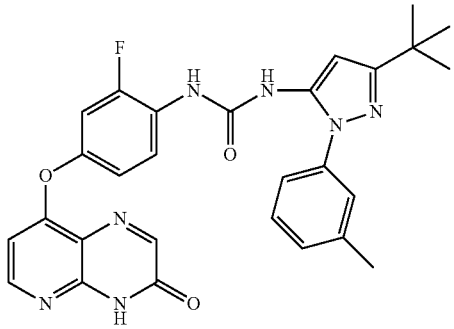 [SMILES: Cc1cccc(-n2nc(C(C)(C)C)cc2NC(=O)Nc2ccc(Oc3ccnc4[nH]c(=O)cnc34)cc2F)c1]

Using Method G, with 3-tert-butyl-1-(3-methylphenyl)-1H-pyrazole-5-carboxylic acid (80 mg, 0.31 mmol) and 4-(3-fluoro-4-aminophenyl)-pyridine-[2,3-b]-pyrazin-2-one (40 mg, 0.15 mmol), the title compound was obtained as an off-white solid.

Yield: 69 mg (87.4%). $^1$H NMR (500 MHz, DMSO-$d_6$) δ: 1.28 (s, 9H, t-Bu), 2.40 (s, 3H, 3-CH$_3$), 6.39 (s, 1H, H$_{Pyrazol}$), 6.64 (d, 1H, H$_{Pyr}$, J=5.6 Hz), 7.02-7.06 (m, 1H, H$_{Arom\ central}$), 7.22-7.36 (m, 4H, 3H$_{Arom\ pyrazol}$+1H$_{Arom\ central}$), 7.43 (t, 1H, H$_{Arom\ pyrazol}$, J=7.7 Hz), 8.16 (t, 1H, H$_{Arom\ central}$, J=9.1 Hz), 8.17 (s, 1H, H$_{pyrazinone}$), 8.36 (d, 1H, H$_{pyr}$, J=5.6 Hz), 8.81 (s, 1H, NH$_{urea}$), 8.98 (s, 1H, NH$_{urea}$), 12.90 (s, 1H, NH). LC-MS, $t_R$=2.65 min, m/z: 527.2 (M)$^+$, calcd for C$_{28}$H$_{26}$FN$_7$O$_3$. HRMS: (M+H)$^+$ calcd for C$_{28}$H$_{26}$FN$_7$O$_3$, 527.2081, found: 527.2088.

Synthesis 15

1-[3-tert-butyl-1-[(3-trifluoromethyl-phenyl)-1H-pyrazol-5-yl]3-[2-fluoro-4(3-oxo-3,4-dihydro pyrido[2,3-b]pyrazin-8-yloxy)phenyl]urea (TBAP-003)

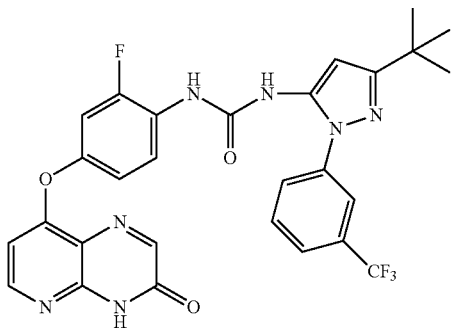 [SMILES: CC(C)(C)c1cc(NC(=O)Nc2ccc(Oc3ccnc4[nH]c(=O)cnc34)cc2F)n(-c2cccc(C(F)(F)F)c2)n1]

Using Method G, with 3-tert-butyl-1-(3-trifluoromethyl-phenyl)-1H-pyrazole-5-carboxylic acid (97 mg, 0.31 mmol) and 4-(3-fluoro-4-aminophenyl)-pyridine-[2,3-b]-pyrazin-2-one (40 mg, 0.15 mmol), the title compound was obtained as an off-white solid.

Yield: 70 mg (80.4%). $^1$H NMR (500 MHz, DMSO-$d_6$) δ: 1.30 (s, 9H, t-Bu), 6.42 (s, 1H, H$_{Pyrazol}$), 6.64 (d, 1H, H$_{Pyr}$, J=5.6 Hz), 7.02-7.06 (m, 1H, H$_{Arom\ central}$), 7.27-7.36 (m, 1H, H$_{Arom\ central}$), 7.74-7.80 (m, 2H, H$_{Arom\ pyrazol}$), 7.86-7.90 (m, 2H, H$_{Arom\ pyrazol}$), 8.05 (t, 1H, H$_{Arom\ central}$, J=9.1 Hz), 8.17 (s, 1H, H$_{pyrazinone}$), 8.36 (d, 1H, H$_{pyr}$, J=5.6 Hz), 8.87 (s, 1H, NH$_{urea}$), 8.93 (s, 1H, NH$_{urea}$), 12.90 (s, 1H, NH). LC-MS, $t_R$=2.71 min, m/z: 581.2 (M)$^+$, calcd for C$_{28}$H$_{23}$F$_4$N$_7$O$_3$. HRMS: (M+H)$^+$ calcd for C$_{28}$H$_{23}$F$_4$N$_7$O$_3$, 581.1798, found: 581.1796.

Synthesis 16

1-(3-tert-butyl-1-(3-methoxyphenyl)-1H-pyrazol-5-yl)-3-(2-fluoro-4-(3-oxo-3,4-dihydropyrido[3,2-b]pyrazin-8-yloxy)phenyl)urea (TBAP-004)

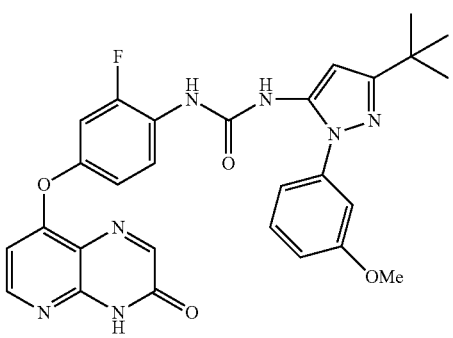 [SMILES: COc1cccc(-n2nc(C(C)(C)C)cc2NC(=O)Nc2ccc(Oc3ccnc4[nH]c(=O)cnc34)cc2F)c1]

Using Method G with 3-tert-butyl-1-(3-methoxyphenyl)-1H-pyrazole-5-carboxylic acid (60 mg, 0.22 mmol) and 8-(4-amino-3-fluorophenoxy)-pyrido[2,3-b]pyrazin-3(4H)-one (31.6 mg, 0.12 mmol), the title compound was obtained as a light yellow solid.

Yield: 50 mg (84%). $^1$H-NMR (DMSO-$d_6$), δ (ppm), J (Hz): 1.29 (s, 9H, tert-Bu), 3.83 (s, 3H, OCH$_3$), 6.41 (s, 1H, PyzH), 6.66 (d, $^3J_{HH}$=5.7, 1H, PyrH), 7.01-7.12 (m, 4H, ArH), 7.31 (m, 1H, ArH), 7.46 (t, $^3J_{HH}$=8.1, 1H, ArH), 8.18 (m, 2H, ArH), 8.38 (d, $^3J_{HH}$=5.7, 1H, PyrH), 8.85 (br s, 1H, NH), 9.03 (br s, 1H, NH), 12.92 (br s, 1H, N/H); $^{19}$F-NMR (DMSO-$d_6$), δ (ppm): −124.8. LC-MS (2.59 min): m/z calcd. for C$_{28}$H$_{27}$FN$_7$O$_4$ [M+H]$^+$: 544.1; found: 544.1. HRMS (3.19 min): m/z calcd. for C$_{28}$H$_{27}$FN$_7$O$_4$ [M+H]$^+$: 544.21031; found: 544.21029.

Synthesis 17

1-(3-tert-butyl-1-(2-oxo-1,2-dihydropyridin-4-yl)-1H-pyrazol-5-yl)-3-(2-fluoro-4-(3-oxo-3,4-dihydro-pyrido[3,2-b]pyrazin-8-yloxy)phenyl)urea (TBAP-005)

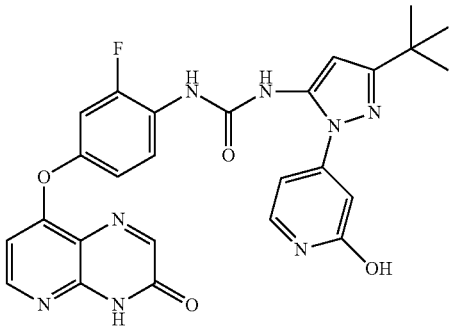 [SMILES: CC(C)(C)c1cc(NC(=O)Nc2ccc(Oc3ccnc4[nH]c(=O)cnc34)cc2F)n(-c2ccnc(O)c2)n1]

Using Method G with 3-tert-butyl-1-(2-oxo-1,2-dihydropyridin-4-yl)-1H-pyrazole-5-carboxylic acid hydrochloride (70.8 mg, 0.238 mmol) and 8-(4-amino-3-fluorophenoxy)-pyrido[2,3-b]pyrazin-3(4-6H)-one (32.4 mg, 0.119 mmol), a solid was obtained which was purified by column chromatography on silica gel, eluting with 5→30% (by volume) MeOH in DCM, to give the title compound as a white solid.

Yield: 15 mg (24%). $^1$H-NMR (DMSO-d$_6$), δ (ppm), J (Hz): 1.28 (s, 9H, tert-Bu), 6.43 (s, 1H, PyzH), 6.50 (d, $^3J_{HH}$=2.2, 1H, ArH), 6.58 (dd, $^3J_{HH}$=7.2, 2.2, 1H, ArH), 6.66 (d, $^3J_{HH}$=5.6, 1H, PyrH), 7.06 (m, 1H, ArH), 7.32 (m, 1H, ArH), 7.50 (d, $^3J_{HH}$=7.2, 1H, ArH), 8.13 (m, 1H, ArH), 8.18 (m, 1H, ArH), 8.37 (d, $^3J_{HH}$=5.6, 1H, PyrH), 9.05 (br s, 1H, NH), 9.13 (s, 1H, N/H), 11.66 (br s, 1H, N/H), 12.90 (br s, 1H, NH). LC-MS (2.36 min): m/z calcd. for C$_{26}$H$_{24}$FN$_8$O$_4$ [M+H]$^+$: 531.1; found: 531.2. HRMS (2.97 min): m/z calcd. for C$_{26}$H$_{24}$FN$_8$O$_4$ [M+H]$^+$: 531.18991; found: 531.18952.

Biological Methods and Data

DELFIA Kinase Assay

Compounds were assessed in a kinase assay performed according to the following protocol.

$^{V600E}$BRAF Preparation:

$^{V600E}$BRAF was generated by infection of SF9 insect cells cultured in SF-900 II medium (Invitrogen, Paisley, Scotland) with a baculovirus containing full-length human BRAF with an N-terminal histidine tag and purified by nickel-agarose affinity chromatography.

GST-MEK Preparation:

Full-length rabbit MEK1 protein was expressed with a GST tag at the N-terminus and a C-terminal histidine tag in *Escherichia coli* JM109 bacteria and purified by nickel-agarose affinity chromatography.

Purification of $^{V600E}$BRAF and GST-MEK:

Procedure:

1. Lyse cells in re-suspension buffer (1 mL per 10 mL of SF9 culture or JM109 culture for BRAF or MEK respectively), sonicate for 1-2 minutes and spin down at 14,000 rpm (in 2 mL tubes) for 10 minutes.
2. Take 1.5 mL of nickel-agarose 'beads' per 10 mL of lysate and add to column (Bio-rad).
3. Wash column with re-suspension buffer 3 times.
4. Add lysate to the column.
5. Wash 3 times with 10 mL washing buffer.
6. Add 10 mL of elution buffer to the beads and collect in 2 mL tubes.
7. Check protein concentration of the elutions and dialyse overnight at 4° C. in dialysis buffer.

Buffers:

TABLE 3

| Solution | Re-suspension Buffer (100 mL) | Washing Buffer (100 mL) | Elution Buffer (30 mL) |
|---|---|---|---|
| 1M Tris pH 8.0 | 50 mM-5 mL | 50 mM-5 mL | 50 mM-1.5 mL |
| 5M NaCl | 100 mM-2 mL | 100 mM-2 mL | 100 mM-600 μL |
| 1M MgCl$_2$ | 0.5 mM-50 μL | — | — |
| Triton X100 | 10%-1 mL | 10%-1 mL | 10%-300 μL |
| 1M Benzamidine | 1 mM-100 μL | 1 mM-100 μL | 1 mM-30 μL |
| Aprotinin (5 mg/mL) | 5 μg/mL-100 μL | 5 μg/ml-100 μL | 5 μg/ml-30 μL |
| Leupeptin (5 mg/mL) | 10 μg/mL-200 μL | 10 μg/ml-200 μL | 10 μg/ml-60 μL |
| 1M PMSF | 1 mM-100 μL | 1 mM-100 μL | 1 mM-30 μL |
| Imadazole | — | — | 150 mM-2.25 mL |
| β-Mercaptoethanol | — | — | 1%-300 μL |

Dialysis Buffer (Mixed and Stored in Cold Room):

TABLE 4

| Solution | Volume |
|---|---|
| 1M Tris pH 7.5 | 20 mL |
| 0.5M EDTA pH 8.0 | 2 mL |
| Triton X100 | 1 mL |
| Water | Up to 0.5 L |
| Glycerol | Up to 1 L |
| β-Mercaptoethanol | 3 mL (prior to use) |

DELFIA Kinase Buffer (DKB):

TABLE 5

| Reagent | Stock Concentration | Volume per mL (μL) | Volume per 10 mL plate (μL) |
|---|---|---|---|
| 20 mM MOPS pH 7.2 | 0.2M | 100 | 1000 |
| 0.5M EGTA pH 8.0 | 0.5M | 10 | 100 |
| 10 mM MgCl$_2$ | 1M | 10 | 100 |
| 0.1% β-mercaptoethanol | — | 1 | 10 |
| 25 mM β-glycerophosphate | 0.5M | 50 | 500 |
| Water | 100% | 829 | 8290 |

MOPS = 3-[N-Morpholino] propanesulfanic acid (Sigma M3183).
EGTA = Ethylene glycol-bis(2-aminoethylether)-N,N,N',N'-tetraacetic acid (Sigma E3889).

DKB1 (DKB with BRAF and MEK Protein):

Combine 4950 μL of DKB and 50 μL of 2.5 mg/mL GST-MEK stock obtained as described above (to give 1 mg of MEK per 40 μL). Then add 22.5 μL of BRAF stock obtained as described above to give ~0.2 μL of BRAF per 40 μL.

DKB2 (DKB with MEK Protein):

Combine 4950 μL of DKB and 50 μL of 2.5 mg/mL GST-MEK stock (to give 1 mg of MEK per 40 μL). Use 500 μL of this for the blow out (BO) and the empty vector (EV) control.

ATP:

100 mM ATP stock in distilled water, dilute to 500 μM to give 100 μM final concentration in assay.

Inhibitors (Test Compounds):

100 mM stock, dilute to 10, 3, 1, 0.3, 0.1, 0.03, 0.01, 0.003, 0.001, 0.0003, and 0.0001 mM in DMSO in drug plate, resulting in concentrations of 100, 30, 10, 3, 1, 0.3, 0.1, 0.03, 0.01, 0.003, and 0.001 μM in the assay.

Primary Antibody:

Phospho-MEK1/2 CST #9121S diluted 1:1000 in DELFIA assay buffer (AB). Pre-incubate antibody in the AB for 30 minutes at room temperature prior to use.

Secondary Antibody:

Anti-rabbit-Eur labelled secondary Perkin Elmer #AD0105 diluted 1:1000 in DELFIA assay buffer (AB). Pre-incubate antibody in the AB for 30 minutes at room temperature prior to use. (Primary and secondary antibodies were incubated together.)

Tween:

0.1% Tween 20 in water.

Assay Buffer:

DELFIA assay buffer Perkin Elmer #4002-0010.

Enhancement Solution:

DELFIA enhancement solution Perkin Elmer #4001-0010.

Assay Plates:

96 well glutathione-coated black plate Perbio #15340.

Procedure:

1. Pre-block wells with 5% milk in TBS for 1 hour.
2. Wash wells 3× with 200 μL TBS.

3. Plate out 40 μL of DKB1 for all inhibitors (test compounds), DMSO control, and optionally other control compounds.

4. Plate out 40 μL of DKB2 for BO and EV wells.

5. Add inhibitors (test compounds) at 0.5 μL per well according to desired plate layout.

6. Add 0.5 μL DMSO to vehicle control wells.

7. Add 2 μL of BRAF to BO and EV wells.

8. Pre-incubate with test compounds for 10 minutes at room temperature with shaking.

9. Add 10 μL of 500 μM ATP stock, in DKB, to give 100 μM assay concentration.

10. Seal plates with TopSeal and incubate at room temperature with shaking for 45 minutes.

11. Wash plates 3× with 200 μL 0.1% Tween20/water to terminate reaction.

12. Add 50 μL per well of antibody mix and incubate for 1 hour at room temperature with shaking.

13. Wash plates 3× with 200 μL 0.1% Tween20/water.

14. Add 100 μL DELFIA enhancement solution per well, cover in foil, and incubate at room temperature for 30 minutes with shaking.

15. Read on Victor plate reader (Perkin-Elmer, Turku, Finland) using Europium protocol.

Values for the blank (Empty Vector) are subtracted from all values. The DMSO controls are set as 100% activity and assay points (the response) are calculated as a percentage of the DMSO control. Data are plotted using Graphpad Prism software and a non-linear regression line is calculated using a variable slope sigmoidal dose-response equation:

$$Y = Bottom + [Top - Bottom] / [1 + 10^{((\log EC50 - X) * HillSlope)}]$$

where X is the logarithm of concentration and Y is the response. The $IC_{50}$ generated by this procedure is the concentration of the drug that produces a percentage control fluorescence value midway between the saturation, and zero-effect plateaus. Three independent assays are usually performed and the mean $IC_{50}$ is reported.

The data are summarised in the following table.

TABLE 6

BRAF V600E Kinase Assay Data

| Compound | $IC_{50}$ (μM) |
|---|---|
| TBAP-01 | 0.062 |
| TBAP-02 | 0.099 |
| TBAP-03 | 0.13 |
| TBAP-04 | 0.047 |
| TBAP-05 | 0.39 |

Cell Based Phospho-ERK Assay (Mutant BRAF WM266.4 Cells)

Compounds were assessed using a cell-based assay which was performed according to the following protocol.

Day 0:

Plate out 16,000 mutant BRAF WM266.4 cells/well in 99 μL medium in a 96-well plate.

Day 1:

1. Add 1 μL test compound to the cells (total 1 μL solution).

2. Incubate the cells with test compound for 6 hours at 37° C.

3. Aspirate off the solution from all of the wells.

4. Fixate the cells with 100 μL 4% formaldehyde/0.25% Triton X-100 PBS per well.

5. Incubate the plate for 1 hour at 4° C.

6. Aspirate off the fixing solution and add 300 μL TBS per well.

7. Leave the plate overnight at 4° C.

Day 2:

1. Wash the plate 2× with 200 μL PBS per well.

2. Block with 100 μL 5% dried milk in TBS.

3. Incubate the plate for 20 minutes at 37° C.

4. Wash the plate 2× with 0.1% tween/$H_2O$.

5. Add 50 μL of 3 μg/mL primary antibody pERK (Sigma M8159), diluted in 5% milk powder/TBS, to each well.

6. Incubate the plate for 2 hours at 37° C.

7. Wash the plate 3× with 0.1% tween/$H_2O$.

8. Add 50 μL of 0.45 μg/mL secondary Europium-labelled anti-mouse antibody (Perkin Elmer) to each well.

9. Incubate the plate for 1 hour at 37° C.

10. Wash the plate 3× with 0.1% tween/$H_2O$.

11. Add 100 μL enhancement solution (Perkin Elmer) to each well.

12. Leave the plate for approximately 10 minutes at room temperature before gently shaking the plate.

13. Read Europium Time Resolved Fluorescence in Victor2 plate reader (Perkin-Elmer, Turku, Finland).

14. Wash the plate 2× with 0.1% tween/$H_2O$.

15. Measure the protein concentration with Bicinchoninic Acid assay (BCA, Sigma) by adding 200 μL of solution per well.

16. Incubate the plate for 30 minutes at 37° C.

17. Read absorbance levels at 570 nm in a plate reader.

Note that Europium counts are normalised for protein levels by dividing counts by absorbance.

Values for the blank (no cells) are subtracted from all values. The DMSO controls are set as 100% activity and assay points (the response) are calculated as a percentage of the DMSO control. Data are plotted using Graphpad Prism software and a non-linear regression line is calculated using a variable slope sigmoidal dose-response equation:

$$Y = Bottom + [Top - Bottom] / [1 + 10^{((\log EC50 - X) * HillSlope)}]$$

where X is the logarithm of concentration and Y is the response). The $IC_{50}$ generated by this procedure is the concentration of the drug that produces a percentage control fluorescence value midway between the saturation, and zero-effect plateaus. Three independent assays are usually performed and the mean $IC_{50}$ is reported.

The data are summarised in the following table.

TABLE 7

Cell-Based Phosho-ERK Assay Data

| Compound | $IC_{50}$ (μM) |
|---|---|
| TBAP-01 | 0.018 |
| TBAP-02 | 0.012 |
| TBAP-03 | 0.019 |
| TBAP-04 | 0.008 |
| TBAP-05 | 0.45 |

SRB Cell Proliferation Assay (SRB $GI_{50}$)

Cell lines are routinely cultured in DMEM or RPMI1640 supplemented with 10% foetal bovine serum at 37° C. in a 10% $CO_2$ water-saturated atmosphere. Cultures are maintained in exponential growth phase by sub-culturing before having become confluent (3-5 day intervals). Single cell suspensions are prepared by harvesting an 80 cm² tissue culture flask with 5 mL commercial trypsin EDTA. After 5 minutes, the detached cells are mixed with 5 mL fully complemented culture medium and centrifugally pelleted (1000 rpm for 7 minutes). After aspirating the supernatant, the cell pellet is re-suspended in 10 mL fresh medium and the cells fully disaggregated by drawing the whole volume up/down 5 times through a 19-gauge needle. The concentration of the cells is determined using a haemocytometer (1/10 dilution). A suitable volume to give at least a 2-fold excess for the number of tests being conducted, typically 100-200 mL, is prepared by diluting the cell suspension to 10,000-40,000/mL, and 100 μL/well dispensed into 96 well plates using a programmable 8-channel peristaltic pump, giving 1000-4000 cells/well, leaving column 12 blank. The plates are returned to the incubator for 24 hours to allow the cells to re-attach.

The compounds being tested are prepared at 10 mM in DMSO. Aliquots (24 μL) are diluted into 1.2 mL culture medium giving 200 μM, and 10 serial dilutions of 3× performed by transferring 80 μL to 160 μL. Aliquots (100 μL) of each dilution are added to the wells, using an 8-channel pipettor, thus performing a final further 2× dilution, and giving doses ranging from 100 μM to 0.005 μM. Column 11 receives plain culture medium only. Each compound is tested in quadruplicate, each replicate being the average of four wells.

After a further 5 days growth, the plates are emptied, and the cells are fixed in 10% trichloroacetic acid for 30 minutes at 4° C. After thorough rinsing in running tap water, the plates are dried, and stained by adding 50 μL of a solution of 0.1% sulphorhodamine-B in 1% acetic acid, for 10 minutes at room temperature. The stain is poured out and the plates thoroughly rinsed under a stream of 1% acetic acid (thus removing unbound stain) and dried. The bound stain is taken into solution by addition of 100 μL Tris buffer pH 8, followed by 10 minutes on a plate-shaker (approximately 500 rpm). The absorbance at 540 nm in each well (being proportional to the number of cells present) is determined using a plate reader.

After averaging the blank values in column 12, this was subtracted from all values, and results expressed as a percentage of the untreated value (column 11). The 10 values so derived (in quadruplicate) are plotted against the logarithm of the drug concentration, and analysed by non-linear regression to a four parameter logistic equation, setting constraints if suggested by inspection. The $GI_{50}$ generated by this procedure is the concentration of the drug that produces a percentage control $A_{540}$ midway between the saturation, and zero-effect plateaus.

The results for a range of cell lines are summarized below.

TABLE 8

SRB Cell Proliferation Assay Data for TBAP-01 in a Panel of Mutant BRAF (mutBRAF) Cell Lines

| Cell line | $GI_{50}$ (μM) |
|---|---|
| A375 (melanoma) | 0.178 |
| WM266.4 (melanoma) | 0.062 |
| UACC62 (melanoma) | 0.072 |
| LOX INVI (melanoma) | 0.093 |
| HT29 (colorectal carcinoma) | 0.59 |
| COLO205 (colorectal carcinoma) | 0.043 |
| RKO (colorectal carcinoma) | 0.69 |
| Mawi (colorectal carcinoma) | 0.49 |
| WiDr (colorectal carcinoma) | 0.39 |
| Colo741 (colorectal carcinoma) | 0.48 |

TABLE 9

SRB Cell Proliferation Assay Data for TBAP-01 in a Panel of Mutant RAS Cell Lines

| Cell line | $GI_{50}$ (μM) |
|---|---|
| SW620 (human colorectal carcinoma) | 0.48 |
| HCT116 (human colorectal carcinoma) | 0.60 |
| SKMEL2 (human melanoma) | 0.39 |
| DO4 (human melanoma) | 0.71 |
| WM1361 (human melanoma) | 0.39 |
| PDAC R172H (p53 mut) (mouse pancreatic carcinoma) | 1.15 |
| MiaPaCa (human pancreatic carcinoma) | 0.29 |
| Panc-1 (human pancreatic carcinoma) | 2.78 |
| RPMI8226 (human myeloma) | 0.49 |
| A549 (human lung carcinoma) | 1.81 |
| H23 (human lung carcinoma) | 1.26 |

TABLE 10

SRB Cell Proliferation Assay Data for TBAP-01 in a Panel of Wild Type BRAF and RAS (wtBRAF/RAS) Cell Lines

| Cell line | $GI_{50}$ (μM) |
|---|---|
| D35 (human melanoma) | 1.45 |
| KM12 (human colorectal carcinoma) | 1.74 |
| D24 (human melanoma) | 2.73 |

TABLE 11

SRB Cell Proliferation Assay Data for TBAP-01 in Additional Cell Lines

| Cell line | $GI_{50}$ (μM) |
|---|---|
| A375 | 0.178 |
| A375/R (made PLX4720 resistant in vitro) | 0.839 |
| A375/R/X (made PLX4720-resistant in vivo) | 0.252 |
| A375/DR (made PLX4720- and dabrafenib-resistant in vivo) | 0.95 |
| Colo829 | 0.189 |
| Colo829/R (made PLX4720 resistant in vitro) | 0.029 |
| DO4 (NRAS mutant) | 0.275 |
| SBCL2 (NRAS mutant) | 0.719 |
| RM-11 Naive cell line derived from untreated patient with in vitro induced resistance to PLX4720 | 1.34 |
| LP2 CL2 (LINE 1) human patient-derived melanoma cells (mutant BRAF, acquired resistance to vemurafenib) | 0.043 |
| LP2 CL3 human patient-derived melanoma cells (mutant BRAF, acquired resistance to vemurafenib) | 0.269 |
| RM-7 human patient-derived melanoma cells (mutant BRAF, acquired resistance to vemurafenib) | 2.6 |
| RM-2 (LINE 2) human patient-derived melanoma cells (mutant BRAF, intrinsic resistance to vemurafenib) | 0.569 |
| RM-17 (LINE 3) human patient-derived melanoma cells (mutant BRAF, resistant to Dabrafenib & Trametinib combination) | 2.600 |
| RM33S human patient-derived melanoma cells (wt BRAF, wt RAS, ipilimumab resistant) | 1.13 |

Xenograft Studies

For standard cell lines, cells were inoculated subcutaneously in suspension (0.2 mL) into flank of female athymic or severe combined immunodeficiency mice. Groups of 7-8 mice were assigned to treatment following stratified allocation of tumour volumes. Treatment with TBAP-01 began between days 11-14 post-cell administration. For gavage, 200 μL of a suspension (DMSO:water, 1:19, v/v at 10 mL/kg) was administered. Control animals received a similar dosage of vehicle (DMSO:water, 1:19, v/v). Treatment with TBAP-01 was continued once daily for 24 doses.

For patient derived xenografts (PDXs), fresh tissue was collected immediately following surgery into RPMI supplemented with 10% FBS. The tissue was transferred into a sterile petri dish. Necrotic parts of the tumour were removed and a 5×5×5 mm piece was implanted subcutaneously into the flank of a Cb 17 NOD SCID mouse. When the tumour reached Home Office license size limits, it was excised, and viable tissue dissected into 5×5×5 mm cubes and transplanted into additional Cb 17 NOD SCID mice using the same procedure. Genomic and histological analyses confirmed that the tumours at each point were derived from the starting material. Following transplantation, tumour RM-2 (LINE 2) (BRAF mutant, intrinsic vemurafenib resistant patient derived xenograft), tumour RM-17 (LINE 3) (BRAF mutant patient derived xenograft resistant to dabrafenib+trametinib combination), and RM33S (BRAF wild type Ras wild type from a patient that is ipilimumab-refractory) were allowed to grow to approximately 50-60 mm$^3$ before initiation of treatment by daily orogastric gavage of TBAP-01 at 20 mg/kg/day or vehicle for 24 or 17 days respectively. Patient derived cell LP2-CL2 (LINE 1) (BRAF mutant, derived from a patient who acquired resistance to vemurafenib in the clinic after 3 months of treatment) was established from fresh tissue collected after surgery. Cells were grown in RPMI substituted with 10% FBS.

The results are summarised in the following table.

TABLE 12

Xenograft Studies
Therapeutic Efficacy:
Ratio of Tumour Volume (treated)/Tumour Volume (Control)

| Xenograft | TBAP-01 | TBAP-02 |
|---|---|---|
| A375 human melanoma cells (mutant BRAF) | 0.07 | 0.31 |
| WM266.4 human melanoma cells (mutant BRAF) | 0.08 | — |
| A375/R human melanoma cells (mutant BRAF, vemurafenib resistant) | 0.33 | — |
| SW620 human colorectal carcinoma cells (mutant RAS) | 0.4 | — |
| PDAC R172H (p53 mut) (mouse pancreatic carcinoma) | 0.45 | — |
| LP2 CL2 (LINE 1) human patient-derived melanoma cells (mutant BRAF, acquired resistance to vemurafenib) | 0.09 | — |
| RM-2 (LINE 2) human patient-derived melanoma cells (mutant BRAF, intrinsic resistance to vemurafenib) | 0.13 | — |
| RM-17 (LINE 3) human patient-derived melanoma cells (mutant BRAF, resistant to Dabrafenib & Trametinib combination) | 0.18 | — |
| RM33S human patient-derived melanoma cells (wt BRAF, wt RAS, ipilimumab resistant) | 0.45 | |

Biomarker Studies

Cells were inoculated sub-cutaneously in suspension (0.2 mL) into the flank of female athymic mice. Groups of 3-6 mice were assigned to treatment with a single dose of test compound (for the immunoblotting studies reported in Table 13) or 4 daily doses (for the immunohistochemistry studies reported in Table 13) 14-21 days post-cell administration. For gavage, 200 µL of 40-50 mg/kg TBAP-01 suspension in DMSO:water was administered. Control animals received a similar dosage of vehicle (DMSO:water, 1:19, v/v). Tumours were harvested 2-8 hours post-dosing and lysed in 1% NP40 lysis buffer (100 µL of buffer/15 mg of tissue) using a tissue homogeniser (Precellys 24). Total protein content was measured using the 660 nm Protein Assay (Pierce) and 40 µg of total protein were loaded into an SDS-page for further immunoblotting. ERK2 (Santa Cruz Technologies), phospho-MEK (Cell Signaling), and phospho-ERK (Sigma) antibodies were used for immunoblotting; signal was revealed using fluorescent secondary antibodies (Invitrogen and Li-cor) on the Odissey system (Li-cor). Alternatively, tumours were harvested 1 hour after final dosing at the end of therapy (24 daily doses) and processed in a similar way as described above.

Immunohistochemistry (IHC): Tumors were formalin-fixed and prepared as described elsewhere (see e.g., Dhomen et al., 2009) for staining with hematoxylin and eosin, rabbit pSRC (Invitrogen 44660G) and pERK (Cell Signaling 20G11). Positive and negative controls were included in each experiment. The scoring of the pattern and intensity of staining was performed in a blinded manner.

The data are summarised in the following table, which shows percentage reduction of phospho-MEK (ppMEK) and phospho-ERK (ppERK), as compared to vehicle-treated controls, for TBAP-01. pMEK and pERK are normalised to total ERK in treated samples as well as in control samples.

TABLE 13

Biomarker Studies
Percentage Reduction of Phospho-MEK (ppMEK)
Phospho-ERK (ppERK) and Phospho-SRC (pSRC)

| Biomarker | WM266.4 human melanoma cells (mutant BRAF) (1 dose) | SW620 human colorectal carcinoma cells (mutant RAS) (1 dose) | PDAC R172H mouse pancreatic carcinoma cells (mutant RAS) (4 daily doses) | PDAC R172H mouse pancreatic carcinoma cells (mutant RAS) (24 daily doses) |
|---|---|---|---|---|
| ppMEK 2 h | 60% | | | |
| ppMEK 4 h | | 42% | | |
| ppMEK 8 h | 68% | | | |
| ppERK 1 h | | | | 85% |
| ppERK 2 h | 67% | | | |
| ppERK 8 h | 40% | | | |
| pSRC 4 h | | | 80% | |

Pharmacokinetic Studies

Female BALB/cAnNCrl mice at least 6 weeks of age were used for the PK analyses. The mice were dosed intravenously (2 mg/kg, in DMSO:Tween 20:water 10:1:89 v/v) or orally by gavage. Samples were taken at 7 or 8 time-points between 5 minutes and 18 or 24 hours for the intravenous route and at 6 or 8 time-points between 15 minutes and 18 or 24 hours for the oral route. Three mice were used per time-point per route. They were placed under halothane or isoflurane anaesthesia and blood for plasma preparation was taken by terminal cardiac puncture into heparinized syringes. Plasma samples were snap frozen in liquid nitrogen and then stored at −70° C. prior to analysis. All procedures involving animals were performed in accordance with national Home Office regulations under the Animals (Scientific Procedures) Act 1986 and within guidelines set out by the Institute's Animal Ethics Committee and the United Kingdom Coordinating Committee for Cancer Research's ad hoc Committee on the Welfare of Animals in Experimental Neoplasia.

The data are summarised in the following table.

TABLE 14

Pharmacokinetic Data

| Compound | $C_{max}$ (nM) (10 mg/kg po) | AUC (h * nmol/L) (10 mg/kg po) | Time for which drug concentration is above SRB $GI_{50}$ (hours) |
|---|---|---|---|
| TBAP-01 | 68,831 | 509,747 | >18 |
| TBAP-02 | 13,041 | 41,754 | >18 |
| TBAP-03 | 25,533 | 48,158 | >18 |
| TBAP-04 | 47,870 | 125,950 | >6 | hERG Inhibition

Studies were conducted at Cyprotex Discovery in Cheshire, UK according to the contractor's protocol. The studies were performed on an IonWorks™ HT instrument (Molecular Devices Corporation), which automatically performs electrophysiology measurements in 48 single cells simultaneously in a specialised 384-well plate (PatchPlate™). The cells used were Chinese hamster ovary (CHO) cells stably transfected with hERG (cell-line obtained from Cytomyx, UK). A single-cell suspension was prepared in extracellular solution (Dulbecco's phosphate buffered saline with calcium and magnesium pH 7-7.2) and aliquots added automatically to each well of a PatchPlate™. The cells were then positioned over a small hole at the bottom of each well by applying a vacuum beneath the plate to form an electrical seal. The vacuum was applied through a single compartment common to all wells which was filled with intracellular solution (buffered to pH 7.2 with HEPES). The resistance of each seal was measured via a common ground-electrode in the intracellular compartment and individual electrodes placed into each of the upper wells.

Electrical access to the cell was then achieved by circulating a perforating agent, amphotericin, underneath the PatchPlate™ and then measuring the pre-compound hERG current. An electrode was positioned in the extracellular compartment and a holding potential of −80 mV applied for 15 seconds. The hERG channels were then activated by applying a depolarising step to +40 mV for 5 seconds and then clamped at −50 mV for 4 seconds to elicit the hERG tail current, before returning to −80 mV for 0.3 seconds. Test compound was then added automatically to the upper wells of the PatchPlate™ from a 96-well microtitre plate containing a range of concentrations of compound TBAP-01. Quinidine, an established hERG inhibitor, was included as an experimental control. TBAP-01 was dissolved in DMSO and assayed at final concentrations ranging from 100 μM to 32 nM in 0.25% DMSO. Buffer containing 0.25% DMSO was included as a negative control. The test compound was left in contact with the cells for 300 seconds before recording currents using the same voltage-step protocol as in the pre-compound scan. Each concentration was tested in 4 replicate wells.

Post-compound currents were expressed as a percentage of pre-compound currents and plotted against concentration for each compound. Where concentration-dependent inhibition was observed, the data were fitted to the following equation:

$$y=(y_{max}-y_{min})/(1+(x/x_{50})^s)+y_{min}.$$

wherein:

y=(post-compound current/pre-compound current)×100;

x=concentration;

$x_{50}$=concentration required to inhibit current by 50% ($IC_{50}$); and s=slope of the graph.

The data are summarised in the following table.

TABLE 15 hERG Inhibition Data

| Compound | $IC_{50}$ (μM) |
|---|---|
| TBAP-01 | >100 |
| TBAP-02 | 65 |
| TBAP-03 | >100 |
| TBAP-04 | >100 |
| TBAP-05 | — |

Activity Against Other Targets

Studies were conducted at Life Technologies in Paisley according to the contractor's protocol. TBAP-01 was dissolved in DMSO and assayed at final concentrations ranging from 10 µM to 0.5 nM in 1% DMSO, in the presence of an ATP concentration of 100 µM. $IC_{50}$ values for test compounds were determined using the Z'-LYTE® biochemical assay employing a fluorescence-based, coupled-enzyme format based on the differential sensitivity of phosphorylated and non-phosphorylated peptides to proteolytic cleavage.

Additional studies were conducted at The International Centre for Kinase Profiling in Dundee according to the contractor's protocol. TBAP-01 was dissolved in DMSO and assayed at a final concentration of 1 µM in 2% DMSO against 131 kinases. The assays were carried out using a radioactive ($^{33}$P-ATP) filter-binding assay.

The data are summarised in the following tables.

TABLE 16

TBAP-01 Activity Against Targets Involved in Resistance to BRAF Inhibitors

| | |
|---|---|
| $IC_{50}$ CRAF | 0.033 µM |
| $IC_{50}$ KDR | 0.12 µM |
| $IC_{50}$ PDGFRα | 0.8 µM |
| $IC_{50}$ PDGFRβ | 0.74 µM |
| $IC_{50}$ MET | 1.4 µM |
| $IC_{50}$ EGFR | 1.9 µM |
| IGF1Rβ | 78% @ 1 µM |

TABLE 17

TBAP-01 Activity Against Other Kinase Targets

| | |
|---|---|
| $IC_{50}$ Src | 0.027 µM |
| $IC_{50}$ Lck | 0.019 µM |
| $IC_{50}$ p38γ | 0.22 µM |
| $IC_{50}$ p38α | 0.47 µM |
| $IC_{50}$ FGFR1 | 0.47 µM |
| MINK1 | 4% activity remaining at 1 µM |
| TESK1 | 5% activity remaining at 1 µM |
| TAK1 | 6% activity remaining at 1 µM |
| YES1 | 6% activity remaining at 1 µM |
| ABL | 4% activity remaining at 1 µM |
| Tie-2 | 3% activity remaining at 1 µM |
| TrkA | 6% activity remaining at 1 µM |
| DDR2 | 3% activity remaining at 1 µM |
| VEGFR | 6% activity remaining at 1 µM |

Note, e.g., that it is well-known that: TAK1 is a target in cancers such as lymphoma and colorectal and pancreatic cancer; TrkA is a target in lung and breast cancer; DDR2 is a target in cancers such as squamous cell lung cancer; VEGFR and Tie-2 are anti-angiogenic targets; ABL is a target in leukemia; and YES1 is a target in cancers such as melanoma and breast cancer.

Antiviral Activity

The antiviral activity of compounds against the Encephalomyocarditis virus (ECMV) ATCC® VR-129B infection of HepG2 cell; herpes simplex virus HSV-1, SC16 infection of Vero cells; and Influenza A virus, A/Panama/2007/99 (H3N2) in MDCK cells; was assessed at KWSBiotest (Bristol, UK), according to the contractor's protocol.

Cells that are permissive of viral replication were grown up to sufficient numbers in growth media with supplements. Once cells were confluent they were seeded into 96 well flat-bottomed plates. For $EC_{50}$ (Effective Concentration, 50%) determination, the media was removed and compounds added at 10× final concentration in 0.4% DMSO 10 minutes prior to viral infection. One hour following infection, overlay media was added to the wells to give 1× concentration of compounds for the duration of the study. Vehicle and positive control wells were set up to control for any influence on cell viability. For $CC_{50}$ (Cytotoxic Concentration, 50%) determination, the same process was followed, except that medium only was added instead of virus inoculum.

Individual wells were then assessed using the MTT assay, which is a quantitative colorimetric assay for mammalian cell survival. Cells were incubated for 3 hours with 1 mg/mL MTT solution. Colour intensity was then determined by quantifying absorbance at the appropriate wavelength. The result provides an indication of the anti-viral efficacy of each compound as an $EC_{50}$, as well as a $CC_{50}$ to show any cytotoxic effect of the compounds on cells in the absence of viral infection. Virally infected wells were also inspected visually for any CPE or syncytia formation.

Effective Concentration ($EC_{50}$): The ability of compounds to reduce virus induced cell death was assessed using the MTT colorimetric assay for mammalian cell survival. The result from the assay was quantified using an ELISA plate reader, and the $EC_{50}$ for each of the compounds being assessed with each virus was determined. Results were displayed graphically along with the standard error of the mean (SEM) for each group. The statistical significance of the efficacy of each compound was calculated.

Cytotoxicity Concentration ($CC_{50}$): The cytotoxic effect of compounds was assessed using the MTT colorimetric assay for mammalian cell survival. The result from the assay was quantified using an ELISA plate reader, and the $CC_{50}$ for each of the compounds being assessed was determined. Results were displayed graphically along with the standard error of the mean (SEM) for each group. The statistical significance of the efficacy of each compound was calculated.

LPS-Stimulated TNF-α Release from Human Peripheral Blood Mononuclear Cells (PBMCs)

Tumor Necrosis Factor-α (TNF-α), a 17 kDa secreted cytokine, plays an important role in inflammatory diseases and immune disorders. TNF-α is mainly secreted by activated macrophages (see, e.g., Shakhov et al., 1990) and monocytes (see, e.g., Yao et al., 1997) in response to several inflammatory and immunological stimuli. For example, during bacterial infection, lipopolysaccharide (LPS), a component of gram-negative bacterial cell wall, induces the release of TNF-α (see, e.g., Martich et al., 1991).

Overproduction of inflammatory cytokines, such as TNF-α, has been linked to inflammatory disorders such as Crohn's disease (CD) and inflammatory bowel disease (see, e.g., Kam et al., 2000; Nakamura et al., 2006), rheumatoid arthritis (see, e.g., Keffer et al., 1991; McCann et al., 2010), septic shock (see, e.g., Link et al., 2008; Shapira et al., 1996), asthma (see, e.g., Berry et al., 2007), chronic bronchitis (CB), chronic obstructive pulmonary disease (COPD), acute lung injury (ALI), and acute respiratory distress syndrome (ARDS) (see, e.g., Mukhopadhyay et al., 2006). Reduction of TNF-α levels has been associated with improvement in these conditions.

The activity of compound TBAP-01 in LPS-stimulated TNFα release from human peripheral blood mononuclear cells (PBMCs) was determined at Argenta/Charles River, Cowley, Oxford, according to the contractor's protocol. PBMCs were isolated from healthy human volunteer blood using a standard density gradient centrifugation technique. PBMCs were suspended in medium and dispensed into a 96-well plate and incubated at 37° C. for 3 hours in a humidified incubator. After incubation, the medium was replaced and test compound, reference compound (BIRB796), or the appropriate vehicle were added to the cells and the plate incubated at 37° C. for 1 hour. After incubation, LPS (*E coli* 0111:84, 10 ng/mL), or an appropriate vehicle control were then be added to the cells and the plate returned to the incubator for overnight incubation. After incubation, the plate was centrifuged at 300×g for 4 minutes at room temperature. Cell free supernatants were removed and stored (frozen) until assayed for TNF-α levels using a commercially available EUSA kit (R&D Systems).

The test compound was dissolved in DMSO and aliquots were stored frozen. A separate aliquot was used for each experiment. For each experiment, the test compound was diluted in DMSO (to 1000 times the final assay concentration), and then diluted into cell culture medium to give the required concentrations whilst maintaining a constant DMSO concentration (final concentration of 0.1% DMSO in the assay).

An 8-point dose-response curve was performed, with three separate experiments (n=3). The effect of the test compound in each experiment was expressed as a percentage inhibition of the LPS-stimulated response. Percentage inhibition data for each test compound in each experiment was pooled to determine a single $IC_{50}$ value for each test compound.

Compound TBAP-01 was found to exhibit potent inhibition using this assay, with an $IC_{50}$ of 3.4 nM and a 95% Confidence Interval of 2.0-5.7 nM.

Comparison Data—1

Data for TBAP-01 and structurally related known compounds (AA-04 in Springer et al., 2011; and AA-018, AA-019, AA-062, AA-084 in Springer et al., 2009) are summarised below.

TABLE 18

In Vivo Efficacy Data

| | | Tumour/Control Ratio | | | |
| | | Oral | | IP | |
| Compound | Cell Line | 1 × MED | 0.5 × MED | 1 × MED | 0.5 × MED |
| --- | --- | --- | --- | --- | --- |
| TBAP-01 | mutBRAF A375M | 0.07 | 0.47 | — | — |
| TBAP-01 | mutBRAF WM266.4 | 0.08 | 0.21 | — | — |
| TBAP-01 | mutRAS SW620 | 0.40 | | | |
| TBAP-01 | RM-17 (LINE 3) | 0.18 | | | |
| TBAP-01 | RM-2 (LINE 2) | 0.13 | | | |
| TBAP-01 | A375R | 0.33 | | | |
| TBAP-01 | PDAC R172H | 0.45 | | | |
| AA-018 | mutBRAF A375M | — | — | 0.52 | — |
| AA-019 | mutBRAF A375M | 0.15 | — | — | — |
| AA-019 | mutBRAF WM266.4 | 0.14 | 0.41 | — | 0.34 |
| AA-019 | mutRAS SW620 | 0.52 | | | |
| AA-019 | RM-17 (LINE 3) | 0.43 | | | |
| AA-019 | RM-2 (LINE 2) | 0.19 | | | |
| AA-019 | A375R | 0.40 | | | |
| AA-019 | PDAC R172H | 0.56 | | | |
| AA-062 | mutBRAF A375M | 0.66 | | — | — |

(MED = maximum effective dose)

TABLE 19

Comparison of Potency in Cell Lines

| Class | Cell line | TBAP-01 $GI_{50}$ (μM) | AA-019 $GI_{50}$ (μM) |
| --- | --- | --- | --- |
| BRAF mutant | A375 | 0.178 | 0.249 |
| | A375/R | 0.839 | 1.897 |
| | A375(X) | 0.163 | 0.372 |
| | A375(X)/R | 0.252 | 0.501 |
| NRAS mutant | DO4 | 0.275 | 0.573 |
| | SBCL2 | 0.719 | 1.159 |
| Resistant to Approved BRAF Inhibitors | LP2-CL2 (LINE 1) | 0.043 | 0.684 |
| | RM-2 (LINE 2) | 0.569 | 1.39 |
| | RM-17 (LINE 3) | 2.6 | 3.0 |

TABLE 20

Comparison of Assay Data

| Compound | BRAF V600E Kinase Assay $IC_{50}$ (μM) | P-ERK Cell-Based Assay $IC_{50}$ (μM) | SRB Assay $IC_{50}$ (μM) | Herg Inhibition $IC_{50}$ (μM) |
| --- | --- | --- | --- | --- |
| TBAP-01 | 0.062 | 0.018 | 0.062 | >100 |
| AA-04 | 0.650 | 0.137 | 0.291 | — |
| AA-018 | 0.064 | 0.024 | 0.015 | >100 |

TABLE 20-continued

Comparison of Assay Data

| Compound | BRAF V600E Kinase Assay IC$_{50}$ (µM) | P-ERK Cell-Based Assay IC$_{50}$ (µM) | SRB Assay IC$_{50}$ (µM) | Herg Inhibition IC$_{50}$ (µM) |
|---|---|---|---|---|
| AA-019 | 0.055 | 0.028 | 0.008 | >100 |
| AA-062 | 0.079 | 0.063 | 0.037 | >100 |
| AA-084 | 0.71 | 0.15 | 0.30 | 53 |

TABLE 21

Comparison of Pharmacokinetic Data

| Compound | Thermodynamic solubility @ pH 7.4 (mg/mL) | C$_{max}$ (nM) (10 mg/kg po) | AUC (h * nmol/L) (10 mg/kg po) | F % mouse | MTD in mice (mg/kg) (qd × 28 days) |
|---|---|---|---|---|---|
| TBAP-01 | 0.066 | 68831 | 509747 | 42 | 40-50 po |
| AA-018 | — | 33640 | 461407 | 24 | 10 ip |
| AA-019 | 0.035 | 40503 | 416286 | 54 | 20 po |
| AA-062 | | 1055590 | 5888243 | 100 | 50 po |

TABLE 22

Comparison of Biomarker Data

| Compound | Cell line | pERK (% residual vs vehicle control; 24 daily doses; 1 h post-dose) | pSRC (% residual vs vehicle control, 4 daily doses; 4 h post-dose) |
|---|---|---|---|
| TBAP-01 | PDAC R172H | 15 | 20 |
| AA-019 | PDAC R172H | >100 (No reduction) | 53 |

Comparison Data—2

As compared to Compound AA-04 in Springer et al., 2011, TBAP-01 is:

(a) 10-fold more potent on the BRAF kinase assay;

(b) 8-fold more potent on the pERK cellular assay; and (c) 5-fold more potent on the cell proliferation inhibition assay.

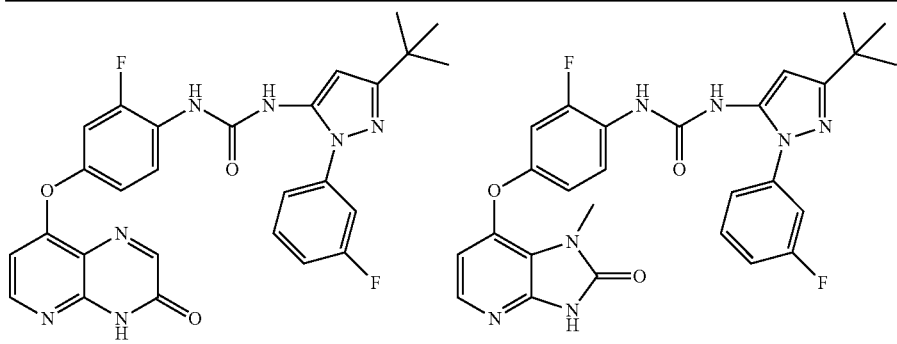

Comparison Data—3

As compared to Compound AA-018 in Springer et al., 2009, TBAP-01 is:

(a) 7-fold more effective on mutant BRAF melanoma xenograft A375M at the maximum effective dose; and (b) 2-fold higher oral bioavailability.

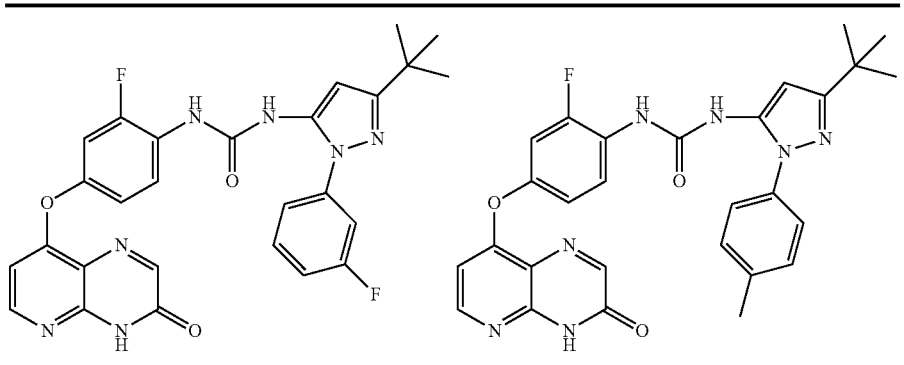

Comparison Data—4

As compared to Compound AA-019 in Springer et al., 2009, TBAP-01 is:

(a) tolerated in vivo at doses 2-fold higher (i.e., 40-50 mg/kg), despite having a higher $C_{max}$ and AUC than AA-019 at the same dose;

(b) up to 16-fold more potent in cell proliferation inhibition on BRAF-mutant naive or approved-drug resistant cell lines and mutant RAS cell lines;

(c) 2-fold more soluble (i.e., has 2-fold higher thermodynamic solubility);

(d) 2-fold more effective on mutant BRAF melanoma xenograft A375M and mutant BRAF melanoma xenograft WM266.4 at the maximum effective dose;

Comparison Data—4

As compared to Compound AA-019 in Springer et al., 2009, TBAP-01 is:

(c) 2-fold more soluble (i.e., has 2-fold higher thermodynamic solubility);

(d) 2-fold more effective on mutant BRAF melanoma xenograft A375M and mutant BRAF melanoma xenograft WM266.4 at the maximum effective dose;

(e) 1.2-fold more effective on mutant RAS colorectal xenograft SW620 at the maximum effective dose;

(f) 1.2-1.5-fold more effective on vemurafenib-resistant patient derived mutant BRAF melanoma xenograft RM-2 (LINE 2) and mutant BRAF melanoma xenograft A375R at the maximum effective dose; and (g) 2.4-fold more effective on dabrafenib+trametinib-resistant patient derived mutant BRAF melanoma xenograft RM-17 (LINE 3) at the maximum effective dose.

(h) >6.5-fold more effective in inhibiting the pERK biomarker in the pancreatic PDAC R172H allograft at the maximum effective dose.

(i) 2.5-fold more effective in inhibiting the pSRC biomarker in the pancreatic PDAC R172H allograft at the maximum effective dose.

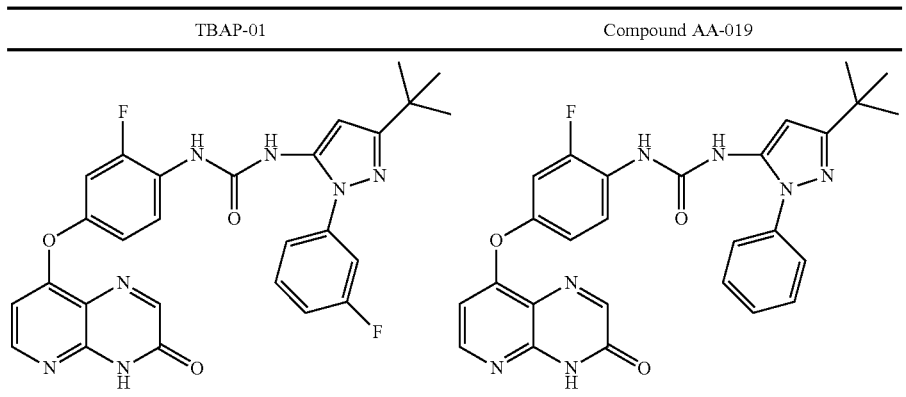

(a) tolerated in vivo at doses 2-fold higher (i.e., 40-50 mg/kg), despite having a higher $C_{max}$ and AUC than AA-019 at the same dose;

(b) up to 16-fold more potent in cell proliferation inhibition on BRAF-mutant naive or approved-drug resistant cell lines and mutant RAS cell lines;

Comparison Data—5

As compared to Compound AA-062 in Springer et al., 2009, TBAP-01 is 9-fold more effective on mutant BRAF melanoma xenograft A375M at the maximum effective dose. This is surprising and unexpected because AA-062 has a 5-fold higher $C_{max}$ and a 12-fold higher AUC as compared to TBAP-01.

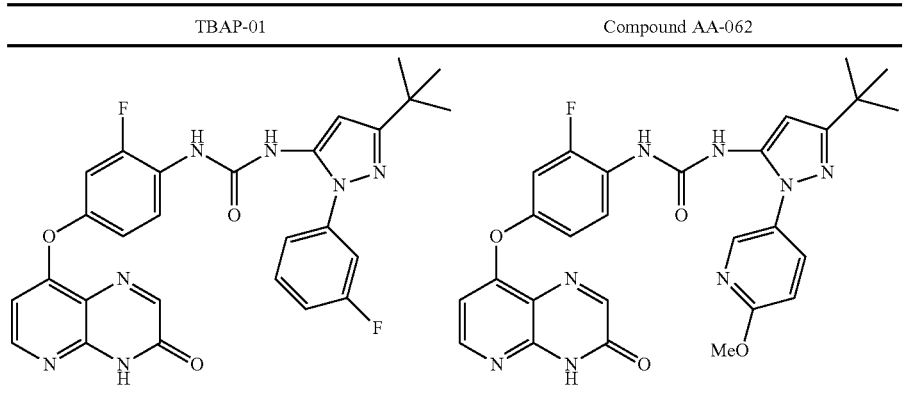

Comparison Data—6

As compared to Compound AA-084 in Springer et al., 2009, TBAP-01 is:
(a) 11-fold more potent on the BRAF kinase assay;
(b) 8-fold more potent on the pERK cellular assay; and
(c) 5-fold more potent on the cell proliferation inhibition assay.

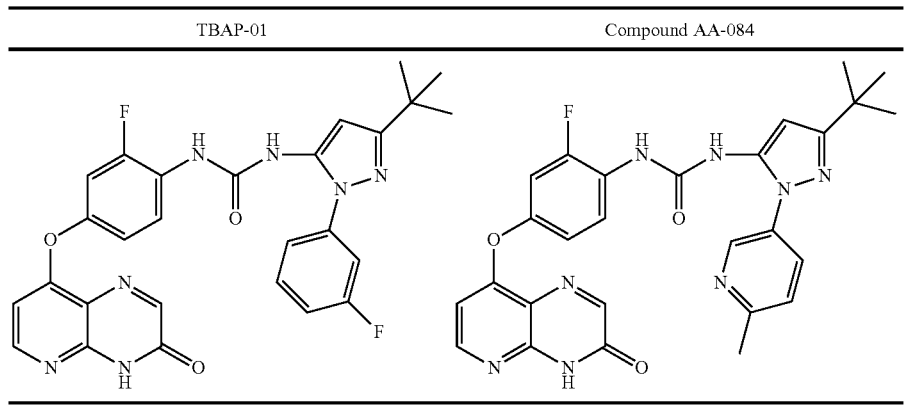

| TBAP-01 | Compound AA-084 |

The foregoing has described the principles, preferred embodiments, and modes of operation of the present invention. However, the invention should not be construed as limited to the particular embodiments discussed. Instead, the above-described embodiments should be regarded as illustrative rather than restrictive. It should be appreciated that variations may be made in those embodiments by workers skilled in the art without departing from the scope of the present invention.

REFERENCES

A number of publications are cited herein in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

Akula et al., 2004, "Raf promotes human herpesvirus-8 (HHV-8/KSHV) infection", *Oncogene*. Vol. 23, pp. 5227-5241.

Alitalo et al., 1996, "Promoter for the receptor tyrosine kinase, Tie", U.S. Pat. No. 5,877,020 granted 2 Mar. 1999.

Alon et al., 1995, "Vascular endothelial growth factor acts as a survival factor for newly formed retinal vessels and has implications for retinopathy of prematurity", *Nature Med.* Vol. 1, pp. 1024-1028.

Anastasaki et al., 2012, "Continual low-level MEK inhibition ameliorates cardio-facio-cutaneous phenotypes in zebrafish", *Disease Models & Mechanisms*, Vol. 5, pp. 546-552.

Antony et al., 2013, "C-RAF Mutations Confer Resistance to RAF Inhibitors", *Cancer Research*, Vol. 73, pp. 4840-4851.

Arcaini et al., 2012, "The BRAFV600E mutation in hairy cell leukemia and other mature B-cell neoplasms", *Blood*, Vol. 119, pp. 188-191.

Asrih et al., 2013, "Role of Mitogen-Activated Protein Kinase Pathways in multifactorial adverse cardiac remodeling associated with Metabolic Syndrome", *Mediators of Inflammation*, Vol. 2013, Article ID No. 367245.

Badalian-Very et al., 2011, "Recent advances in the understanding of Langerhans cell histiocytosis", *British Journal of Haematology*, Vol. 156, pp. 163-172.

Belgore et al., 2004, "Localisation of members of the vascular endothelial growth factor (VEGF) family and their receptors in human atherosclerotic arteries", *J. Clin. Pathol.*, Vol. 57, pp. 266-272.

Benn et al., 1994, "Hepatitis B virus HBx protein activates Ras-GTP complex formation and establishes a Ras, Raf, MAP kinase signaling cascade", *PNAS*, Vol. 91, pp. 10350-10354.

Berry et al., 2007, "TNF-alpha in asthma", *Curr. Opin. Pharmacol.*, Vol. 7, No. 3, pp. 279-282.

Bos et al., 1989, "Ras oncogenes in human cancer: a review", *Cancer Research*. Vol. 49, pp. 4682-4689.

Bridges et al., 2000, "Treatment of asthma with MEK inhibitors", international (PCT) patent application publication number WO 00/40235, published 13 Jul. 2000.

Byeon et al., 2012, "The role of Src kinase in macrophage-mediated inflammatory responses", *Mediators of Inflammation*, Vol. 2012, Article ID No. 512926.

Calhoun et al., 2003, "BRAF and FBXW7 (CDC4, FBW7, AGO, SEL10) Mutations in Distinct Subsets of Pancreatic Cancer", *American Journal of Pathology*, Vol. 163, pp. 1255-1260.

Cantin et al., 2007, "Pyrazolyl urea derivatives useful in the treatment of cancer", international (PCT) patent application publication number WO 2007/059202 A2, published 24 May 2007.

Cantrell, 2003, "GTPases and T cell activation", *Immunol. Rev.*, Vol. 192, pp. 122-130.

Chan et al., 1996, "Regulation of antigen receptor signal transduction by protein tyrosine kinases", *Curr. Opin. Immunol.*, Vol. 8, No. 3, pp. 394-401.

Chapman et al., 2011, "Improved survival with vemurafenib in melanoma with BRAF V600E mutation". *New England Journal of Medicine*. Vol. 364, pp. 2507-2516.

Chapman et al., 2011, "Initial genome sequencing and analysis of multiple myeloma", *Nature*, Vol. 471, pp. 467-472.

Chun et al., 2002, "Pharmaceutical composition for prevention and treatment of joint arthritis and a screening method thereof", international patent publication number WO 02/102367, published 27 Feb. 2002.

Ciampi et al., 2005, "Oncogenic AKAP9-BRAF fusion is a novel mechanism of MAPK pathway activation in thyroid cancer", *J. Clin. Invest.*, Vol. 115, pp. 94-101.

Colville-Nash and Scott, 1992, "Angiogenesis and rheumatoid arthritis: pathogenic and therapeutic implications", *Ann. Rhum. Dis.*, Vol. 51, p. 919.

Cooper et al., 1994, "Membrane-associated tyrosine kinases as molecular switches", *Semin. Cell Biol.*, Vol. 5, No. 6, pp. 377-387.

Corcoran et al., 2010, "BRAF Gene Amplification Can Promote Acquired Resistance to MEK Inhibitors in Cancer Cells Harboring the BRAF V600E Mutation", *Sci. Signal.*, Vol. 3, ra84.

Coulthard et al., 2009, "p38MAPK: stress responses from molecular mechanisms to therapeutics", *Trends Mol. Med.*, Vol. 15, pp. 369-379.

Courtneidge et al., 1993, "The Src family of protein tyrosine kinases: regulation and functions". *Dev. Suppl.*, pp. 57-64.

Cuadrado et al., 2010, "Mechanisms and functions of p38 MAPK signalling", *Biochem. J.*, Vol. 429, pp. 403-417.

Damodar Reddy et al., 2001, "Role of MAP kinase pathways in primitive neuroectodermal tumours", *Anticancer Research*, Vol. 21, pp. 2733-2738.

Davies et al., 1996, "Raf and Mitogen-activated Protein Kinase Regulate Stellate Cell Collagen Gene Expression", *J. Biol. Chem.*, Vol. 271, pp. 11039-11042.

Davies et al., 2002, "Mutations of the BRAF gene in human cancer", *Nature*, Vol. 417, pp. 949-954.

Davis et al., 1994, "Tie-2 ligand 1", U.S. Pat. No. 5,879,672 granted 9 Mar. 1999.

Davis et al., 1994, "TIE-2 ligand, and method of making", U.S. Pat. No. 5,521,073 granted 28 May 1996.

Davis et al., 1996, "Isolation of Angiopoietin-1, a Ligand for the TIE2 Receptor, by Secretion-Trap Expression Cloning", *Cell*, Vol. 87, pp. 1161-1169.

Denekamp, 1993, "Angiogenesis, neovascular proliferation and vascular pathophysiology as targets for cancer therapy", *Br. J. Rad.*, Vol. 66, pp. 181-196.

Dhomen et al., 2009, "Oncogenic Braf induces melanocyte senescence and melanoma in mice", *Cancer Cell*, Vol. 15, pp. 294-303.

Dixon et al., 2001, "Method for treating chronic pain using MEK inhibitors", international (PCT) patent application publication number WO 01/05392, published 25 Jan. 2001.

Downward et al., 2003, "Targeting RAS signalling pathways in cancer therapy", *Nature Reviews Cancer*. Vol. 3, pp. 11-22.

Dudley et al., 2000, "Treatment of arthritis with MEK inhibitors", international (PCT) patent application publication number WO 00/35436, published 22 Jun. 2000.

Ellis et al., 2008, "VEGF-targeted therapy: mechanisms of anti-tumour activity", *Nature Reviews Cancer*, Vol. 8, pp. 579-591.

Falchook et al., 2012, "Dabrafenib in patients with melanoma, untreated brain metastases, and other solid tumours: a phase 1 dose-escalation trial", *The Lancet*, Vol. 379, pp. 1893-1901.

Fernandes-Medarde, 2011, "Ras in Cancer and Developmental Diseases", *Genes & Cancer*, Vol. 2, pp. 344-358.

Fidler and Ellis, 1994, "The implications of angiogenesis for the biology and therapy of cancer metastasis", *Cell*, Vol. 79, pp. 185-188.

Flaherty et al., 2010, "Inhibition of mutated, activated BRAF in metastatic melanoma", *New England Journal of Medicine*, Vol. 363, pp. 809-819.

Flynn et al., 2008, "Enzyme modulators and treatments", US patent application publication number US 2008/0113967 A1, published 15 May 2008.

Folkman et al., 1992, "Angiogenesis", *J. Biol. Chem.*, Vol. 267, pp. 10931-10934.

Folkman, 1992, "The role of angiogenesis in tumour growth", *Semin. Cancer Biol.*, Vol. 3, pp. 65-71.

Folkman, 1995, "Angiogenesis in cancer, vascular, rheumatoid and other disease", *Nature Medicine*, Vol. 1, pp. 27-31.

Folkman, 1997, "Angiogenesis and angiogenesis inhibition: an overview", *EXS*, Vol. 79, pp. 1-81.

Friedlander et al., 1995, "Definition of two angiogenic pathways by distinct alpha v integrins", *Science*, Vol. 270, pp. 1500-1502.

Fujita et al., 2004, "ERK and p38 mediate high-glucose-induced hypertrophy and TGF-α expression in renal tubular cells", *Am. J. Physiol. Renal. Physiol.*, Vol. 286, p. F120.

Fukuda et al., 2007, "Epstein-Barr Virus Latent Membrane Protein 2A Mediates Transformation through Constitutive Activation of the Ras/PI3-K/Akt Pathway", *J. Virol.*, Vol. 81, pp. 9299-9306.

Furuta et al., 2012, "Nitrogenated aromatic heterocyclic ring derivative", international (PCT) patent application publication number WO 2012/008564 A1, published 19 Jan. 2012.

Garnett et al., 2004, "Guilty as charged: B-RAF is a human oncogene", *Cancer Cell*, Vol. 6, pp. 313-319.

Gaudi et al., 2011, "Molecular Bases of Cutaneous and Uveal Melanomas", *Pathology Research International*, Vol. 2011, Article ID No. 159421.

Genot et al., 2000, "Ras regulation and function in lymphocytes", *Curr. Opin. Immunol.*, Vol. 12, pp. 289-294.

Geppert et al., 1994, "Lipopolysaccharide signals activation of Tumour Necrosis Factor biosynthesis through the Ras/Raf-1/MEK/MAPK pathway", *Mol. Med.*, Vol. 1, pp. 93-103.

Gilbertsen et al., 2000, "Use of a MEK inhibitor for preventing transplant rejection", international (PCT) patent application publication number WO 00/35435, published 22 Jun. 2000.

Girotti et al., 2013, "Inhibiting EGF receptor or SRC family kinase signaling overcomes BRAF inhibitor resistance in melanoma", *Cancer Discovery*. Vol. 3, pp. 158-167.

Godowski et al., 1997, "Tie ligand homologues", U.S. Pat. No. 6,030,831granted 29 Feb. 2000.

Graf et al., 1997, "Mitogen-Activated Protein Kinase Activation Is Involved in Platelet-Derived Growth Factor-Directed Migration by Vascular Smooth Muscle Cells", *Hypertension*, Vol. 29, pp. 334-339.

Gray-Schopfer et al., 2007, "Melanoma biology and new targeted therapy", *Nature*, Vol. 445, pp. 851-857.

Greger et al., 2012, "Combinations of BRAF, MEK, and PI3K/mTOR Inhibitors Overcome Acquired Resistance to the BRAF Inhibitor GSK2118436 Dabrafenib, Mediated by NRAS or MEK Mutations", *Molecular Cancer Therapeutics*, Vol. 11, pp. 909-920.

Grosios et al., 2004, "Angiogenesis inhibition by the novel VEGF receptor tyrosine kinase inhibitor, PTK787/ZK222584, causes significant anti-arthritic effects in models of rheumatoid arthritis", *Inflamm. Res.*, Vol. 53, pp. 133-142.

Gu et al., 2013, "Use of organic compound for the treatment of Noonan syndrome", international (PCT) patent application publication number WO 2013/033133, published 7 Mar. 2013.

Haase et al., 2001, "A role for mitogen-activated protein kinase activation by integrins in the pathogenesis of psoriasis", *J. Clin. Invest.*, Vol. 108, pp. 527-536.

Haroche et al., 2012, "High prevalence of BRAF V600Emutations in Erdheim-Chester disease but not in other non-Langerhans cell histiocytoses", *Blood*. Vol. 120, pp. 2700-2703.

Hatzivassiliou et al., 2011, "Determining sensitivity of cells to B-Raf inhibitor treatment by detecting K-ras mutation and RTK expression levels", international (PCT) patent application publication number WO 2011/028540 published 10 Mar. 2011.

Hatzivassiliou et al., 2011, "Determining sensitivity of cells to B-Raf inhibitor treatment by detecting K-ras mutation and RTK expression levels", international (PCT) patent application publication number WO 2011/028540 published 10 Mar. 2011.

Heidorn et al., 2010, "Kinase-dead BRAF and oncogenic RAS cooperate to drive tumour progression through CRAF", *Cell*. Vol. 140, pp. 209-221.

Hu et al., 2011, "Mutation that blocks ATP binding creates a pseudokinase stabilizing the scaffolding function of kinase suppressor of Ras, CRAF and BRAF", *PNAS*. Vol. 18, pp. 6067-6072.

Hwang et al., 2004, "Over-expression of c-raf-1 proto-oncogene in liver cirrhosis and hepatocellular carcinoma", *Hepatology Research*, Vol. 29, pp. 113-121.

Ingber et al., 1990, "Synthetic analogues of fumagillin that inhibit angiogenesis and suppress tumour growth", *Nature*, Vol. 348, pp. 555-557.

Inoue et al., 1998, "Vascular endothelial growth factor (VEGF) expression in human coronary atherosclerotic lesions: possible pathophysiological significance of VEGF in progression of atherosclerosis", *Circulation*, Vol. 98, pp. 2108-2116.

Jaffee et al., 2000, "Inhibition of MAP Kinase Kinase (MEK) Results in an Anti-inflammatory Response in Vivo", *Biochem. Biophys. Res. Com.*, Vol. 268, p. 647.

Jessen et al., 2013, "MEK inhibition exhibits efficacy in human and mouse neurofibromatosis tumours", *Journal of Clinical Investigation*, Vol. 123, pp. 340-347.

Ji et al., 2002, "ERK MAP Kinase Activation in Superficial Spinal Cord Neurons Induces Prodynorphin and NK-1 Upregulation and Contributes to Persistent Inflammatory Pain Hypersensitivity", *J. Neurosci.*, Vol. 22, p. 478.

Jo et al., 2005, "MEK inhibitor, U0126, attenuates cisplatin-induced renal injury by decreasing inflammation and apoptosis, *Kidney Intl.*, Vol. 67, pp. 458-466.

Johnson et al., 2001, "The role of MKK1/2 kinase activity in human cytomegalovirus infection", *J. Gen. Virol.*, Vol. 82, pp. 493-497.

Kahlon et al., 1992, "Angiogenesis in atherosclerosis", *Can. J. Cardiol.*, Vol. 8, p. 60.

Kam et al., 2000, "TN F-alpha antagonists for the treatment of Crohn's disease", *Expert Opin. Pharmacother.*, Vol. 1, pp. 615-622.

Karim et al., 2006, "Impaired inflammatory pain and thermal hyperalgesia in mice expressing neuron-specific dominant negative mitogen activated protein kinase kinase (MEK)", *Mol. Pain.*, Vol. 2, p. 2.

Keffer et al., 1991, "Transgenic mice expressing human necrosis factor: a predictive genetic model of arthritis", *EMBO J.*, Vol. 10, No. 13, pp. 4025-4031.

Kjetil et al., 2013, "Methods and compositions for inhibition of activation of regulatory T cells", international (PCT) patent application publication number WO 2013/001372, published 3 Jan. 2013.

Kotoula et al., 2009, "Mutational analysis of the BRAF, RAS and EGFR genes in human adrenocortical carcinomas", *Endocrine-Related Cancer*, Vol. 16, pp. 565-572.

Li et al., 1998, "Activation of NF-kB via a Src-dependent Ras-MAPK-pp90rsk pathway is required for *Pseudomonas aeruginosa*-induced mucin overproduction in epithelial cells", *PNAS*, Vol. 95, pp. 5718-5723.

Lin et al., 2010, "VEGF and its receptor-2 involved in neuropathic pain transmission mediated by P2X2/3 receptor of primary sensory neurons", *Brain Research Bulletin*, Vol. 83, pp. 284-291.

Lindauer et al., 2012, "Dasatinib", *Recent Results in Cancer Research*, Vol. 184, pp. 83-102.

Link et al., 2008, "Phosphodiesterase 4 inhibition but not beta-adrenergic stimulation suppresses tumor necrosis factor-alpha release in peripheral blood mononuclear cells in septic shock", *Crit. Care*. Vol. 12, No. 6, R159.

Long et al., 2011, "Prognostic and clinicopathologic associations of oncogenic BRAF in metastatic melanoma", *J. Clin. Oncol.*, Vol. 29, No. 10, pp. 1239-1246.

Lorenz et al., 2009, "Cardiac hypertrophy: Targeting Raf/MEK/ERK1/2-signaling", *The International Journal of Biochemistry & Cell Biology*, Vol. 41, pp. 2351-2355.

Lowenberg et al., 2005, "Specific Inhibition of c-Raf Activity by Semapimod Induces Clinical Remission in Severe Crohn's Disease", *J. Immunol.*, Vol. 175, pp. 2293-2300.

Luo et al., 2002, "Coxsackievirus B3 Replication Is Reduced by Inhibition of the Extracellular Signal-Regulated Kinase (ERK) Signaling Pathway", *J. Virol.*, Vol. 76, pp. 3365-3373.

Ma et al., 2005, "The ERK/MAPK pathway, as a target for the treatment of neuropathic pain", *Expert Opin Ther Targets*, Vol. 9, p. 699.

Maddahi et al., 2010, "Cerebral ischemia induces microvascular pro-inflammatory cytokine expression via the MEK/ERK pathway, *J. Neuroinflammation*, Vol. 7, pp. 1-14.

Mammas et al., 2005, "Involvement of the ras genes in female genital tract cancer (Review)", *International Journal of Oncology*, Vol. 26, pp. 1241-1255.

Martich et al., 1991, "Detection of interleukin 8 and tumor necrosis factor in normal humans after intravenous endotoxin: the effect of antiinflammatory agents", *J. Exp. Med.*, Vol. 173, pp 1021-1024.

Martin et al., 2010, "Update on lymphocyte specific kinase inhibitors: a patent survey", *Expert Opin. Ther. Pat.*, Vol. 20, pp. 1573-1593.

Masabumi et al., 2013, "Vascular endothelial growth factor and its receptor system: physiological functions in angiogenesis and pathological roles in various diseases", *J. Biochem.*, Vol. 153, pp. 13-19.

McCann et al., 2010, "Apremilast, a novel PDE4 inhibitor, inhibits spontaneous production of tumour necrosis factor-alpha from human rheumatoid synovial cells and ameliorates experimental arthritis", *Arthritis Res. Ther.*, Vol. 12, No. 3, R107.

McKay et al., 2011, "Complexity in KSR function revealed by Raf inhibitor and KSR structure studies", *Small GTPases*, Vol. 2, pp. 276-281.

McMahon et al., 2000, "VEGF receptor signaling in tumour angiogenesis", *The Oncologist*, Vol. 5, pp. 3-10.

Mei et al., 2006, "Distribution, levels and phosphorylation of Raf-1 in Alzheimer's disease", *J. Neurochem.*, Vol. 99, pp. 1377-1388.

Mercer et al., 2006, "Emerging role of MAP kinase pathways as therapeutic targets in COPD", *Int. J. of COPD*, Vol. 1, pp. 137-150.

Metzner et al., 2012, "Fibroblast Growth Factor Receptors as Therapeutic Targets in Human Melanoma: Synergism with BRAF Inhibition", *Journal of Investigative Dermatology*, Vol. 131, pp. 2087-2095.

Meyers et al., 1996, "FGFR2 exon IIIa and IIIc mutations in Crouzon, Jackson-Weiss, and Pfeiffer syndromes: evidence for missense changes, insertions, and a deletion due to alternative RNA splicing", *Am. J. Hum. Genet.*, Vol. 58, pp. 491-498.

Milella et al., 2001, "Therapeutic targeting of the MEK/MAPK signal transduction module in acute myeloid leukemia", *Journal of Clinical Investigation*, Vol. 108, pp. 851-859.

Miura et al., 2004, "Simvastatin suppresses coronary artery endothelial tube formation by disrupting Ras/Raf/ERK signaling", *Atherosclerosis*, Vol. 175, pp. 235-243.

Montagut et al., 2008, "Elevated CRAF as a Potential Mechanism of Acquired Resistance to BRAF Inhibition in Melanoma", *Cancer Research*, Vol. 68, pp. 4853-4861.

Mukherjee et al., 2005, "Raf-1 expression may influence progression to androgen insensitive prostate cancer", *Prostate*, Vol. 64, pp. 101-107.

Mukhopadhyay et al., 2006, "Role of TNFalpha in pulmonary pathophysiology", *Resoir. Res.*, Vol. 7, p. 125.

Murray et al., 2011, "Respiratory formulations and compounds for use therein", international (PCT) patent application publication number WO 2011/158044 A2, published 22 Dec. 2011.

Mustonen et al., 1995, "Endothelial receptor tyrosine kinases involved in angiogenesis", *J. Cell Biol.*, Vol. 129, pp. 895-898.

Nakamura et al., 2006, "Novel strategies for the treatment of inflammatory bowel disease: Selective inhibition of cytokines and adhesion molecules", *World J. Gastroenterol.*, Vol. 12, pp. 4628-4235.

Nazarian et al., 2010, "Melanomas acquire resistance to B-RAF(V600E) inhibition by RTK or N-RAS upregulation", *Nature*, Vol. 468, pp. 973-979.

Niculescu-Duvaz et al., 2006, "Imidazo[4,5-b]pyridin-2-one and oxazolo[4,5-b]pyridin-2-one compounds and analogs thereof as therapeutic compounds", international (PCT) patent application publication number WO 2006/043090 A1, published 27 Apr. 2006.

Niculescu-Duvaz et al., 2007, "Imidazo[4,5-b]pyridin-2-one and oxazolo[4,5-b]pyridin-2-one compounds and analogs thereof as therapeutic compounds", international (PCT) patent application publication number WO 2007/125330 A1, published 8 Nov. 2007.

Niculescu-Duvaz et al., 2009, "Aryl-quinolyl compounds and their use", international (PCT) patent application publication number WO 2009/130487 A1, published 29 Oct. 2009.

O'Reilly et al., 1994, "Angiostatin: a novel angiogenesis inhibitor that mediates the suppression of metastases by a Lewis lung carcinoma.", *Cell*, Vol. 79, pp. 315-328.

Oeztuerk-Winder et al., 2012, "The many faces of p38 mitogen-activated protein kinase in progenitor/stem cell differentiation", *Biochem. J.*, Vol. 445, pp. 1-10.

Ozawa et al., 2001, "Growth factors and their receptors in pancreatic cancer", *Teratog. Carcinoc. Mutagen.*, Vol. 21, pp. 27-44.

Palanisamy et al., 2010, "Rearrangements of the RAF Kinase Pathway in Prostate Cancer, Gastric Cancer and Melanoma", *Nat. Med.*, Vol. 16, pp. 793-798.

Partanen et al., 1992, "A novel endothelial cell surface receptor tyrosine kinase with extracellular epidermal growth factor homology domains", *Mol. Cell Biol.*, Vol. 12, pp. 1698-1707.

Partanen et al., 1999, "Functions of Tie1 and Tie2 Receptor Tyrosine Kinases in Vascular Development", *Curr. Topics Microbiol. Immunol.*, Vol. 237, pp. 159-172.

Paulson et al., 1995, "Receptor tyrosine kinases and the regulation of hematopoiesis", *Semin. Immunol.*, Vol. 7, No. 4, pp. 267-277.

Payne et al., 2001, "Human Papillomavirus Type 6b Virus-Like Particles Are Able To Activate the Ras-MAP Kinase Pathway and Induce Cell Proliferation", *J. Virol.*, Vol. 75, pp. 4150-4157.

Peacock et al., 1992, "Angiogenesis inhibition suppresses collagen arthritis", *J. Exp. Med.*, Vol. 175, pp. 1135-1138.

Peacock et al., 1995, "A novel angiogenesis inhibitor suppresses rat adjuvant arthritis", *Cell. Immunol.*, Vol. 160, pp. 178-184.

Pelletier et al., 2003, "In vivo selective inhibition of mitogen-activated protein kinase kinase 1/2 in rabbit experimental osteoarthritis is associated with a reduction in the development of structural changes", *Arthritis & Rheumatism*, Vol. 48, p. 1582-1593.

Peters, 1998, "Vascular Endothelial Growth Factor and the Angiopoietins: Working Together to Build a Better Blood Vessel", *Circ. Res.*, Vol. 83, No. 3, pp. 342-343.

Petrovan et al., 2007, "DNA Vaccination Against VEGF Receptor 2 Reduces Atherosclerosis in LDL Receptor-Deficient Mice", *Arteriosclerosis, Thrombosis, and Vascular Biology*, Vol. 27, pp. 1095-1100.

Pinedo et al., 2000, "The Role of VEGF in Tumour Angiogenesis", *The Oncologist*, Vol. 5, pp. 1-2.

Pinner et al., 2009, "CD44 splice variants in neurodegenerative diseases", international (PCT) patent application publication number WO 2009/007934, published 15 Jan. 2009.

Planz et al., 2001, "MEK-specific inhibitor U0126 blocks spread of Borna disease virus in cultured cells", *J. Virol.*, Vol. 75, pp. 4871-4877.

Pleschka et al., 2001, "Influenza virus propagation is impaired by inhibition of the Raf/MEK/ERK signalling cascade", *Nature Cell Biology*, Vol. 3, pp. 301-305.

Plomp et al., 1998, "Pfeiffer syndrome type 2: further delineation and review of the literature", *Am. J. Med. Genet.*, Vol. 75, pp. 245-251.

Poulikakos et al., 2010, "RAF inhibitors transactivate RAF dimers and ERK signalling in cells with wild-type BRAF", *Nature*, Vol. 464, pp. 427-430.

Poulikakos et al., 2011, "RAF inhibitor resistance is mediated by dimerization of aberrantly spliced BRAF(V600E)", *Nature*, Vol. 480, pp. 387-390.

Powers et al., 2000, "Fibroblast growth factors, their receptors and signaling", *Endocr. Relat. Cancer*, Vol. 7, pp. 165-197.

Riva et al., 1995, "Differential c-myc, c-jun, c-raf and p53 expression in squamous cell carcinoma of the head and neck: Implication in drug and radioresistance", *European Journal of Cancer Part B: Oral Oncology*, Vol. 31, pp. 384-391.

Rotsos et al., 2008, "Cystoid macular edema", *Clin. Ophthalmol.*, Vol. 2, pp. 919-930.

Rubinstein et al., 2010, "Incidence of the V600K mutation among melanoma patients with BRAF mutations, and potential therapeutic response to the specific BRAF inhibitor PLX4032", *J. Transl. Med.*, Vol. 8, p. 67.

Salama et al., 2013, "BRAF in Melanoma: Current strategies and future directions", *Clinical Cancer Research*, Vol. 19, No. 16, pp. 4326-4334.

Schindler et al., 2011, "Analysis of BRAF V600E mutation in 1,320 nervous system tumours reveals high mutation frequencies in pleomorphic xanthoastrocytoma, ganglioglioma and extra-cerebellar pilocytic astrocytoma", *Acta Neuropathologica*, Vol. 121, pp. 397-405.

Schreck et al., 2006, "Raf kinases: Oncogenesis and drug discovery", *International Journal of Cancer*, Vol. 119, pp. 2261-2271.

Shakhov et al., 1990, "Kappa B-type enhancers are involved in lipopolysaccharide-mediated transcriptional activation of the tumor necrosis factor alpha gene in primary macrophages", *J. Exp. Med.*, Vol. 171, pp. 35-47.

Shapira et al., 1996, "Protection against endotoxic shock and lipopolysaccharide-induced local inflammation by tetracycline: correlation with inhibition of cytokine secretion", *Infect. Immun.*, Vol. 64, No. 3, pp. 825-828.

Shi et al., 2012, "Melanoma whole-exome sequencing identifies (V600E)B-RAF amplification-mediated acquired B-RAF inhibitor resistance", *Nature Commun.*, Vol. 3, p. 724.

Sievert et al., 2013 "Paradoxical activation and RAF inhibitor resistance of BRAF protein kinase fusions characterizing pediatric astrocytomas", *PNAS*. Vol. 110, pp. 5957-5962.

Smalley et al., 2009, "CRAF inhibition induces apoptosis in melanoma cells with non-V600E BRAF mutations", *Oncogene*, Vol. 28, pp. 85-94.

Smith et al., 2007, "Urea compounds useful in the treatment of cancer", international (PCT) patent application publication number WO 2007/064872 A2, published 7 Jun. 2007.

Smith et al., 2010, "Vascular Endothelial Growth Factor Receptors VEGFR-2 and VEGFR-3 Are Localized Primarily to the Vasculature in Human Primary Solid Cancers", *Clin. Cancer Res.*, Vol. 16, pp. 3548-3561.

Solit et al., 2006, "BRAF mutation predicts sensitivity to MEK inhibition", *Nature*, Vol. 439, pp. 358-362.

Song et al., 2005, "Activation of ERK/CREB pathway in spinal cord contributes to chronic constrictive injury-induced neuropathic pain in rats", *Acta Pharmacol Sin.*, Vol. 26, p. 789.

Sosman et al., 2012, "Survival in BRAF V600-mutant advanced melanoma treated with vemurafenib", *New England Journal of Medicine*, Vol. 366, pp. 707-714.

Springer et al., 2009, "Pyrido[2,3-b]pyrazine-8-substituted compounds and their use", international (PCT) patent application publication number WO 2009/077766 A1, published 25 Jun. 2009.

Springer et al., 2011, "1-(5-tert-Butyl-2-phenyl-2H-pyrazol-3-yl)-3-[2-fluoro-4-(1-methyl-2-oxo-2,3-dihydro-1H-imidazo[4,5-b]pyridin-7-yloxy)-phenyl]urea and related compounds and their use in therapy", international (PCT) patent application publication number WO 2011/092469 A1, published 4 Aug. 2011.

Stratton et al., 2003, "Genes", international (PCT) patent application publication number WO 03/056036 A2 published 10 Jul. 2003.

Straussman et al., 2012, "Tumour micro-environment elicits innate resistance to RAF inhibitors through HGF secretion", *Nature*, Vol. 487, pp. 500-506.

Suijkerbuijk et al., 2010, "Development of novel, highly potent inhibitors of V-RAF murine sarcoma viral oncogene homologue B1 (BRAF): increasing cellular potency through optimization of a distal heteroaromatic group", *J. Med. Chem.*, Vol. 53, pp. 2741-2756.

Sullivan et al., 2011, "BRAF in melanoma: pathogenesis, diagnosis, inhibition, and resistance", *J. Skin Cancer*, Vol. 2011, Article ID No. 423239.

Suri et al., 1996, "Requisite Role of Angiopoietin-1, a Ligand for the TIE2 Receptor, during Embryonic Angiogenesis", *Cell*, Vol. 87, pp. 1171-1180.

Tam et al., 2009, "Blockade of VEGFR2 and Not VEGFR1 Can Limit Diet-Induced Fat Tissue Expansion: Role of Local versus Bone Marrow-Derived Endothelial Cells", *PLoS One*, Vol. 4, e4974.

Taraboletti et al., 1995, "Inhibition of angiogenesis and murine hemangioma growth by batimastat, a synthetic inhibitor of matrix metalloproteinases", *J. Natl. Cancer Inst.*, Vol. 87, p. 293.

Thalhamer et al., 2008, "MAPKs and their relevance to arthritis and inflammation", *Rheumatology*. Vol. 47, pp. 409-414.

Vergani et al., 2011, "Identification of MET and SRC activation in melanoma cell lines showing primary resistance to PLX4032", *Neoplasia*, Vol. 13, pp. 1132-1142.

Vikkula et al., 2004, "Medical use of ras antagonists for the treatment of capillary malformation", international (PCT) patent application publication number WO 2004/083458, published 30 Sep. 2004.

Villanueva et al., 2011, "Acquired resistance to BRAF inhibitors mediated by a RAF kinase switch in melanoma can be overcome by co-targeting MEK and IGF-1R/PI3K", *Cancer Cell*, Vol. 18, pp. 683-695.

Wan et al., 2004, "Mechanism of activation of RAF-ERK signalling pathway by oncogenic mutations in B-RAF", *Cell*, Vol. 116, pp. 855-867.

Wang et al., 1997, "Antisense targeting of basic fibroblast growth factor and fibroblast growth factor receptor-1 in human melanomas blocks intratumoural angiogenesis and tumour growth", *Nature Medicine*, Vol. 3, pp. 887-893.

Wang et al., 2003, "Significant Neuroprotection against Ischemic Brain Injury by Inhibition of the MEK1 Protein Kinase in Mice: Exploration of Potential Mechanism Associated with Apoptosis", *J. Pharmacol. Exp. Ther.*, Vol. 304, p. 172.

Wang et al., 2004, "Inhibition of MEK/ERK 1/2 pathway reduces pro-inflammatory cytokine interleukin-1 expression in focal cerebral ischemia", *Brain Res.*, Vol. 996, p. 55.

Ward et al., 2012, "Targeting oncogenic Ras signaling in hematologic malignancies", *Blood*, Vol. 120, pp. 3397-3406.

Wellbrock et al., 2004, "V599EB-RAF is an oncogene in melanocytes", *Cancer Research*, Vol. 64, pp. 2338-2342.

Whittaker et al., 2010, "A novel, selective and efficacious nanomolar pyridopyrazinone inhibitor of V600EBRAF", *Cancer Research*, Vol. 70, No. 20, pp. 8036 8044.

Wilks et al., 1990, "Structure and function of the protein tyrosine kinases", *Procress in Growth Factor Research*, Vol. 2, pp. 97-111.

Wilson et al., 2012, "Widespread potential for growth-factor-driven resistance to anticancer kinase inhibitors", *Nature*, Vol. 487, pp. 505-509.

Xing, 2013, "Molecular pathogenesis and mechanisms of thyroid cancer", *Nature Reviews Cancer*, Vol. 13, pp. 184-199.

Yancopoulos et al., 1998, "Vasculogenesis, Angiogenesis, and Growth Factors: Ephrins Enter the Fray at the Border", *Cell*, Vol. 93, pp. 661-664.

Yang et al., 1999, "Regulation of Human Immunodeficiency Virus Type 1 Infectivity by the ERK Mitogen-Activated Protein Kinase Signaling Pathway", *J. Virol.*, Vol. 73, pp. 3460-3466.

Yao et al., 1997, "Lipopolysaccharide induction of the tumor necrosis factor-alpha promoter in human monocytic cells. Regulation by Egr-1, c-Jun and NF-kappaB transcription factors", *J. Biol. Chem.*, Vol. 272, pp. 17795-17801.

Yeatman et al., 2004, "A renaissance for SRC", *Nature Reviews Cancer*, Vol. 4, pp. 470-480.

Young et al., 2009, "Ras signaling and therapies", *Advances in Cancer Research*, Vol. 102, pp. 1-17.

Yu et al., 2000, "Loss of fibroblast growth factor receptor 2 ligand binding specificity in Apert syndrome", *Proc. Natl. Acad. Sci. U.S.A.*, Vol. 97, pp. 14536-14541.

Zambon et al., 2010, "Novel hinge binder improves activity and pharmacokinetic properties of BRAF inhibitors", *J. Med. Chem.*, Vol. 53, No. 15, pp. 5639-5655.

Zennadi et al., 2012, "Methods of treating hemoglobinopathies", international (PCT) patent application publication number WO 2012/149547, published 1 Nov. 2012.

Zhang et al., 2012, "Activation of the Ras/Raf/MEK Pathway Facilitates Hepatitis C Virus Replication via Attenuation of the Interferon-JAK-STAT Pathway", *J. Virol.*, Vol. 86, pp. 1544-1554.

Zhang et al., 2012, "Targeting Src family kinases in anticancer therapies: turning promise into triumph", *Trends Pharmacol. Sci. Med.*, Vol. 33, pp. 122-128.

Zouki et al., 2000, "Peroxynitrite induces integrin-dependent adhesion of human neutrophils to endothelial cells via activation of the Raf-1/MEK/Erk pathway", *FASEB J.*, Vol. 15, pp. 25-27.

The invention claimed is:

1. A method of treating a disorder comprising administering to a subject in need of treatment thereof a therapeutically-effective amount of a compound selected from compounds of the following formulae and pharmaceutically acceptable salts and N-oxides thereof:

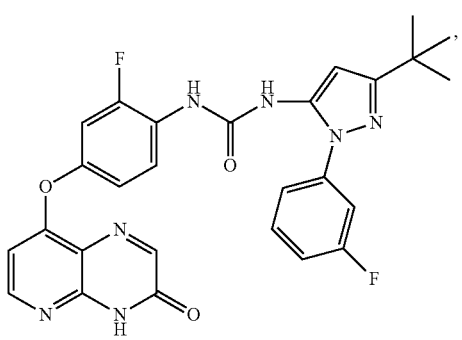

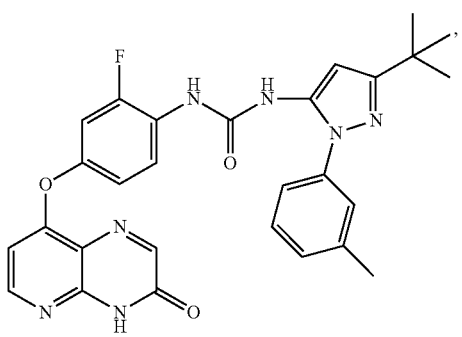

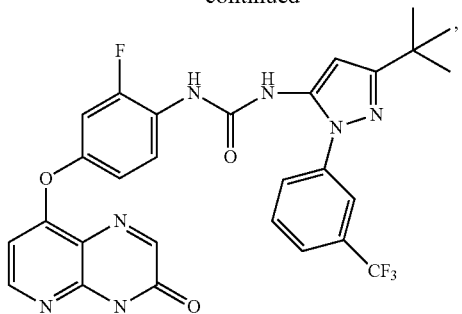

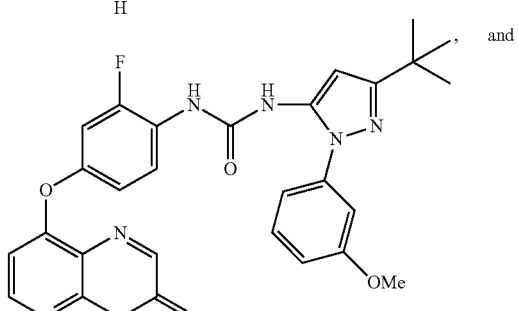

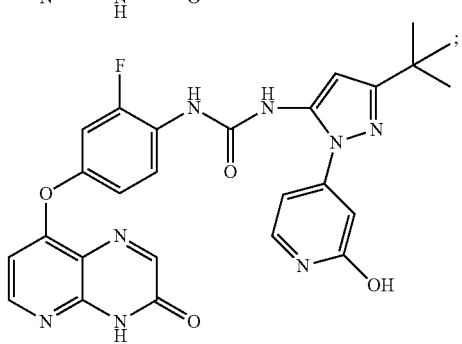

wherein the disorder is:
malignant melanoma; colorectal carcinoma; metastatic colorectal carcinoma; follicular thyroid cancer; insular thyroid cancer; papillary thyroid cancer; ovarian carcinoma; low grade ovarian carcinoma; non-small cell lung cancer; hairy cell leukemia; cholangiocarcinoma; pediatric low-grade glioma; pilocytic astrocytoma; ganglioglioma; pleomorphic xanthoastrocytoma; multiple myeloma; medullary carcinoma of the pancreas; pancreatic ductal adenocarcinoma; pancreatic cancer; non-small cell lung cancer; ovarian neoplasms; peritoneal neoplasms; fallopian tube neoplasms; lung cancer and associated pleural effusion; recurrent or metastatic squamous cell cancer of the head and neck; locally advanced nasopharyngeal carcinoma; glioblastoma; glioblastoma multiforme; giant cell glioblastoma; gliosarcoma; diffuse intrinsic pontine glioma; HIV-related kaposi sarcoma; multiple myeloma; renal cell carcinoma; metastatic gastric adenocarcinoma; acute myeloid leukemia; hepatocellular carcinoma; dermatofibrosarcoma; medullary thyroid cancer; papillary thyroid cancer; follicular thyroid cancer; myelodysplastic syndrome; neurofibromatosis type 1; plexiform neurofibroma; spinal cord neurofibroma; breast cancer; biliary tract neoplasms; cervical cancer; prostate cancer; melanoma; bladder carcinoma; urethra carcinoma; ureter carcinoma; renal carcinoma; pelvis carcinoma; sarcoma; liposarcoma; colon cancer; osteosarcoma; synovial carcinoma; neuroblastoma; or rhabdomyosarcoma.

2. A method according to claim 1, wherein the disorder is: malignant melanoma; colorectal carcinoma; metastatic colorectal carcinoma; follicular thyroid cancer; insular thyroid cancer; papillary thyroid cancer; ovarian carcinoma; low grade ovarian carcinoma; non-small cell lung cancer; hairy cell leukemia; cholangiocarcinoma; pediatric low-grade glioma; pilocytic astrocytoma; ganglioglioma;

pleomorphic xanthoastrocytoma; multiple myeloma; medullary carcinoma of the pancreas; or pancreatic ductal adenocarcinoma.

3. A method according to claim 1, wherein the disorder is malignant melanoma.

4. A method according to claim 1, wherein the disorder is colorectal carcinoma.

5. A method according to claim 1, wherein the disorder is pancreatic adenocarcinoma.

6. A method according to claim 1, wherein the disorder is: pancreatic cancer; non-small cell lung cancer; ovarian neoplasms; peritoneal neoplasms; fallopian tube neoplasms; lung cancer and associated pleural effusion; recurrent or metastatic squamous cell cancer of the head and neck; locally advanced nasopharyngeal carcinoma; glioblastoma; glioblastoma multiforme; giant cell glioblastoma; gliosarcoma; diffuse intrinsic pontine glioma; HIV-related kaposi sarcoma; multiple myeloma; renal cell carcinoma; metastatic gastric adenocarcinoma; acute myeloid leukemia; hepatocellular carcinoma; dermatofibrosarcoma; medullary thyroid cancer; papillary thyroid cancer; follicular thyroid cancer; myelodysplastic syndrome; neurofibromatosis type 1; plexiform neurofibroma; spinal cord neurofibroma; breast cancer; biliary tract neoplasms; cervical cancer; prostate cancer; melanoma; bladder carcinoma; urethra carcinoma; ureter carcinoma; renal carcinoma; pelvis carcinoma; sarcoma; liposarcoma; colon cancer; osteosarcoma; synovial carcinoma; neuroblastoma; or rhabdomyosarcoma.

7. A method according to claim 1, wherein the compound is a compound selected from compounds of the following formula and pharmaceutically acceptable salts thereof:

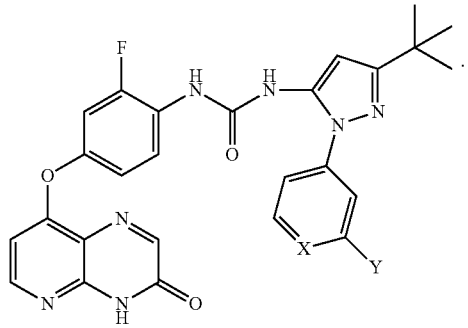

8. A method according to claim 1, wherein the compound is a compound selected from compounds of the following formula and pharmaceutically acceptable salts thereof:

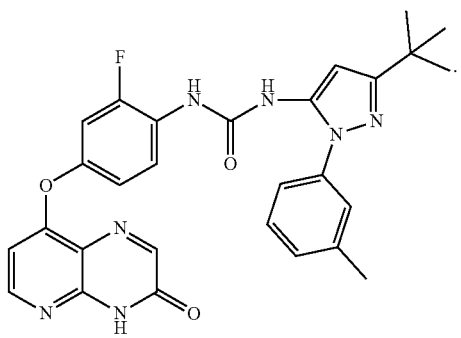 [SMILES: Cc1cccc(-n2nc(C(C)(C)C)cc2NC(=O)Nc2ccc(Oc3ccnc4[nH]c(=O)cnc34)cc2F)c1]

9. A method according to claim 1, wherein the compound is a compound selected from compounds of the following formula and pharmaceutically acceptable salts thereof:

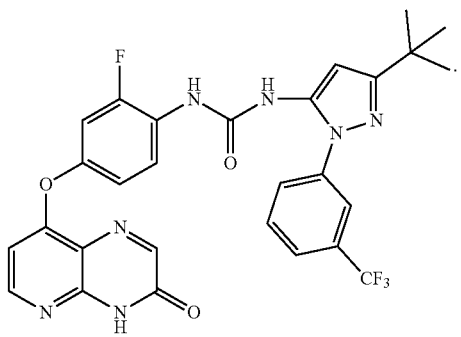 [SMILES: CC(C)(C)c1cc(NC(=O)Nc2ccc(Oc3ccnc4[nH]c(=O)cnc34)cc2F)n(-c2cccc(C(F)(F)F)c2)n1]

10. A method according to claim 1, wherein the compound is a compound selected from compounds of the following formula and pharmaceutically acceptable salts thereof:

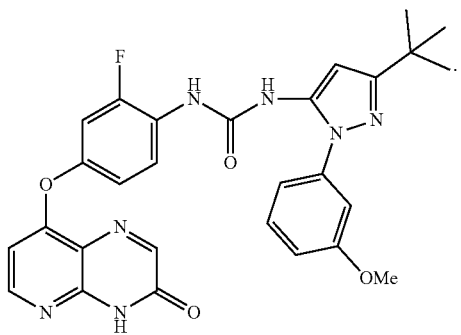 [SMILES: COc1cccc(-n2nc(C(C)(C)C)cc2NC(=O)Nc2ccc(Oc3ccnc4[nH]c(=O)cnc34)cc2F)c1]

11. A method according to claim 1, wherein the compound is a compound selected from compounds of the following formula and pharmaceutically acceptable salts thereof:

101

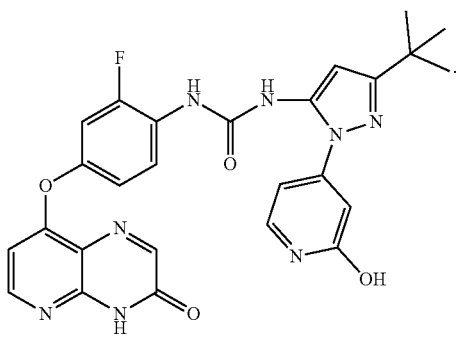 [SMILES: CC(C)(C)c1cc(NC(=O)Nc2ccc(Oc3ccnc4[nH]c(=O)cnc34)cc2F)n(-c2ccnc(O)c2)n1]

12. A method according to claim 3, wherein the compound is a compound selected from compounds of the following formula and pharmaceutically acceptable salts thereof:

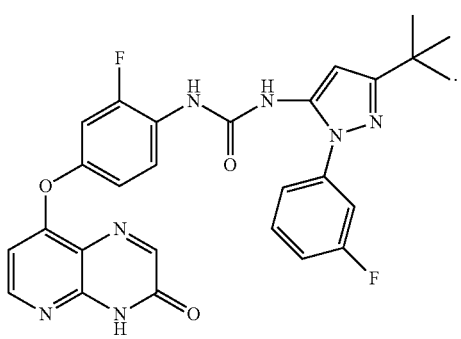 [SMILES: CC(C)(C)c1cc(NC(=O)Nc2ccc(Oc3ccnc4[nH]c(=O)cnc34)cc2F)n(-c2cccc(F)c2)n1]

13. A method according to claim 3, wherein the compound is a compound selected from compounds of the following formula and pharmaceutically acceptable salts thereof:

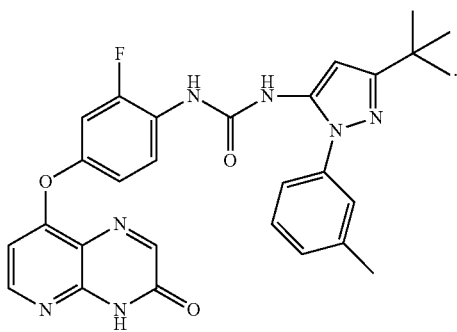 [SMILES: Cc1cccc(-n2nc(C(C)(C)C)cc2NC(=O)Nc2ccc(Oc3ccnc4[nH]c(=O)cnc34)cc2F)c1]

14. A method according to claim 3, wherein the compound is a compound selected from compounds of the following formula and pharmaceutically acceptable salts thereof:

102

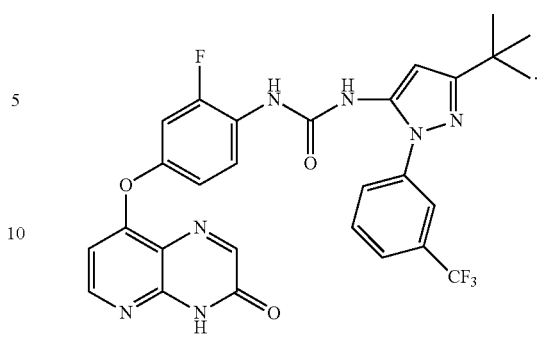

15. A method according to claim 3, wherein the compound is a compound selected from compounds of the following formula and pharmaceutically acceptable salts thereof:

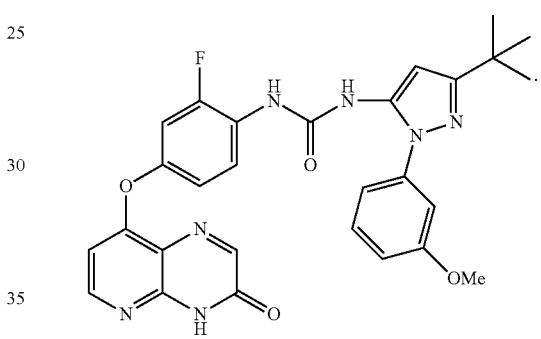

16. A method according to claim 3, wherein the compound is a compound selected from compounds of the following formula and pharmaceutically acceptable salts thereof:

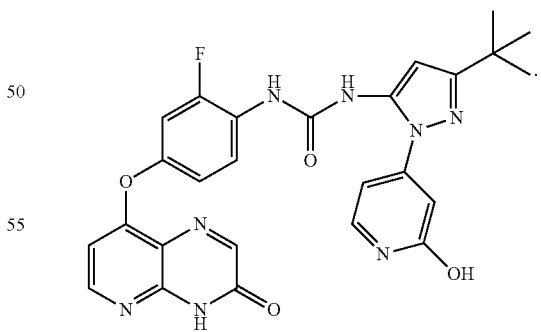

17. A method according to claim 4, wherein the compound is a compound selected from compounds of the following formula and pharmaceutically acceptable salts thereof:

18. A method according to claim 4, wherein the compound is a compound selected from compounds of the following formula and pharmaceutically acceptable salts thereof:

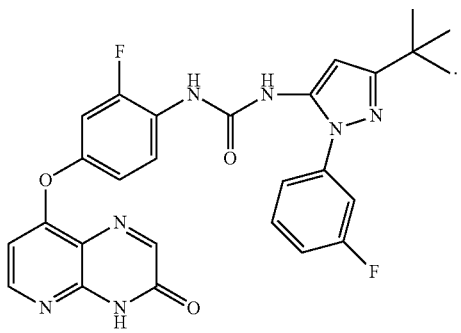 [SMILES: CC(C)(C)c1cc(NC(=O)Nc2ccc(Oc3ccnc4[nH]c(=O)cnc34)cc2F)n(-c2cccc(F)c2)n1]

19. A method according to claim 4, wherein the compound is a compound selected from compounds of the following formula and pharmaceutically acceptable salts thereof:

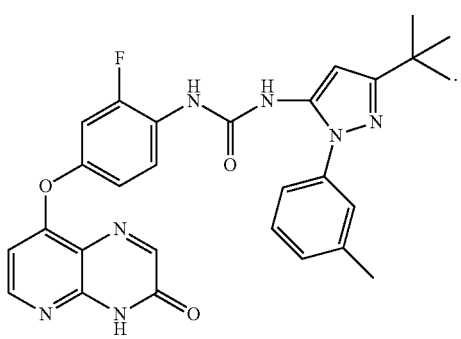 [SMILES: Cc1cccc(-n2nc(C(C)(C)C)cc2NC(=O)Nc2ccc(Oc3ccnc4[nH]c(=O)cnc34)cc2F)c1]

20. A method according to claim 4, wherein the compound is a compound selected from compounds of the following formula and pharmaceutically acceptable salts thereof:

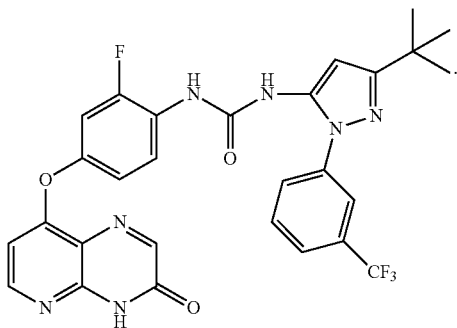 [SMILES: CC(C)(C)c1cc(NC(=O)Nc2ccc(Oc3ccnc4[nH]c(=O)cnc34)cc2F)n(-c2cccc(C(F)(F)F)c2)n1]

21. A method according to claim 4, wherein the compound is a compound selected from compounds of the following formula and pharmaceutically acceptable salts thereof:

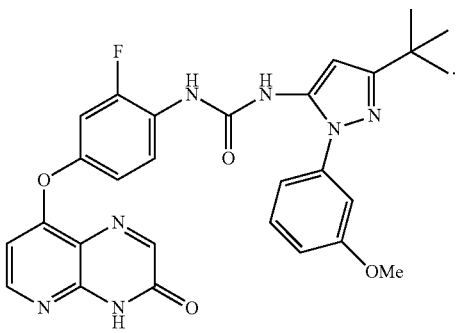 [SMILES: COc1cccc(-n2nc(C(C)(C)C)cc2NC(=O)Nc2ccc(Oc3ccnc4[nH]c(=O)cnc34)cc2F)c1]

22. A method according to claim 5, wherein the compound is a compound selected from compounds of the following formula and pharmaceutically acceptable salts thereof:

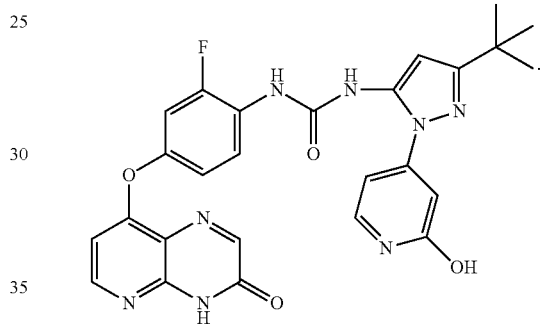

23. A method according to claim 5, wherein the compound is a compound selected from compounds of the following formula and pharmaceutically acceptable salts thereof:

24. A method according to claim 5, wherein the compound is a compound selected from compounds of the following formula and pharmaceutically acceptable salts thereof:

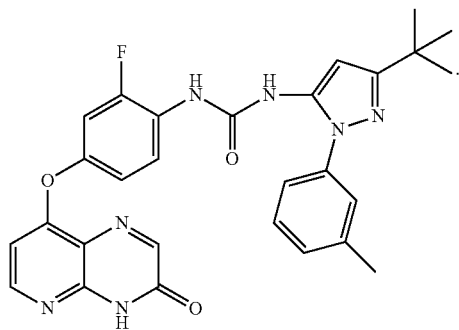 [SMILES: Cc1cccc(-n2nc(C(C)(C)C)cc2NC(=O)Nc2ccc(Oc3ccnc4[nH]c(=O)cnc34)cc2F)c1]

25. A method according to claim 5, wherein the compound is a compound selected from compounds of the following formula and pharmaceutically acceptable salts thereof:

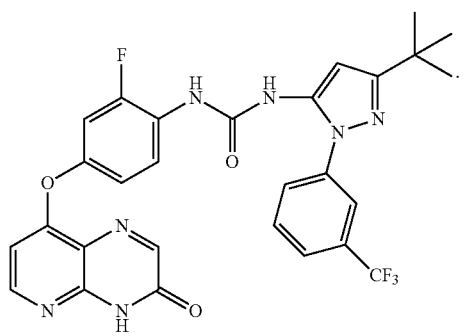 [SMILES: CC(C)(C)c1cc(NC(=O)Nc2ccc(Oc3ccnc4[nH]c(=O)cnc34)cc2F)n(-c2cccc(C(F)(F)F)c2)n1]

26. A method according to claim 5, wherein the compound is a compound selected from compounds of the following formula and pharmaceutically acceptable salts thereof:

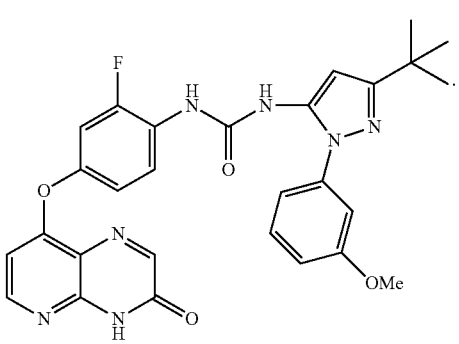 [SMILES: COc1cccc(-n2nc(C(C)(C)C)cc2NC(=O)Nc2ccc(Oc3ccnc4[nH]c(=O)cnc34)cc2F)c1]

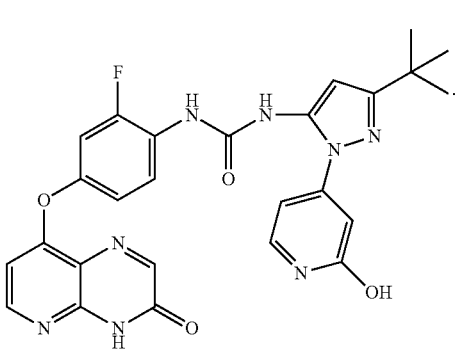 [SMILES: CC(C)(C)c1cc(NC(=O)Nc2ccc(Oc3ccnc4[nH]c(=O)cnc34)cc2F)n(-c2ccnc(O)c2)n1]

* * * * *